United States Patent [19]

Broadhurst et al.

[11] Patent Number: 4,526,960

[45] Date of Patent: Jul. 2, 1985

[54] ANTHRACYCLINE GLYCOSIDES

[75] Inventors: Michael J. Broadhurst, Baldock; Cedric H. Hassall, Harpenden; Gareth J. Thomas, Luton, all of United Kingdom

[73] Assignee: Hoffmann-La Roche Inc., Nutley, N.J.

[21] Appl. No.: 535,968

[22] Filed: Sep. 26, 1983

[30] Foreign Application Priority Data

Sep. 28, 1982 [GB] United Kingdom ................. 8227686
Jul. 15, 1983 [GB] United Kingdom ................. 8319251

[51] Int. Cl.³ ........................................... C07H 15/24
[52] U.S. Cl. ..................................... 536/6.4; 260/365
[58] Field of Search ................ 260/365; 536/6.4, 53, 536/55.3

[56] References Cited

U.S. PATENT DOCUMENTS

| | | | |
|---|---|---|---|
| 4,125,709 | 11/1978 | Smith | 536/53 |
| 4,183,919 | 1/1980 | Cassinelli et al. | 536/6.4 |
| 4,263,428 | 4/1981 | Apple et al. | 536/6.4 |
| 4,275,192 | 6/1981 | Apple et al. | 536/6.4 |
| 4,393,052 | 7/1983 | Bargiotti et al. | 424/180 |

FOREIGN PATENT DOCUMENTS

| | | | |
|---|---|---|---|
| 0044954 | 2/1982 | European Pat. Off. | 536/6.4 |
| 2735891 | 2/1978 | Fed. Rep. of Germany | 536/6.4 |

OTHER PUBLICATIONS

Matsuzawa et al., "The Journal of Antibiotics", vol. XXXIV, No. 12, Dec. 1981, pp. 1596–1607.

Primary Examiner—Johnnie R. Brown
Attorney, Agent, or Firm—Jon S. Saxe; Bernard S. Leon; Frank P. Hoffman

[57] ABSTRACT

This invention relates to compounds of the formula

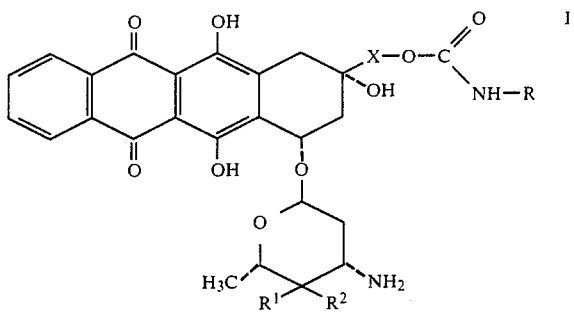

wherein R is a hydrogen atom, a lower alkyl, aryl or aryl-(lower alkyl) group, a 5-membered or 6-membered heteroaromatic group in which the hetero atom is nitrogen, oxygen or sulphur or a group of the formula $-(CH_2)_n-COR'$ or

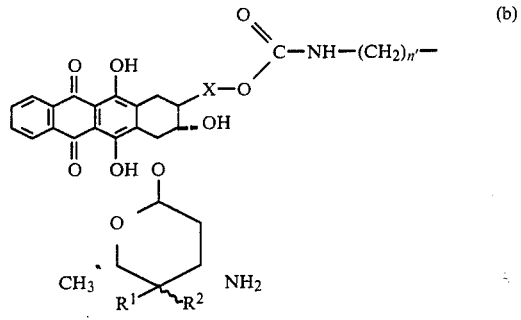

wherein R' is a hydroxy, lower alkoxy, amino, lower alkylamino, di-(lower alkyl)amino or arylamino group, n stands for an integer of 1 to 4, n' stands for an integer of 2 to 10, $R^1$ and $R^2$ each are a hydrogen atom or one of $R^1$ and $R^2$ is a hydrogen atom and the other is a hydroxy, lower alkoxy or benzyloxy group and X is a group of the formula $-CH_2-$,  $-\underset{\underset{CH_3}{|}}{CH}-$  or  $-CH_2-CH_2-$ (i) (ii) (iii)

and pharmaceutically acceptable acid addition salts thereof, a process for their manufacture and medicaments containing them. These compounds and salts possess antitumor activity.

13 Claims, No Drawings

ANTHRACYCLINE GLYCOSIDES

DESCRIPTION OF THE INVENTION

The present invention is concerned with anthracycline glycosides, a process for their manufacture, medicaments containing said glycosides and the use of said glycosides.

The anthracycline glycosides provided by the present invention are compounds of the formula

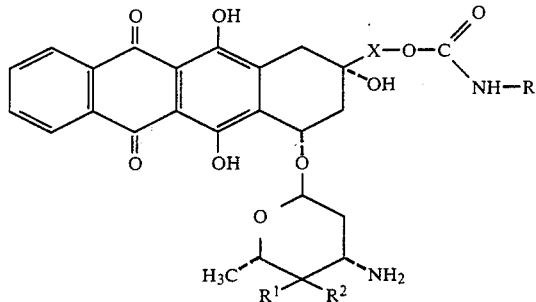

wherein R is a hydrogen atom, a lower alkyl, aryl or aryl-(lower alkyl) group, a 5-membered or 6-membered heteroaromatic group in which the hetero atom is nitrogen, oxygen or sulphur or a group of the formula $$-(CH_2)_n-COR' \quad (a)$$

or

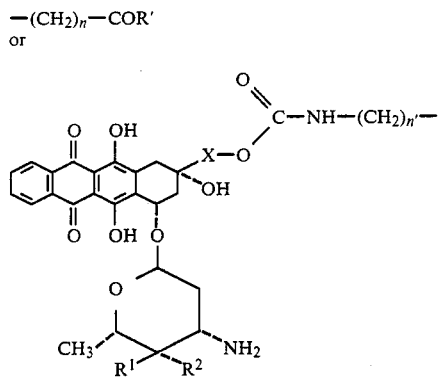

wherein, R' is a hydroxy, lower alkoxy, amino, lower alkylamino, di(lower alkyl)amino or arylamino group, n stands for an integer of 1 to 4, n' stands for an integer of 2 to 10, $R^1$ and $R^2$ each are a hydrogen atom or one of $R^1$ and $R^2$ is a hydrogen atom and the other is a hydroxy, lower alkoxy or benzyloxy group and X is a group of the formula

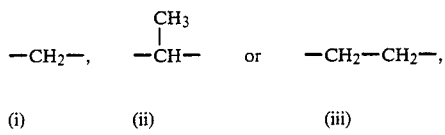

and pharmaceutically acceptable acid addition salts thereof.

The term "lower alkyl" used in this Specification, alone or in combinations such as in aryl-(lower alkyl), lower alkylamino and di(lower alkyl)amino, means a straight-chain or branched-chain alkyl group containing from 1 to 5 carbon atoms such as methyl, ethyl, n-propyl, isopropyl, n-butyl, tert.butyl, n-pentyl and the like. The term "aryl", alone or in combinations such as in aryl-(lower alkyl) and arylamino, means the phenyl group or a substituted-phenyl group, i.e. a phenyl group carrying one or more substituents selected from, for example, lower alkyl, lower alkoxy, halogen, nitro, amino, carboxy, hydroxy, cyano and trifluoromethyl. Examples of substituted-phenyl groups are thus p-tolyl, p-methoxyphenyl, m-hydroxyphenyl, o-nitrophenyl, p-nitrophenyl, p-chlorophenyl, 2,4-dichlorophenyl and the like. Benzyl, p-chlorobenzyl and 2-phenylethyl can be named as examples of aryl-(lower alkyl) groups and anilino can be named as an example of an arylamino group. Examples of 5-membered and 6-membered heteroaromatic groups denoted by R are pyridyl, thienyl and the like. The term "lower alkoxy" means a lower alkyl ether group in which the lower alkyl moiety is as defined earlier, examples of such lower alkoxy groups being methoxy, methoxy, n-propoxy, isopropoxy etc. Examples of lower alkylamino groups are methylamino, ethylamino, n-propylamino and the like and examples of di(lower alkyl)amino groups are dimethylamino, diethylamino and the like. The term "halogen" means fluorine, chlorine, bromine or iodine.

An interesting class of compounds of formula I comprises those in which R represents a lower alkyl, aryl or aryl-(lower alkyl) group, a 5-membered or 6-membered heteroaromatic group in which the hetero atom is nitrogen, oxygen or sulphur or a group of formula (a) and $R^1$ and $R^2$ each represent a hydrogen atom or one of $R^1$ and $R^2$ represents a hydrogen atom and the other represents a hydroxy or methoxy group.

A preferred class of compounds of formula I comprises those in which R represents an aryl group, especially phenyl. Compounds of formula I in which one of $R^1$ and $R^2$ represents a hydrogen atom and the other represents a hydroxy group are also preferred as are compounds of formula I in which X represents a group of formula (i) or (ii) hereinbefore.

Particularly preferred compounds provided by the present invention are:

(1S)-cis-1-[(3-amino-2,3,6-trideoxy-α-L-lyxohexopyranosyl)oxy]-1,2,3,4,6,11-hexahydro-3,5,12-trihydroxy-6,11-dioxo-3-(phenylcarbamoyloxy)methylnaphthacene, (1S)-cis-1-[(3-amino-2,3,6-trideoxy-α-L-arabinohexopyranosyl)oxy]-1,2,3,4,6,11-hexahydro-3,5,12-trihydroxy-6,11-dioxo-3-(phenylcarbamoyloxy)methylnaphthacene, (1S)-cis-1-[(3-amino-2,3,6-trideoxy-α-L-lyxohexopyranosyl)oxy]-1,2,3,4,6,11-hexahydro-3,5,12-trihydroxy-6,11-dioxo-3-[1(R)-phenylcarbamoyloxy)ethyl]naphthacene, (1S)-cis-1-[(3-amino-2,3,6-trideoxy-α-L-arabinohexopyranosyl)oxy]-1,2,3,4,6,11-hexahydro-3,5,12-trihydroxy-6,11-dioxo-3-[1(R)-(phenylcarbamoyloxy)ethyl]naphthacene, and pharmaceutically acceptable acid addition salts thereof.

Examples of other interesting compounds provided by the present invention are:

(1S)-cis-1-[(3-amino-2,3,6-trideoxy-α-L-lyxohexopyranosyl)oxy]-3-(4-chlorophenylcarbamoyloxy)-methyl-1,2,3,4,6,11-hexahydro-3,5,12-trihydroxy-6,11-dioxonaphthacene, (1S)-cis-1-[(3-amino-2,3,6-trideoxy-α-L-lyxohexopyranosyl)oxy]-1,2,3,4,6,11-hexahydro-3,5,12-trihydroxy-3-(4-nitrophenylcarbamoyloxy)methyl-6,11-dioxonaphthacene, (1S)-cis-1-[(3-amino-2,3,6-trideoxy-α-L-lyxohexopyranosyl)oxy]-1,2,3,4,6,11-hexahydro-3,5,12-trihydroxy-3-(4-methoxyphenylcarbamoyloxy)methyl-6,11-dioxonaphthacene, (1S)-cis-1-[(3-amino-2,3,6-trideoxy-α-L-lyxohexopyranosyl)oxy]-1,2,3,4,6,11-hexahydro-3,5,12-trihydroxy-3-(3-hydroxyphenylcarbamoyloxy)methyl-6,11-dioxonaphthacene, (1S)-cis-1-[(3-amino-2,3,6-trideoxy-α-L-lyxohexopyranosyl)oxy]-1,2,3,4,6,11-hexahydro-3,5,12-trihydroxy-3-(methylcarbamoyloxy)methyl-6,11-dioxonaphthacene, (1S)-cis-1-[(3-amino-2,3,6-trideoxy-α-L-lyxohexopyranosyl)oxy]-1,2,3,4,6,11-hexahydro-3,5,12-trihydroxy-3-(2-thienylcarbamoyloxy)methyl-6,11-dioxonaphthacene, (1S)-cis-1-[(3-amino-2,3,4,6-tetradeoxy-α-L-threohexopyranosyl)oxy]-1,2,3,4,6,11-hexahydro-3,5,12-trihydroxy-6,11-dioxo-3-(phenylcarbamoyloxy)methylnaphthacene, (1S)-cis-1-[(3-amino-2,3,4,6-tetradeoxy-α-L-threohexopyranosyl)oxy]-1,2,3,4,6,11-hexahydro-3,5,12-trihydroxy-6,11-dioxo-3-(3-pyridylcarbamoyloxy)methylnaphthacene, (1S)-cis-1-[(3-amino-2,3,6-trideoxy-4-O-methyl-α-L-lyxohexopyranosyl)oxy]-3-(benzylcarbamoyloxy)-methyl-1,2,3,4,6,11-hexahydro-3,5,12-trihydroxy-6,11-dioxonaphthacene, (1S)-cis-1-[(3-amino-2,3,6-trideoxy-α-L-lyxohexopyranosyl)oxy]-3-[(2-carboxyethyl)carbamoyloxy]-methyl-1,2,3,4,6,11-hexahydro-3,5,12-trihydroxy-6,11-dioxonaphthacene, (1S)-cis-1-[(3-amino-2,3,6-trideoxy-α-L-lyxohexopyranosyl)oxy]-1,2,3,4,6,11-hexahydro-3,5,12-trihydroxy-3-[[2-(methoxycarbonyl)ethyl]carbamoyloxy]-methyl-6,11-dioxonaphthacene, (1S)-cis-1-[(3-amino-2,3,6-trideoxy-α-L-lyxohexopyranosyl)oxy]-1,2,3,4,6,11-hexahydro-3,5,12-trihydroxy- 6,11-dioxo-3-[[2-(propylcarbamoyl)ethyl]carbamoyloxy]methylnaphthacene, (1S)-cis-1-[(3-amino-2,3,6-trideoxy-α-L-arabinohexopyranosyl)oxy]-1,2,3,4,6,11-hexahydro-3,5,12-trihydroxy-6,11-dioxo-3-[[2-(propylcarbamoyl)ethyl]carbamoyloxy]methylnaphthacene, (1S)-cis-1-[(3-amino-2,3,6-trideoxy-4-O-methyl-α-L-lyxohexopyranosyl)oxy]-1,2,3,4,6,11-hexahydro-3,5,12-trihydroxy-6,11-dioxo-3-[2-(phenylcarbamoyloxy)ethyl]naphthacene and pharmaceutically acceptable acid addition salts thereof.

Further examples of interesting compounds provided by the present invention are:

(1S)-cis-1-[(3-amino-2,3,6-trideoxy-α-L-arabinohexopyranosyl)oxy]-1,2,3,4,6,11-hexahydro-3,5,12-trihydroxy-6,11-dioxo-3-(p-tolylcarbamoyloxy)methylnaphthacene, (1S)-cis-1-[(3-amino-2,3,6-trideoxy-4-O-methyl-α-L-lyxohexopyranosyl)oxy]-3-(carbamoyloxy)methyl-1,2,3,4,6,11-hexahydro-3,5,12-trihydroxy-6,11-dioxonaphthacene, (1S)-cis-1-[(3-amino-2,3,6-trideoxy-4-O-methyl-α-L-lyxohexopyranosyl)oxy]-1,2,3,4,6,11-hexahydro-3,5,12-trihydroxy-6,11-dioxo-3-(phenylcarbamoyloxy)methylnaphthacene, (1S)-cis-1-[(3-amino-2,3,6-trideoxy-4-O-methyl-α-L-lyxohexopyranosyl)oxy]-1,2,3,4,6,11-hexahydro-3,5,12-trihydroxy-3-[(o-nitrobenzylcarbamoyloxy)-methyl]-6,11-dioxonaphthacene, (1S)-cis-1-[(3-amino-2,3,6-trideoxy-α-L-arabinohexopyranosyl)oxy]-1,2,3,4,6,11-hexahydro-3,5,12-trihydroxy-3-(2-thienylcarbamoyloxy)methyl-6,11-dioxonaphthacene, (1S)-cis-1-[(3-amino-2,3,6-trideoxy-α-L-arabinohexopyranosyl)oxy]-1,2,3,4,6,11-hexahydro-3,5,12-trihydroxy-3-(3-thienylcarbamoyloxy)methyl-6,11-dioxonaphthacene, (1S)-cis-1-[(3-amino-2,3,6-trideoxy-4-O-methyl-α-L-arabinohexopyranosyl)oxy]-1,2,3,4,6,11-hexahydro-3,5,12-trihydroxy-6,11-dioxo-3-(phenylcarbamoyloxy)methylnaphthacene, (1S)-cis-1-[(3-amino-2,3,6-trideoxy-4-O-ethyl-α-L-lyxohexopyranosyl)oxy]-1,2,3,4,6,11-hexahydro-3,5,12-trihydroxy-6,11-dioxo-3-(phenylcarbamoyloxy)methylnaphthacene, (1S)-cis-1-[(3-amino-4-O-benzyl-2,3,6-trideoxy-α-L-lyxohexopyranosyl)oxy]-1,2,3,4,6,11-hexahydro-3,5,12-trihydroxy-6,11-dioxo-3-(phenylcarbamoyloxy)methylnaphthacene, 3,3'-[tetramethylenebis(carbamoyloxymethylene)]bis-(1S)-cis-[(3-amino-2,3,4,6-tetradeoxy-α-L-threohexopyranosyl)oxy]-1,2,3,4,6,11-hexahydro-3,5,12-trihydroxy-6,11-dioxonaphthacene, (1S)-cis-1-[(3-amino-2,3,6-trideoxy-α-L-arabinohexopyranosyl)oxy]-3-(4-chlorophenylcarbamoyloxy)-methyl-1,2,3,4,6,11-hexahydro-3,5,12-trihydroxy-6,11-dioxonaphthacene, (1S)-cis-1-[(3-amino-2,3,6-trideoxy-α-L-arabinohexopyranosyl)oxy]-3-(carbamoyloxy)methyl-1,2,3,4,6,11-hexahydro-3,5,12-trihydroxy-6,11-dioxonaphthacene, (1S)-cis-1-[(3-amino-2,3,6-trideoxy-α-L-arabinohexopyranosyl)oxy]-1,2,3,4,6,11-hexahydro-3,5,12-trihydroxy-6,11-dioxo-3-[1(S)-(phenylcarbamoyloxy)ethyl]naphthacene.

(1S)-cis-1-[(3-amino-2,3,6-trideoxy-4-O-methyl-α-L-lyxohexopyranosyl)oxy]-1,2,3,4,6,11-hexahydro-3,5,12-trihydroxy-6,11-dioxo-3-[1(R)-(phenylcarbamoyloxy)ethyl]naphthacene and pharmaceutically acceptable acid addition salts thereof.

According to the process provided by the present invention, the compounds of formula I and their pharmaceutically acceptable acid addition salts are manufactured by (a) for the manufacture of the compounds of formula I in which R represents a hydrogen atom, a lower alkyl, aryl or aryl-(lower alkyl) group, a 5-membered or 6-membered heterocyclic group in which the hetero atom is oxygen or sulphur or a group of formula (a) or (b), reacting a compound of the formula

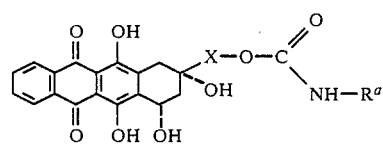

II wherein $R^a$ is a hydrogen atom, a trichloroacetyl, lower alkyl, aryl or aryl-(lower alkyl) group, a 5-membered or 6-membered heteroaromatic group in which the hetero atom is oxygen or sulphur, a group of formula (a) hereinbefore or a group of the formula

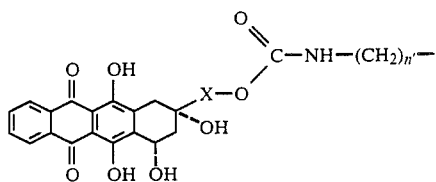

and n' and X are as above, with the proviso that any carboxy, hydroxy or amino group present on an aryl substituent is in protected form and a carboxy group present on group (a) is in protected form, with a compound of the formula

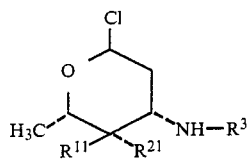

wherein $R^3$ is an amino protecting group and $R^{11}$ and $R^{21}$ each are a hydrogen atom or one of $R^{11}$ and $R^{21}$ is a hydrogen atom and the other is a lower alkoxy, benzoyloxy or protected hydroxy group, and cleaving off the protecting group or protecting groups present in the reaction product, or (b) reacting a compound of the formula

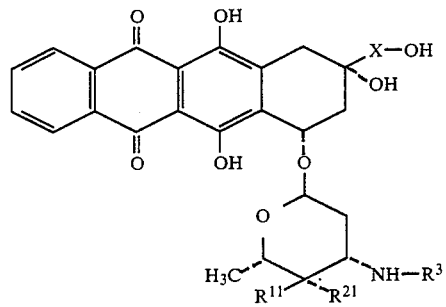

wherein $R^3$, $R^{11}$, $R^{21}$ and X are as above with an isocyanate of the formula

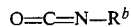

wherein $R^b$ is a trichloroacetyl, lower alkyl, aryl or aryl-(lower alkyl) group, a 5-membered or 6-membered heteroaromatic group in which the hetero atom is nitrogen, oxygen or sulphur or a group of formula (a) hereinbefore, with the proviso that any carboxy, hydroxy or amino group present on an aryl substituent is in protected form and a carboxy group present on group (a) is in protected form, or with a diisocyanate of the formula

wherein n' are as above and cleaving off the protecting group or protecting groups present in the reaction product, or (c) for the manufacture of a compound of formula I in which R' represents a lower alkoxy group, appropriately esterifying a corresponding compound of formula I in which R' represents a hydroxy group, and, (d) if desired, converting a compound of formula I into a pharmaceutically acceptable acid addition salt.

A carboxy or hydroxy group present in $R^a$ in a compound of formula II can be protected in the form of any conventional readily hydrolyzable ester. Preferably, for the protection of a hydroxy group an ester is derived from a lower alkanecarboxylic acid such as acetic acid etc. An amino group present in $R^a$ can be protected in a conventional manner; for example by means of a suitable acyl group.

The amino protecting group denoted by $R^3$ in a compound of formula II can be any amino protecting group which is conventionally used in sugar chemistry. For example, $R^3$ can represent a chloroacetyl, trifluoroacetyl or like group. When a protected hydroxy group is present in a compound of formula II, this can be any suitable protected hydroxy group known per se in sugar chemistry; for example, p-nitrobenzoyloxy and the like.

The reaction of a compound of formula II with a compound of formula III in accordance with embodiment (a) of the process can be carried out in a manner known per se. In a preferred procedure, the reaction is carried out in an inert organic solvent and in the presence of a soluble silver salt. Examples of inert organic solvents which can be used are dichloromethane, dimethylformamide, tetrahydrofuran and the like. Tetrahydrofuran and mixtures of tetrahydrofuran with dimethylformamide are preferred. Silver trifluoromethanesulphonate is an especially suitable soluble silver salt for use in the present reaction. The reaction is conveniently carried out at a low temperature (e.g at about $-5°$ C.) and at atmospheric pressure.

The reaction of a compound of formula II with a compound of formula III yields a compound of the formula

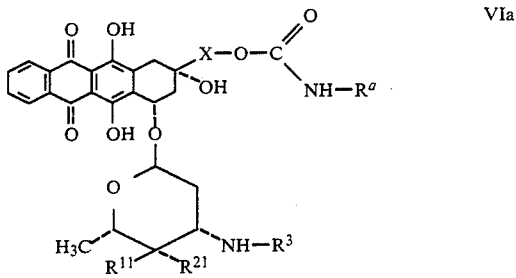

wherein $R^a$, $R^3$, $R^{11}$, $R^{21}$ and X are as above which is converted into a desired compound of formula I by cleaving off the protecting group or protecting groups present.

The cleavage of the protecting group or protecting groups from a compound of formula VIa can be carried out in a manner known per se. For example, when $R^a$ represents a trichloroacetyl group, this group can be cleaved off by treatment with aqueous alkali such as aqueous sodium hydroxide. Again, for example, when $R^3$ represents a trifluoroacetyl group, this group can be also cleaved off by treatment with aqueous alkali such as aqueous sodium hydroxide. When $R^3$ represents a chloroacetyl group this group can be cleaved off using thiourea under essentially neutral conditions. When one of $R^{11}$ and $R^{21}$ represents a p-nitrobenzoyloxy group, this group can be converted into a hydroxy group by treatment with aqueous alkali such as aqueous sodium hydroxide. It will be appreciated that when two or more protecting groups are present in a compound of formula VIa, then the cleavage of these groups can be carried out in one or more steps by appropriate choice of the cleavage reagents and/or cleavage conditions.

A carboxy, hydroxy or amino group present in $R^b$ in an isocyanate of formula Va can be protected in the same manner as described earlier in connection with the protection of these groups in $R^a$ in a compound of formula II.

The reaction of a compound of formula IV with an isocyanate of formula Va or a diisocyanate of formula Vb in accordance with embodiment (b) of the process is conveniently carried out in a tertiary organic amine (e.g. pyridine or the like). When an isocyanate of formula Va is used, the reaction can conveniently be carried out at an elevated temperature, for example a temperature from about 60° C. to about 80° C. The isocyanate of formula Va can be formed in situ by using a corresponding azide of the formula $R^b$—CO—$N_3$ and carrying out the reaction at a temperature at which the azide liberates nitrogen and rearranges to form the isocyanate. When a diisocyanate of formula Vb is used, it can be convenient to carry out the reaction at about room temperature, suitably over an extended period of time.

The reaction of a compound of formula IV with an isocyanate of formula Va or a diisocyanate of formula Vb yields a compound of the formula

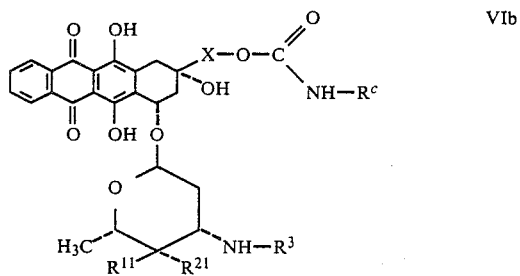

VIb wherein $R^c$ is a trichloroacetyl, lower alkyl or aryl-(lower alkyl) group, a 5-membered or 6-membered heteroaromatic group in which the hetero atom is nitrogen, oxygen or sulphur, a group of formula (a) hereinbefore or a group of the formula

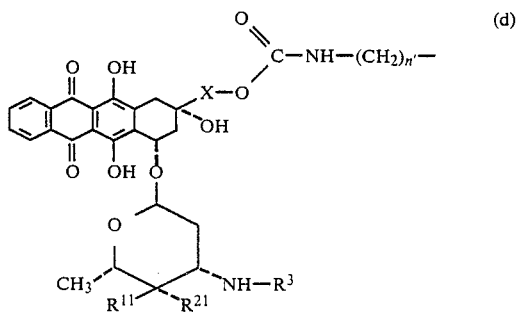

(d)

and $R^3$, $R^{11}$, $R^{21}$, n' and X are as above, with the proviso that any carboxy, hydroxy or amino group present on an aryl substituent is in protected form and a carboxy group present on group (a) is in protected form, which is converted into the desired compound of formula I by cleaving off the protecting group or protecting groups present.

The cleavage of the protecting group or protecting groups from a compound of formula VIb can be carried out in the same manner as that described earlier in connection with the cleavage of the protecting group or groups from a compound of formula VIa.

The esterification of a compound of formula I in which R' represents a hydroxy group in accordance with embodiment (c) of the present process to give a corresponding compound of formula I in which R' represents a lower alkoxy group can be carried out in a manner known per se; for example, by treatment with an appropriate diazoalkane such as diazomethane or with an appropriate lower alkanolic hydrogen chloride solution such as methanolic hydrogen chloride.

The compounds of formula I can be converted into pharmaceutically acceptable acid addition salts in accordance with embodiment (d) of the present process by treatment with pharmaceutically acceptable inorganic acids (e.g. hydrochloric acid, hydrobromic acid, sulphuric acid, phosphoric acid etc) and with pharmaceutically acceptable organic acids (e.g. acetic acid, tartaric acid, citric acid, fumaric acid maleic acid, malic acid, methanesulphonic acid, toluene-4-sulphonic acid etc).

The compounds of formula I contain two asymmetric carbon atoms in the A-ring of the aglycone portion and it will be appreciated that the invention includes within its scope both the (1S)-cis compounds and the (1R)-cis compounds.

The compounds of formula II used as starting materials in embodiment (a) of the process provided by the present invention are novel compounds and also form part of the present invention.

The compounds of formula II can be prepared, for example, by reacting a compound of the formula

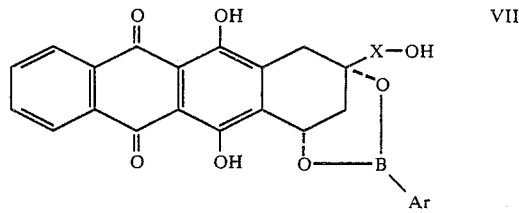

VII wherein X is as above and Ar is an aryl group, with an isocyanate of the formula

$O=C=N-R^{a'}$      VIII wherein $R^{a'}$ has any of the values of $R^a$ hereinbefore except a hydrogen atom, or with a diisocyanate of formula Vb hereinbefore and subjecting the reaction product of the formula

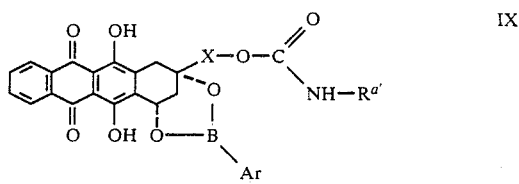

IX wherein $R^{a'}$, X and Ar are as above to an ester exchange with a 1,3-diol and, if desired, cleaving off a trichloroacetyl group denoted by $R^{a'}$ from the product.

The reaction of a compound of formula VII with an isocyanate of formula VIII or a diisocyanate of formula Vb can be carried out in a manner analogous to that described earlier in connection with the reaction of a compound of formula IV with an isocyanate of formula Va or a diisocyanate of formula Vb. The isocyanates of formula VIII can be prepared in situ from the corresponding azides in the manner described earlier.

The reaction product of formula IX is then subjected to an ester exchange with a 1,3-diol. This is suitably effected by reacting a compound of formula IX with an excess of a 1,3-diol in the presence of an acid. An especially preferred 1,3-diol is 2-methyl-2,4-pentanediol. Preferred among the acids which can be used are the lower alkanecarboxylic acids such as acetic acid and the like. This reaction is conveniently carried out in the presence of an inert organic solvent such as a halogenated hydrocarbon (e.g. dichloromethane etc) and at about room temperature.

The optional cleavage of the trichloroacetyl group denoted by $R^{a'}$ from a compound of formula II can be carried out as described earlier in connection with the cleavage of the trichloroacetyl group from a compound of formula VIa.

The compounds of formula VII hereinbefore can be prepared, for example, as described in the Examples hereinafter or in analogy thereto.

The compounds of formula IV used as starting materials in embodiment (b) of the process provided by the present invention are novel compounds and also form part of the present invention.

The compounds of formula IV can be prepared, for example, by reacting a compound of the formula

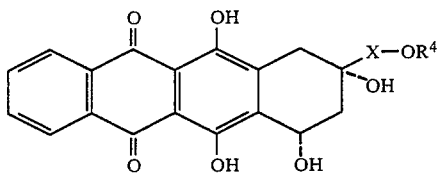

wherein X is as above and $R^4$ is a acyl group, preferably acetyl, with a compound of formula III hereinbefore and deacylating the reaction product of the formula

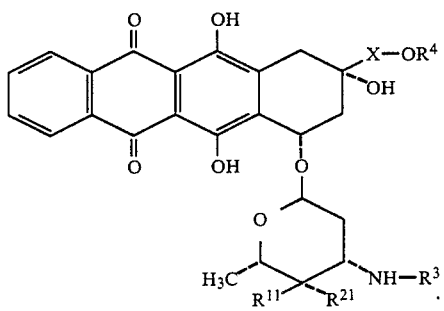

wherein $R^3$, $R^4$, $R^{11}$, $R^{21}$ and X are as above.

The reaction of a compound of formula X with a compound of formula III can be carried out in a manner analogous to that described earlier in connection with the reaction of a compound of formula II with a compound of formula III.

The deacylation of a compound of formula XI can be carried out in a conventional manner; for example by treatment with an appropriate base.

The compounds of formula X hereinbefore can be prepared as described in the Examples hereinafter or in analogy thereto.

The compounds of formula I and their pharmaceutically acceptable acid addition salts possess antitumour activity.

The antitumour activity of the compounds of formula I and their pharmaceutically acceptable acid addition salts can be demonstrated using standard pharmacological tests. For example, the in vivo antitumour activity can be demonstrated using the following test:

The test was carried out using laboratory mice. The test substances were dissolved in water or, if insoluble, were suspended in propyleneglycol. Solutions and suspensions were used only for 2 days and were stored in the dark at 4° C. $10^5$ viable lymphocyte leukemia tumour cells were injected into mice and treatment was started the same day with five daily intraperitoneal injections of the test substance per week. Untreated control animals died between day 9 and day 12. The efficacy of the treatment is expressed as the quotient T/C which denotes the mean survival time of treated animals divided by the mean survival time of control animals. The following Table gives the results obtained in this test using representative compounds provided by the present invention:

TABLE

| Compound | Dosage (mg/kg i.p.) | T/C |
|---|---|---|
| A | 0.5 | 2.0 |
| B | 0.5 | 2.8 |
| C | 1.0 | 2.7 |
| D | 1.0 | 2.5 |
| E | 2.0 | 3.3 |

Compounds:
A: (1S)-cis-1-[(3-amino-2,3,6-trideoxy-α-L-lyxohexopyranosyl)oxy]-1,2,3,4,6,11-hexahydro-3,5,12-trihydroxy-6,11-dioxo 3-phenyl-carbamoyloxy)methylnaphthacene hydrochloride.
B: (1S)-cis-1-[(3-amino-2,3,6-trideoxy-α-L-arabinohexopyranosyl)oxy]-1,2,3,4,6,11-hexahydro-3,5,12-trihydroxy-6,11-dioxo-3-(phenylcarbamoyloxy)methylnaphthacene hydrochloride.
C: (1S)-cis-1-[(3-amino-2,3 6-trideoxy-α-L-lyxohexopyranosyl)oxy]-1,2,3,4,6,11-hexahydro-3,5,12-trihydroxy-3-(2-thienylcarbamoyloxy)methyl-6,11 dioxonaphthacene hydrochloride.
D: (1S)-cis-1-[(3-amino-2,3,6-trideoxy-α-L-lyxohexopyranosyl)oxy]-3-(4-chlorophenylcarbamoyloxy)methyl-1,2,3,4,6,11-hexahydro-3,5,12-trihydroxy-6,11 dioxonaphthacene hydrochloride.
E: (1S)-cis-1-[(3-amino-2,3,6-trideoxy-4-O—methyl-α-L-lyxohexopyranosyl)oxy]-3-(benzylcarbamoyloxy)methyl-1,2,3,4,6,11-hexahydro-3,5,12-trihydroxy-6,11-dioxonaphthacene hydrochloride.

The compounds of formula I and their pharmaceutically acceptable acid addition salts can be used as medicaments; for example, in the form of pharmaceutical preparations which contain them in association with a compatible pharmaceutical carrier material. This carrier material can be an inert organic or inorganic carrier material suitable for enteral (e.g. oral) or parenteral administration. Examples of such carrier materials are water, gelatin, talc, starch, magnesium stearate, gum arabic, vegetable oils, polyalkyleneglycols, petroleum jelly and the like. The pharmaceutical preparations can be produced in a conventional manner and finished dosage forms can be solid dosageforms (e.g. tablets, dragees, suppositories, capsules etc) or liquid dosage forms (e.g. solutions, suspensions, emulsions etc). The pharmaceutical preparations may be subjected to conventional pharmaceutical operations such as sterilization and/or may contain conventional adjuvants such as preservatives, stabilizers, wetting agents, buffers, salts for varying the osmotic pressure etc. They may also contain other therapeutically valuable substances.

The compounds of formula I and their pharmaceutically acceptable acid salts may be used as antitumour agents in a continuous regimen (e.g. daily administration) or a periodic regimen (e.g. monthly administration). In general, the total dosage per treatment will be within the range of about 25 mg/m$^2$–700 mg/m$^2$ (milligrams per square meter of skin area). It will, however, be appreciated that this dosage range is given by way of example only and that it can be varied upwards or downwards depending on factors such as the potency of the particular compound of formula I or salt being administered, the route of administration and the severity of the condition being treated.

The following Examples illustrate the present invention:

EXAMPLE 1

(a) A solution of 1.3 g of (1S)-cis-1,2,3,4,6,11-hexahydro-1,3,5,12-tetrahydroxy-6,11-dioxo-3-(phenylcarbamoyloxy)methylnaphthacene in 100 ml of tetrahydrofuran was cooled to −5° C. and 1.3 g of 2,3,6-trideoxy-4-O-p-nitrobenzoyl-3-trifluoroacetamido-α-L-lyxohexopyranosyl chloride in 10 ml of dichloromethane were added thereto. The mixture was stirred while a solution of 0.65 g of silver trifluoromethanesulphonate in 15 ml of dry diethyl ether was added over a period of 20 minutes. After completion of the addition, a further 1.3 g of the aforementioned chlorosugar in 10 ml of dichloromethane were added and then a further 0.65 g of silver trifluoromethanesulphonate in 15 ml of dry diethyl ether was added over a period of 20 minutes. The mixture was stirred at −5° C. for 30 minutes, then poured into 300 ml of 10% potassium hydrogen carbonate solution and extracted with four 100 ml portions of dichloromethane. The dichloromethane extracts were dried over anhydrous sodium sulphate and evaporated to give a red gum which was purified by column chromatography on silica gel using n-hexane/ethyl acetate (1:1, vol/vol) for the elution. In addition to 400 mg of unreacted dioxonaphthacene starting material, there were obtained 1.16 g of (1S)-cis-1-[(2,3,6-trideoxy-3-trifluoroacetamido-4-O-p-nitrobenzoyl-α-L-lyxohexopyranosyl)oxy]-1,2,3,4,6,11-hexahydro-3,5,12-trihydroxy-6,11-dioxo-3-(phenylcarbamoyloxy)methylnaphthacene in the form of red crystals after crystallization from dichloromethane/diethyl ether.

(b) 1.7 g of the compound obtained according to paragraph (a) were dissolved in a mixture of 100 ml of dichloromethane and 100 ml of methanol and the resulting solution was cooled to 0° C. 0.1M aqueous sodium hydroxide was added dropwise to produce a brown-purple colour and the mixture was stirred at 0° C. for 1.5 hours. The reaction was quenched by the addition of acetic acid to restore the orange colour, and the mixture was diluted with 250 ml of water and extracted with four 100 ml portions of dichloromethane. The combined dichloromethane extracts were dried over anhydrous sodium sulphate and evaporated to a small volume. Addition of diethyl ether while swirling brought about the precipitation of (1S)-cis-1-[(2,3,6-trideoxy-3-trifluoroacetamido-α-L-lyxohexopyranosyl)oxy]-1,2,3,4,6,11-hexahydro-3,5,12-trihydroxy-6,11-dioxo-3-(phenylcarbamoyloxy)methylnaphthacene which, after filtration, was obtained in the form or an orange powder of melting point 160°–170° C.; $[\alpha]_D^{20} = +136.9°$ (c=0.1% in chloroform).

(c) A solution of 680 mg of the compound obtained according to paragraph (b) in 10 ml of tetrahydrofuran was added to 60 ml of an ice-cold 0.1M aqueous sodium hydroxide solution. The mixture was stirred at 0° C. for 45 minutes and then at room temperature for 30 minutes. The solution was adjusted to pH 8–9 by the addition of 0.1M aqueous hydrochloric acid and then repeatedly extracted with dichloromethane containing 10% ethanol until the extracts were virtually colourless. The combined extracts were washed with water, dried over anhydrous sodium sulphate and evaporated to give a red gum. This gum was dissolved in 15 ml of dichloromethane containing 3 ml of methanol and filtered. There were then added 4 ml of 0.25M methanolic hydrogen chloride followed by 250 ml of dry diethyl ether while swirling. The precipitated product was collected by filtration washed with dry diethyl ether and dried in vacuo to give 0.54 g of (1S)-cis-1-[(3-amino-2,3,6-trideoxy]-α-L-lyxohexopyranosyl)oxy]-1,2,3,4,6,11-hexahydro-3,5,12-trihydroxy-6,11-dioxo-3-(phenylcarbamoyloxy)methylnaphthacene hydrochloride in the form of an orange-red powder of melting point 175°–177° C. (decomposition); $[\alpha]_D^{20} = +158.9°$ (c=0.05% in methanol).

The (1S)-cis-1,2,3,4,6,11-hexahydro-1,3,5,12-tetrahydroxy-6,11-dioxo-3-(phenylcarbamoyloxy)methylnaphthacene used as the starting material in paragraph (a) was prepared as follows:

(i) 0.8 g of (1S)-cis-1,2,3,4,6,11-hexahydro-5,12-dihydroxy-3-hydroxymethyl-6,11-dioxo-1,3-naphthacenediyl benzeneboronate was dissolved in 100 ml of pyridine and 0.9 g of phenyl isocyanate was added. The mixture was heated at 60° C. for 45 minutes, cooled and the solvent was removed by evaporation. The residue was taken up in 100 ml of dichloromethane, some colourless insoluble material was removed by filtration, the filtrate was washed with 50 ml of 5M hydrochloric acid and twice with 50 ml of water each time, dried over anhydrous sodium sulphate and evaporated to give crude (1S)-cis-1,2,3,4,6,11-hexahydro-5,12-dihydroxy-6,11-dioxo-3-(phenylcarbamoyloxy)methyl-1,3-naphthacenediyl benzeneboronate in the form of a red solid which was used without further purification.

(ii) The benzeneboronate obtained according to paragraph (i) was dissolved in a mixture of 30 ml of dichloromethane, 30 ml of 2-methyl-2,4-pentanediol and 3 ml of acetic acid and the solution was left to stand at room temperature overnight. The solution was diluted with 100 ml of dichloromethane, washed with three 100 ml portions of water, dried over anhydrous sodium sulphate and evaporated. Trituration of the residue with ethyl acetate/diethyl ether gave 0.82 g of (1S)-cis-1,2,3,4,6,11-hexahydro-1,3,5,12-tetrahydroxy-6,11-dioxo-3-(phenylcarbamoyloxy)methylnaphthacene in the form of red crystals of melting point 225°–226° C.; $[\alpha]_D^{20} = +136.0°$ (c=0.05% in dioxan).

The (1S)-cis-1,2,3,4,6,11-hexahydro-5,12-dihydroxy-3-hydroxymethyl-6,11-dioxo-1,3-naphthacenediyl benzeneboronate used as the starting material in paragraph (i) was prepared according to procedure (A) or (B) described hereinafter:

(A) 2.0 g of (1S)-cis-3-acetoxymethyl-1,2,3,4,6,11-hexahydro-1,3,5,12-tetrahydroxy-6,11-dioxonaphthacene were dissolved in a mixture of 250 ml of dichloromethane and 250 ml of methanol. The mixture was stirred at room temperature and sufficient 0.1M aqueous sodium hydroxide solution was added to maintain a deep purple colour. The mixture was stirred for 5 hours. The reaction was quenched by the addition of acetic acid to restore the orange colour and most of the solvent was removed by evaporation. 100 ml of water were added to the residue and the orange-red precipitate produced was collected by filtration and dried in vacuo. There were obtained 1.7 g of (1S)-cis-1,2,3,4,6,11-hexahydro-1,3,5,12-tetrahydroxy-3-hydroxymethyl-6,11-dioxonaphthacene in the form of orange-red crystals of melting point 212°–214° C.; $[\alpha]_D^{20} = +131.3°$ (c=0.1% in dioxan).

4.0 g of the compound obtained according to the preceding paragraph were suspended in 1000 ml of tetrahydrofuran and treated with 2.5 g of benzeneboronic acid and 0.1 g of acetic acid. The mixture was heated under reflux for 30 minutes, cooled and the solvent was removed by evaporation to give a red residue. After trituration with methanol, there were obtained 4.65 g of (1S)-cis-1,2,3,4,6,11-hexahydro-5,12-dihydroxy-3-hydroxymethyl-6,11-dioxo-1,3-naphthacenediyl benzeneboronate in the form of orange-red crystals of melting point 258°–259° C.; $[\alpha]_D^{20} = +355.0°$ (c=0.1% in dioxan).

(B) 1.0 g of (1S)-cis-3-acetoxymethyl-1,2,3,4,6,11-hexahydro-5,12-dihydroxy-6,11-dioxo-1,3-naphthacenediyl benzeneboronate was dissolved in a mixture of 100 ml of dichloromethane and 100 ml of methanol. The mixture was stirred at room temperature and sufficient 0.1M aqueous sodium hydroxide was added to produce a deep purple colour. The mixture was stirred for 4 hours and then quenched by the addition of acetic acid to restore the orange colour. The solvent was removed by evaporation and the residue was triturated with methanol to give 0.7 g of (1S)-cis-1,2,3,4,6,11-hexahydro-5,12-dihydroxy-3-hydroxymethyl-6,11-dioxo-1,3-naphthacenediyl benzeneboronate in the form of orange-red crystals which were identical with the compound prepared according to procedure (A).

EXAMPLE 2

(a) A solution of 2.0 g of (1S)-cis-3-(4-chlorophenylcarbamoyloxy)methyl-1,2,3,4,6,11-hexahydro-1,3,5,12-tetrahydroxy- 6,11-dioxonaphthacene in 200 ml of tetrahydrofuran and 14 ml of dimethylformamide was cooled to −5° C. and treated with 2.0 g of 2,3,6-trideoxy-4-O-p-nitrobenzoyl-3-trifluoroacetamido-α-L-lyxohexopyranosyl chloride in 20 ml of dichloromethane. Subsequently, 1.0 g of silver trifluoromethanesulphonate in 25 ml of dry diethyl ether was added dropwise over a period of 20 minutes. After completion of this addition, two further additions of the chlorosugar using 2.0 g and 1.0 g, and of silver trifluoro methanesulphonate using 1.0 g and 0.5 g, respectively, were effected under similar conditions. The mixture was then stirred at −5° C. for 30 minutes, subsequently poured into 400 ml of 10% potassium hydrogen carbonate solution and extracted with four 200 ml portions of dichloromethane. The dichloromethane extracts were dried over anhydrous sodium sulphate and evaporated to give a red gum which was purified by column chromatography on silica gel using acetone/dichloromethane (1:5, vol/vol) for the elution. In addition to 575 mg of unreacted dioxonaphthacene starting material, there were obtained 1.51 g of (1S)-cis-3-(4-chlorophenylcarbamoyloxy)methyl-1-[(2,3,6-trideoxy-3-trifluoroacetamido-4-O-p-nitrobenzoyl-α-L-lyxohexopyranosyl)oxy]-1,2,3,6,11-hexahydro-3,5,12-trihydroxy-6,11-dioxonaphthacene in the form of orange-red crystals of melting point 220°–222° C.; $[\alpha]_D^{20} = -60.1°$ (c=0.05% in dioxan).

(b) The compound obtained according to paragraph (a) was treated according to the procedure described in Example 1(b) to give (1S)-cis-3-(4-chlorophenylcarbamoyloxy)methyl-1-[(2,3,6-trideoxy-3-trifluoroacetamido-α-L-lyxohexopyranosyl)oxy]-1,2,3,4,6,11-hexahydro-3,5,12-trihydroxy-6,11-dioxonaphthacene in the form of orange-red crystals which were used without further purification.

(c) The compound obtained according to paragraph (b) was treated according to the procedure described in Example 1(c) to give (1S)-cis-1-[(3-amino-2,3,6-trideoxy-α-L-lyxohexopyranosyl)oxy]-3-(4-chlorophenylcarbamoyloxy)methyl-1,2,3,4,6,11-hexahydro-3,5,12-trihydroxy-6,11-dioxonaphthacene hydrochloride in the form of an orange-red powder of melting point 177°–179° C.; $[\alpha]_D^{20} = +159.9°$ (c=0.05% in methanol).

The (1S)-cis-3-(4-chlorophenylcarbamoyloxy)methyl-1,2,3,4,6,11-hexahydro-1,3,5,12-tetrahydroxy-6,11-dioxonaphthacene used as the starting material in paragraph (a) can be prepared as follows:

(i) 1.0 g of (1S)-cis-1,2,3,4,6,11-hexahydro-5,12-dihydroxy-3-hydroxymethyl-6,11-dioxo-1,3-naphthacenediyl benzeneboronate was reacted with 0.5 g of 4-chlorophenyl isocyanate in 100 ml of pyridine according to the method described in Example 1(i). Analogous working-up gave (1S)-cis- 3-(4-chlorophenylcarbamoyloxy)methyl-1,2,3,4,6,11-hexahydro-5,12-dihydroxy-6,11-dioxo-1,3-naphthacenediyl benzeneboronate in the form of a red solid which was used without further purification.

(ii) The benzeneboronate obtained according to paragraph (i) was treated according to the procedure described in Example 1(ii) to give (1S)-cis-3-(4-chlorophenylcarbamoyloxy)methyl-1,2,3,4,6,11-hexahydro-1,3,5,12-tetrahydroxy-6,11-dioxonaphthacene which was obtained in the form of orange-red crystals of melting point 264°–265° C.; $[\alpha]_D^{20} = +125.1°$ (c=0.05% in dioxan).

EXAMPLE 3

(a) 1.2 g of (1S)-cis-1,2,3,4,6,11-hexahydro-1,3,5,12-tetrahydroxy-3-(4-nitrophenylcarbamoyloxy)methyl-6,11-dioxonaphthacene were treated with 2,3,6-trideoxy-4-O-p-nitrobenzoyl-3-trifluoroacetamido-α-L-lyxohexopyranosyl chloride according to the procedure described in Example 2(a). After chromatography, in addition to 254 mg of unreacted dioxonaphthacene starting material, there were obtained 959 mg of (1S)-cis-1-[(2,3,6-trideoxy-3-trifluoroacetamido-4-O-p-nitrobenzoyl-α-L-lyxohexopyranosyl)oxy]-1,2,3,4,6,11-hexahydro-3,5,12-trihydroxy-3-(4-nitrophenylcarbamoyloxy)methyl-6,11-dioxonaphthacene in the form of orange-red crystals of melting point 208°–210° C.; $[\alpha]_D^{20} = -60.1°$ (c=0.05% in dioxan).

(b) The compound obtained according to paragraph (a) was treated according to the procedure described in Example 1(b) to give (1S)-cis-1-[(2,3,6-trideoxy-3-trifluoroacetamido-α-L-lyxohexopyranosyl)oxy]-1,2,3,4,6,11-hexahydro-3,5,12-trihydroxy-3-(4-nitrophenylcarbamoyloxy)methyl-6,11-dioxonaphthacene in the form of orange-red crystals which were used without further purification.

(c) The compound obtained according to paragraph (b) was treated according to the procedure described in Example 1(c) to give (1S)-cis-1-[(3-amino-2,3,6-trideoxy-α-L-lyxohexopyranosyl)oxy]-1,2,3,4,6,11-hexahydro-3,5,12-trihydroxy-3-(4-nitrophenylcarbamoyloxy)methyl-6,11-dioxonaphthacene hydrochloride in the form of an orange-red powder of melting point 175°–178° C. (decomposition); $[\alpha]_D^{20} = -151.80$ (c=0.05% in methanol).

The (1S)-cis-1,2,3,4,6,11-hexahydro-1,3,5,12-tetrahydroxy-3-(4-nitrophenylcarbamoyloxy)methyl-6,11-dioxonaphthacene used as the starting material in paragraph (a) was prepared as follows:

(i) A solution of 1.0 g of (1S)-cis-1,2,3,4,6,11-hexahydro-5,12-dihydroxy-3-hydroxymethyl-6,11-dioxo-1,3-naphthacenediyl benzeneboronate and 1.0 g of 4-nitrobenzoyl azide in 100 ml of pyridine was heated at 75° C. for 1.25 hours, cooled and the pyridine was then removed by evaporation. The red residue was taken up in 200 ml of dichloromethane, insoluble material was removed by filtration and the solution was washed with 50 ml of 5M hydrochloric acid and with two 100 ml portions of water. After drying over anhydrous sodium sulphate, the solvent was removed by evaporation to give crude (1S)-cis-1,2,3,4,6,11-hexahydro-5,12-dihydroxy-3-(4-nitrophenylcarbamoyloxy)methyl-6 11-dioxo-1,3-naphthacenediyl benzeneboronate in the form of a red gum which was used without further purification.

(ii) The benzeneboronate obtained according to paragraph (i) was treated according to the procedure described in Example 1(ii). 950 mg of (1S)-cis-1,2,3,4,6,11-hexahydro-1,3,5,12-tetrahydroxy-3-(4-nitrophenylcarbamoyloxy)methyl-6,11-dioxonaphthacene were obtained in the form of orange-red crystals of melting point 237°–239° C.; $[\alpha]_D^{20} = +117.4°$ (c=0.05% in dioxan).

EXAMPLE 4

(a) 1.0 g of (1S)-cis-1,2,3,4,6,11-hexahydro-1,3,5, 12-tetrahydroxy-3-(4-methoxyphenylcarbamoyloxy)methyl-6,11-dioxonaphthacene were treated with 2,3,6-trideoxy-4-O-p-nitrobenzoyl-3-trifluoroacetamido-α-L-lyxohexopyranosyl chloride according to the method described in Example 1(a). After chromatography, in addition to 60 mg of unreacted dioxonaphthacene starting material, there were obtained 897 mg of (1S)-cis-1-[(2,3,6-trideoxy-3-trifluoroacetamido-4-O-p-nitrobenzoyl-α-L-lyxohexopyranosyl)oxy]-1,2,3,4,6,11-hexahydro-3,5,12-trihydroxy-3-(4-methoxyphenylcarbamoyloxy)methyl-6,11-dioxonaphthacene in the form of orange-red crystals of melting point 241°–242° C.; $[\alpha]_D^{20} = -69.1°$ (c=0 05% in dioxan).

(b) The compound obtained according to paragraph (a) was treated according to the procedure described in Example 1(b) to give (1S)-cis-1-[(2,3,6-trideoxy-3-trifluoroacetacido-α-L-lyxohexopyranosyl)oxy]-1,2,3,4,6,11-hexahydro-3,5,12-trihydroxy-3-(4-methoxyphenylcarbamoyloxy)methyl-6,11-dioxonaphthacene in the form of orange crystals which were used without further purification.

(c) The compound obtained according to paragraph (b) was treated according to the procedure described in Example 1(c) to give (1S)-cis-1-[(3-amino-2,3,6-trideoxy-α-L-lyxohexopyranosyl)oxy]-1,2,3,4,6,11-hexahydro-3,5,12-trihydroxy-3-(4-methoxyphenylcarbamoyloxy)methyl-6,11-dioxonaphthacene hydrochloride in the form of an orange-red powder of melting point 183°–185° C. (decomposition); $[\alpha]_D^{20} = +152$–9° (c=0.05% in methanol).

The (1S)-cis-1,2,3,4,6,11-hexahydro-1,3,5,12-tetrahydroxy-3-(4-methoxyphenylcarbamoyloxy)methyl-6,11-dioxonaphthancene used as the starting material in paragraph (a) was prepared as follows:

(i) 0.7 g of (1S)-cis-1,2,3,4,6,11-hexahydro-5,12-dihydroxy-3-hydroxymethyl-6,11-dioxo-1,3-naphthacenediyl benzeneboronate was treated with 2.0 g of 4-methoxybenzoyl azide in pyridine according to the procedure described in Example 3(i) to give (1S)-cis-1,2,3,4,6,11-hexahydro-5,12-dihydroxy-3-(4-methoxyphenylcarbamoyloxy)methyl-6,11-dioxo-1,3-naphthacenediyl benzeneboronate in the form of a red gum which was used without further purification.

(ii) The benzeneboronate obtained according to paragraph (i) was treated according to the procedure described in Example 1(ii). 675 mg of (1S)-cis-1,2,3,4,6,11-hexahydro-1,3,5,12-tetrahydroxy-3-(4-methoxyphenylcarbamoyloxy)methyl-6,11-dioxonaphthacene were obtained in the form of orange-red crystals of melting point 196°–197° C.; $[\alpha]_D^{20} = +156.6°$ (c=0.05% in dioxan).

EXAMPLE 5

(a) 1.4 g of (1S)-cis-3-(3-acetoxyphenylcarbamoyloxy)methyl-1,2,3,4,6,11-hexahydro-1,3,5,12-tetrahydroxy-6,11-dioxonaphthacene were treated with 2,3,6-trideoxy-4-O-p-nitrobenzoyl-3-trifluoroacetamido-α-L-lyxohexopyranosyl chloride according to the method described in Example 1(a). After chromatography, in addition to 191 mg of unreacted dioxonaphthacene starting material, there were obtained 806 mg of (1S)-cis-3-(acetoxyphenylcarbamoyloxy)methyl-1-[(2,3,6-trideoxy-3-trifluoroacetamido-4-O-p-nitrobenzoyl-α-L-lyxohexopyranosyl)oxy]-1,2,3,4,6,11-hexahydro-3,5 12-trihydroxy-6,11-dioxonaphthacene in the form of orange-red crystals of melting point 175°–177° C.; $[\alpha]_D^{20} = -62.8°$ (c=0.05% in dioxan).

(b) 0.95 g of the compound obtained according to paragraph (a) was dissolved in a mixture of 100 ml of dichloromethane and 100 ml of methanol. 0.1M aqueous sodium hydroxide solution was added to produce a deep purple colour and the solution was stirred at room temperature for 3.5 hours. Acetic acid was added to restore the orange colour, the mixture was diluted with 250 ml of water and the solution was extracted with four 100 ml portions of dichloromethane. The combined dichloromethane extracts were dried over anhydrous sodium sulphate and evaporated to give a red gum. Trituration with diethyl ether gave 710 mg of (1S)-cis-1-[(2,3,6-trideoxy-3-trifluoroacetamido-α-L-lyxohexopyranosyl)oxy]-1,2,3,4,6,11-hexahydro-3,5,12-trihydro-3-(3-hydroxyphenylcarbamoyloxy)methyl-6,11-dioxonaphthacene in the form of an orange powder.

(c) 690 mg of the compound obtained according to paragraph (b) were treated according to the procedure described in Example 1(c) to give 575 mg of (1S)-cis-1-[(3-amino-2,3,6-trideoxy-α-L-lyxohexopyranosyl)oxy]-1,2,3,4,6,11-hexahydro-3,5,12-trihydroxy-3-(3-hydroxyphenylcarbamoyloxy)methyl-6,11-dioxonaphthacene hydrochloride in the form of an orange-red powder of melting point 178°–180° C. (decomposition); $[\alpha]_D^{20} = +135.5°$ (c=0.05% in methanol).

The (1S)-cis-3-(3-acetoxyphenylcarbamoyloxy)methyl-1,2,3,4,6,11-hexahydro-1,3,5,12-tetrahydroxy-6,11-dioxonaphthacene used as the starting material in paragraph (a) was prepared as follows:

(i) A mixture of 0.6 g of (1S)-cis-1,2,3,4,6,11-hexahydro-5,12-dihydroxy-3-hydroxymethyl-6,11-dioxo-1,3-naphthacenediyl benzeneboronate and 0.6 g of 3-acetoxybenzoyl azide in pyridine was heated at 80° C. for 35 minutes and then a further 0.7 g of 3-acetoxybenzoyl azide was added. Heating was continued for a further 45 minutes, the solvent was removed by evaporation, the residue was taken up in 200 ml of dichloromethane and insoluble material was removed by filtration. The filtrate was washed with 50 ml of 5M hydrochloric acid and with two 50 ml portions of water, dried over anhydrous sodium sulphate and evaporated to give crude (1S)-cis-3-(3-acetoxyphenylcarbamoyloxy)methyl-1,2,3,4,6,11-hexahydro-5,12-dihydroxy-6,11-dioxo-1,3-naphthacenediyl benzeneboronate in the form of an orange-red gum which was used without further purification.

(ii) The benzeneboronate obtained according to paragraph (i) wa treated according to the procedure described in Example 1(ii). 0.71 g of (1S)-cis-3-(3-acetoxyphenylcarbamoyloxy)methyl-1,2,3,4,6,11-hexahydro-1,3,5,12-tetrahydroxy-6,11-dioxonaphthacene was obtained in the form of a red gum which was used without further purification.

EXAMPLE 6

(a) 1.1 g of (1S)-cis-1,2,3,4,6,11-hexahydro-1,3,5,12-tetrahydroxy-3-(methylcarbamoyloxy)methyl-6,11-dioxonaphthacene were treated with 2,3,6-trideoxy-4-O-p-nitrobenzoyl-3-trifluoroacetamido-α-L-lyxohexopyranosyl chloride according to the method described in Example 1(a). After chromatography, (1S)-cis-1-[(2,3,6-trideoxy-3-trifluoroacetamido-4-O-p-nitrobenzoyl-α-L-lyxohexopyranosyl)oxy]-1,2,3,4,6,11-hexahydro-3,5,12-trihydroxy-3-(methylcarbamoyloxy)methyl-6,11-dioxonaphthacene was obtained in the form of a red gum which was used without further purification.

(b) The compound obtained according to paragraph (a) was treated according to the procedure described in Example 1(b) to give (1S)-cis-1-[(2,3,6-trideoxy-3-trifluoroacetamido-α-L-lyxohexopyranosyl)oxy]-1,2,3,4,6,11-hexahydro-3,5,12-trihydroxy-3-(methylcarbamoyloxy)methyl-6,11-dioxonaphthacene in the form of an orange powder which was used without further purification.

(c) 650 mg of the compound obtained according to paragraph (b) was treated according to the procedure described in Example 1(c) to give (1S)-cis-1-[(3-amino-2,3,6-trideoxy-α-L-lyxohexopyranosyl)oxy]-1,2,3,6,11-hexahydro-3,5,12-trihydroxy-3-(methylcarbamoyloxy)-methyl-6,11-dioxonaphthacene hydrochloride in the form of an orange-red powder of melting point 170°–173° C. (decomposition); $[\alpha]_D^{20} = +143.8°$ (c=0.05% in methanol).

The (1S)-cis-1,2,3,4,6,11-hexahydro-1,3,5,12-tetrahydroxy-3-(methylcarbamoyloxy)methyl-6,11-dioxonaphthacene used as the starting material in paragraph (a) was prepared as follows:

(i) A mixture of 1.0 g of (1S)-cis-1,2,3,4,6,11-hexahydro-5,12-dihydroxy-3-hydroxymethyl-6,11-dioxo-1,3-naphthacenediyl benzeneboronate and 2.5 g of methyl isocyanate in 100 ml of pyridine was heated at 70° C. for 3 hours. The solvent was removed by evaporation and the residue was dissolved in dichloromethane and the solution was washed with 50 ml of 5M hydrochloric acid and with two 50 ml portions of water. The solution was dried over anhydrous sodium sulphate and evaporated to give crude (1S)-cis-1,2,3,4,6,11-hexahydro-5,12-dihydroxy-3-(methylcarbamoyloxy)methyl-6,11-dioxo-1,3-naphthacenediyl benzeneboronate in the form of a red gum which was used without further purification.

(ii) The benzeneboronate obtained according to paragraph (i) was treated according to the procedure described in Example 1(ii) to give 0.6 g of (1S)-cis-1,2,3,4,6,11-hexahydro-1,3,5,12-tetrahydroxy-3-(methylcarbamoyloxy)methyl-6,11-dioxonaphthacene in the form of orange-red crystals of melting point 216°–218° C.; $[\alpha]_D^{20} = +130°$ (c=0.05% in dioxan).

EXAMPLE 7

(a) 0.9 g of (1S)-cis-1,2,3,4,6,11-hexahydro-1,3,5,12-tetrahydroxy 3-(2-thienylcarbamoyloxy)methyl-6,11-dioxonaphthacene was treated with two 1.8 g portions of 2,3,6-trideoxy-4-O-p-nitrobenzoyl-3-trifluoroacetamido-α-L-lyxohexopyranosyl chloride according to the procedure described in Example 1(a). After chromatography, in addition to 80 mg of unreacted dioxonaphthacene starting material, there were obtained 800 mg of (1S)-cis-1-[(2,3,6-trideoxy-3-trifluoroacetamido-4-O-p-nitrobenzoyl-α-L-lyxohexopyranosyl)oxy]-1,2,3,4,6,11-hexahydro-3,5,12-trihydroxy-3-(2-thienylcarbamoyloxy)methyl-6,11-dioxonaphthacene in the form of orange red crystals of melting point 210°–212° C.

(b) The compound obtained according to paragraph (a) was treated according to the procedure described in Example 1(b) to give (1S)-cis-1-[(2,3 6-trideoxy-3-trifluoroacetamido-α-L-lyxohexopyranosyl)oxy]-1,2,3,4,6,11-hexahydro-3,5,12-trihydroxy-3-(2-thienylcarbamoyloxy)methyl-6,11-dioxonaphthacene in the form of an orange powder of melting point 154°–157° C.; $[\alpha]_D^{20} = +142.3°$ (c=0.05% in dioxan).

(c) The compound obtained according to paragraph (b) was treated according to the procedure described in Example 1(c) to give (1S)-cis-1-[(3-amino-2,3,6-trideoxy-α-L-lyxohexopyranosyl)oxy]-1,2,3,4,6,11-hexahydro-3,5,12-trihydroxy-3-(2-thienylcarbamoyloxy)-methyl-6,11-dioxonaphthacene hydrochloride in the form of an orange-red powder of melting point 178°–180° C. (decomposition); $[\alpha]_D^{20} = +123.8°$ (c=0.05% in methanol).

The (1S)-cis-1,2,3,4,6,11-hexahydro-1,3,5,12-tetrahydroxy-3-(2-thienylcarbamoyloxy)methyl-6,11-dioxonaphthacene used as the starting material in paragraph (a) was prepared as follows:

(i) A solution of 1.0 g of (1S)-cis-1,2,3,4,6,11-hexahydro-5,12-dihydroxy-3-hydroxymethyl-6,11-dioxo-1,3-naphthacenediyl benzeneboronate and 3.0 g of thiophene-2-carboxylic acid azide in 100 ml of pyridine was heated at 75° C. for 1.5 hours, cooled and left to stand at room temperature for a further 16 hours. The pyridine was removed by evaporation and the red residue was taken up in 200 ml of dichloromethane. Insoluble material was removed by filtration and the solution was washed with 50 ml of 5M hydrochloric acid and the two 100 ml portions of water. After drying over anhydrous sodium sulphate, the solvent was removed by evaporation and the residue was purified by chromatography on silica gel using ethyl acetate/n-hexane for the elution, there being obtained 1.035 g of (1S)-cis-1,2,3,4,6,11-hexahydro-5,12-dihydroxy-3-(2-thienylcarbamoyloxy)methyl-6,11-dioxo-1,3-naphthacenediyl benzeneboronate in the form of orange red crystals of melting point 243°–245° C. (from ethyl acetate); $[\alpha]_D^{20} = +271.5°$ (c=0.05% in dioxan).

(ii) The benzeneboronate obtained according to paragraph (i) was treated according to the procedure described in Example 1(ii) to give (1S)-cis-1,2,3,4,6,11-hexahydro-1,3,5,12-tetrahydroxy-3-(2-thienylcarbamoyloxy)methyl-6,11-dioxonaphthacene in the form of an amorphous orange powder of melting point 144°–146° C.

EXAMPLE 8

(a) A solution of 1.5 g of (1S)-cis 1,2,3,4,6,11-hexahydro-1,3,5,12-tetrahydroxy-6,11-dioxo-3-(phenylcarbamoyloxy)methylnaphthacene in 100 ml of tetrahydrofuran was cooled to −5° C. and 2.5 g of 2,3,6-trideoxy-4-O-p-nitrobenzoyl-3-trifluoroacetamido-α-L-arabinohexopyranosyl chloride in 30 ml of dichloromethane were added thereto. The mixture was stirred while a solution of 1.25 g of silver trifluoromethanesulphonate in 30 ml of dry diethyl ether was added over a period of 30 minutes. After completion of the addition, a further 1.0 g of the aforementioned chlorosugar in 15 ml of dichloromethane was added and then a further 0.5 g of silver trifluoromethanesulphonate in 15 ml of dry diethyl ether was added over a period of 15 minutes. The mixture was stirred at −5° C. for 30 minutes, then poured into 500 ml of 10% potassium hydrogen carbonate solution and extracted with four 150 ml portions of dichloromethane. The dichloromethane extracts were dried over anhydrous sodium sulphate and evaporated to give a red gum which was purified by crystallization from dichloromethane. There were obtained 1.016 g of (1S)-cis-1-[(2,3,6-trideoxy-3-trifluoroacetamido-4-O-p-nitrobenzoyl-α-L-arabinohexopyranosyl)oxy]-1,2,3,4,6,11-hexahydro-3,5,12-trihydroxy-6,11-dioxo-3-(phenylcarbamoyloxy)methylnaphthacene in the form of red crystals of melting point 270°–272° C.; $[\alpha]_D^{20} = +262.9°$ (c=0.05% in dioxan). Chromatography of the mother liquors from the above crystallization on silica gel using ethyl acetate/hexane (1:1) for the elution gave a further 0.16 g of the same product and 0.18 g of unreacted dioxonaphthacene starting material.

(b) 1.05 g of the compound obtained according to paragraph (a) were treated according to the procedure described in Example 1(b) to give 0.79 g of (1S)-cis-1-[(2,3,6-trideoxy-3-trifluoroacetamido-α-L-arabinohexopyranosyl)oxy]-1,2,3,4,6,11-hexahydro-3,5,12-trihydroxy-6,11-dioxo-3-(phenylcarbamoyloxy)methylnaphthacene in the form of orange crystals of melting point 222°–224° C.; $[\alpha]_D^{20} = +186.0°$ (c=0.049% in dioxan).

(c) 0.68 g of the compound obtained according to paragraph (b) was treated according to the procedure described in Example 1(c) to give 0.59 g of (1S)-cis-1-[(3-amino-2,3,6-trideoxy-α-L-arabinohexopyranosyl)oxy]-1,2,3,4,6,11-hexahydro-3,5,12-trihydroxy-6,11-dioxo-3-(phenylcarbamoyloxy)methylnaphthacene hydrochloride in the form of an orange-red powder of melting point 183°–185° C. (decomposition); $[\alpha]_D^{20} = +206.6°$ (c=0.05% in methanol).

EXAMPLE 9

(a) 1.37 g of (1S)-cis-1,2,3,4,6,11-hexahydro-1,3,5,12-tetrahydroxy-6,11-dioxo-3-(phenylcarbanoyloxy)methylnaphthacene were treated with 1.75 g of 2,3,4,6-tetradeoxy-3-trifluoroacetamido-α-L-threohexopyranosyl chloride and 1.25 g of silver trifluoromethanesulphonate according to the procedure described in Example 1(a). After chromatography on silica gel using dichloromethane containing 5% acetone for the elution, in addition to 462 mg of unreacted dioxonaphthacene starting material, there were obtained 585 mg of (1S)-cis-1-[(2,3,4,6-tetradeoxy-3-trifluoroacetamido-α-L-threohexopyranosyl)oxy]1,2,3,4,6,11-hexahydro-3,5,12-trihydroxy-6,11-dioxo-3-(phenylcarbamoyloxy)methylnaphthacene in the form of orange-red crystals of melting point 155°–160° C.; $[\alpha]_D^{20} = +184.6°$ (c=0.05% in dioxan).

(b) 0.60 g of the compound obtained according to paragraph (a) was dissolved in 20 ml of tetrahydrofuran and the solution was added to 60 ml of ice-cold 0.1M aqueous sodium hydroxide. The mixture was stirred at 0° C. for 3 hours and then the pH of the solution was adjusted to 8–9 by the addition of 0.1M aqueous hydrochloric acid. The solution was extracted repeatedly with dichloromethane containing 10% ethanol until the extracts were virtually colourless. The combined extracts were washed with water, dried over anhydrous sodium sulphate and evaporated to give a red gum. This gum was dissolved in 20 ml of dichloromethane, filtered and 4 ml of 0.25M methanolic hydrogen chloride were added. 200 ml of dry diethyl ether were added while swirling to give the product in the form of an orange precipitate. After filtration and drying in vacuo, there were obtained 440 mg of (1S)-cis-1-[(3-amino-2,3,4,6-tetradeoxy-α-L-threohexopyranosyl)oxy]-1,2,3,4,6,11-hexahydro-3,5,12-trihydroxy-6,11-dioxo-3-(phenylcarbamoyloxy)methylnaphthacene hydrochloride in the form of an orange-red powder of melting point 173°–175° C. (decomposition); $[\alpha]_D^{20} = +205.1°$ (c=0.05% in methanol).

EXAMPLE 10

(a) 50 mg of (1S)-cis-1-[(2,3,4,6-tetradeoxy 3-trifluoroacetamido-α-L-threohexopyranosyl)oxy]-1,2,3,4,6,11-hexahydro-3,5,12-trihydroxy-3-hydroxymethyl-6,11-dioxo naphthacene were dissolved in 5 ml of dry pyridine and 100 mg of phenyl isocyanate were added. The mixture was heated at 70° C. for 30 minutes, cooled and the solvent was removed by evaporation. The residue was taken up in 30 ml of dichloromethane, some insoluble material was removed by filtration and the filtrate was purified by chromatography, there being obtained 52 mg of (1S)-cis-1-[(2,3,4,6-tetradeoxy-3-trifluoroacetamido-α-L-threohexopyranosyl)oxy]-1,2,3,4,6,11-hexahydro-3,5,12-trihydroxy-6,11-dioxo-3-(phenylcarbamoyloxy)methylnaphthacene which was identical with the compound obtained according to Example 9(a).

(b) The compound obtained according to paragraph (a) was treated in a manner analogous to that described in Example 9(b) to give (1S)-cis-1-[(3-amino-2,3,4,6-tetradeoxy-α-L-threohexopyranosyl)oxy]-1,2,3,4,6,11-hexahydro-3,5,12-trihydroxy-6,11-dioxo-3-(phenylcarbamoyloxy)methylnaphthacene hydrochloride which was identical with the product obtained according to Example 9(b).

The (1S)-cis-1-[(2,3,4,6-tetradeoxy-3-trifluoroacetamido-α-L-threohexopyranosyl)oxy]-1,2,3,4,6,11-hexahydro- 3,5,12-trihydroxy-3-hydroxymethyl-6,11-dioxonaphthacene used as the starting material in paragraph (a) was prepared as follows:

(i) A solution of 1.0 g of (1S)-cis-3-acetoxymethyl-1,2,3,4,6,11-hexahydro-1,3,5,12-tetrahydroxy-6,11-dioxonaphthacene in 80 ml of tetrahydrofuran was cooled to −5° C. and 0.7 g of 2,3,4,6-tetradeoxy-3-trifluoroacetamido-α-L-threohexopyranosyl chloride in 10 ml of dichloromethane was added. The mixture was stirred while a solution of 0.5 g of silver trifluoromethanesulphonate in 15 ml of tetrahydrofuran was added dropwise over a period of 20 minutes. The mixture was stirred at −5° C. for 0.5 hour, then poured into 300 ml of 10% potassium hydrogen carbonate solution and extracted with four 100 ml portions of dichloromethane. The dichloromethane extracts were dried over anhydrous sodium sulphate and evaporated to give a red gum which was purified by column chromatography on silica gel using ethyl acetate/n-hexane (1:1, vol/vol) for the elution. In addition to 300 mg of unreacted dioxonaphthacene starting material, there were obtained 500 mg of (1S)-cis-3-acetoxymethyl-1-[(2,3,4,6-tetradeoxy-3-trifluoroacetamido-α-L-threohexopyranosyl)oxy]-1,2,3,4,6,11-hexahydro-3,5,12-trihydroxy-6,11-dioxonaphthacene in the form of orange crystals of melting point 210°–212° C.; $[\alpha]_D^{20} = +206.9°$ (c=0.05% in dioxan).

(ii) 0.5 g of the compound obtained according to the preceding paragraph was dissolved in a mixture of 200 ml of dichloromethane and 200 ml of methanol and sufficient 0.1M aqueous sodium hydroxide was added to produce a deep purple colour. The solution was stirred at room temperature for 6 hours and the reaction was quenched by the addition of acetic acid to restore the orange-red colour. The resulting solution was diluted with 250 ml of water and extracted with four 100 ml portions of dichloromethane. The combined dichloromethane extracts were dried over anhydrous sodium sulphate and evaporated to give an orange crystalline solid. Trituration with diethyl ether gave 0.36 g of (1S)-cis-1-[(2,3,4,6-tetradeoxy-3-trifluoroacetamido-α-L-threohexopyranosyl)oxy]-1,2,3,4,6,11-hexahydro-3,5,12-trihydroxy-3-hydroxymethyl-6,11-dioxonaphthacene in the form of orange crystals of melting point 240°–242° C.; $[\alpha]_D^{20} = +228.1°$ (c=0.05% in dioxan).

EXAMPLE 11

(a) 0.5 g of (1S)-cis-1-[(2,3,4,6-tetradeoxy-3-trifluoroacetamido-α-L-threohexopyranosyl)oxy]-1,2,3,4,6,11-hexahydro-3,5,12-trihydroxy-3-hydroxymethyl-6,11-dioxonaphthacene was dissolved in 75 ml of dry pyridine and 1.0 g of pyridine-3-carboxylic acid azide was added. The mixture was heated at 70° C. for 1 hour, cooled and the solvent was removed by evaporation. The red residue was dissolved in 150 ml of dichloromethane and the solution was washed with two 100 ml portions of 2M acetic acid, with 100 ml of water and with 15% potassium hydrogen carbonate solution until effervescence no longer occurred. The solution was dried over anhydrous sodium sulphate, evaporated and the residue was purified by chromatography on silica gel using for the elution firstly 10% acetone in dichloromethane in order to elute impurities and subsequently 5% methanol in ethyl acetate in order to elute the product. The fractions containing the product were evaporated and the red residue was crystallized from methanol/diethyl ether to give 0.25 g of (1S)-cis-1-[(2,3,4,6-tetradeoxy-3-trifluoroacetamido-α-L-threohexopyranosyl)oxy]-1,2,3,4,6,11-hexahydro-3,5,12-trihydroxy-6,11-dioxo-3-(3-pyridylcarbamoyloxy)methylnaphthacene in the form of orange crystals of melting point 165°–167° C. $[\alpha]_D^{20} = +199.5°$ (c=0.05% in dioxan).

(b) 0.5 g of the compound obtained according to paragraph (a) was treated according to the procedure described in Example 9(b) except that 7 ml of 0.25M methanolic hydrogen chloride were added in order to ensure the formation of the dihydrochloride salt. There were obtained 430 mg of (1S)-cis-1-[(3-amino-2,3,4,6-tetradeoxy-α-L-threohexopyranosyl)oxy]-1,2,3,4,6,11-hexahydro-3,5,12-trihydroxy-6,11-dioxo-3-(3-pyridylcarbamoyloxy)methylnaphthacene dihydrochloride in the form of an orange powder of melting point 177°–179° C. (decomposition); $[\alpha]_D^{20} = +146.1°$ (c=0.05% in methanol).

EXAMPLE 12

(a) 0.55 g of (1S)-cis-1-[(2,3,6-trideoxy-3-trifluoroacetamido-4-O-methyl-α-L-lyxohexopyranosyl)oxy]-1,2,3,4,6,11-hexahydro-3,5,12-trihydroxy-3-hydroxymethyl-6,11-dioxonaphthacene was dissolved in 50 ml of dry pyridine and 1.0 g of benzyl isocyanate was added. The mixture was heated at 65° C. for 45 minutes. Then, a further 0.3 g of benzyl isocyanate was added and heating at 65° was continued for a further 1.25 hours. The mixture was then cooled and the pyridine was removed by evaporation. The red residue was purified by chromatography on silica gel using dichloromethane containing 20% acetone for the elution. After precipitation from dichloromethane by the slow addition of hexane, there was obtained 0.5 g of (1S)-cis-3-(benzylcarbamoyloxy)methyl-1-[(2,3,6-trideoxy-3-trifluoroacetamido-4-O-methyl-α-L-lyxohexopyranosyl)oxy]-1,2,3,4,6,11-hexahydro-3,5,12-trihydroxy-6,11-dioxonaphthacene in the form of an orange powder of melting point 110°–115° C.

(b) 0.55 g of the compound obtained according to paragraph (a) was treated according to the procedure described in Example 9(b) to give 0.484 g of (1S)-cis-1-[(3-amino-2,3,6-trideoxy-4-O-methyl-α-L-lyxohexopyranosyl)oxy]-3-(benzylcarbamoyloxy)methyl-1,2,3,4,6,11-hexahydro-3,5,12-trihydroxy-6,11-dioxonaphthacene hydrochloride in the form of an orange-red powder of melting point 167°–170° C. (decomposition); $[\alpha]_D^{20} = +162.3°$ (c=0.05% in methanol).

The (1S)-cis-1-[(2,3,6-trideoxy-3-trifluoroacetamido-4-O-methyl-α-L-lyxohexopyranosyl)oxy]-1,2,3,4,6,11-hexahydro-3,5,12-trihydroxy-3-hydroxymethyl-6,11-dioxonaphacene used as the starting material in paragraph (a) was prepared as follows:

(i) A solution of 4.0 g of (1S)-cis-3-acetoxymethyl-1,2,3,4,6,11-hexahydro-1,3,5,12-tetrahydroxy-6,11-dioxonaphthacene in 320 ml of tetrahydrofuran was treated with 3.2 g of 2,3,6-trideoxy-3-trifluoroacetamido-4-O-methyl-α-L-lyxohexopyranosyl chloride and 2.0 g of silver trifluoromethanesulphonate according to the procedure described in Example 10(i). After purification of the product by chromatography, in addition to 2.0 g of unreacted dioxonaphthacene starting material, there were obtained 2.42 g of (1S)-cis-3-acetoxymethyl-1-[(2,3,6-trideoxy-3-trifluoroacetamido-4-O-methyl-α-L-lyxohexopyranosyl)oxy]-1,2,3,4,6,11-hexahydro-3,5,12-trihydroxy-6,11-dioxonaphthacene in the form of orange crystals of melting point 210°–211° C.; $[\alpha]_D^{20} = +161.2°$ (c=0.05% in dioxan).

(ii) 1.5 g of the compound obtained according to paragraph (i) was treated according to the procedure described in Example 10(ii) to give 1.11 g of (1S)-cis-1-[(2,3,6-trideoxy-3-trifluoroacetamido-4-O-methyl-α-L-lyxohexopyranosyl)oxy-1,2,3,4,6,11-hexahydro-3,5,12-trihydroxy-3-hydroxymethyl-6,11-dioxonaphthacene in the form of orange crystals of melting point 262°–263° C.; $[\alpha]_D^{20} = +181.3°$ (c=0.05% in dioxan).

EXAMPLE 13

(a) 1.0 g of (1S)-cis-1,2,3,4,6,11-hexahydro-1,3,5,12-tetrahydroxy-3-[[2-(methoxycarbonyl)ethyl]carbamoyloxy]-methyl-6,11-dioxonaphthacene was treated with 1.7 g of 2,3,6-trideoxy-4-O-p-nitrobenzoyl-3-trifluoroacetamido-α-L-lyxohexopyranosyl chloride according to the procedure described in Example 1(a). After chromatography, in addition to 0.2 g of unreacted dioxonaphthacene starting material, there was obtained 1.0 g of (1S)-cis-1-[(2,3,6-trideoxy-3-trifluoroacetamido-4-O-p-nitrobenzoyl-α-L-lyxohexopyranosyl)oxy]--1,2,3,4,6,11-hexahydro-3,5,12-trihydroxy-3-[[2-(methoxycarbonyl)ethyl]carbamoyloxy]methyl-6,11-dioxonaphthacene in the form of a red foam which was used without further purification.

(b) 1.0 g of the compound obtained according to paragraph (a) was treated according to the procedure described in Example 1(b) to give 0.55 g of (1S)-cis-1-[(2,3,6-trideoxy-3-trifluoroacetamido-α-L-lyxohexopyranosyl)oxy]-1,2,3,4,6,11-hexahydro-3,5,12-trihydroxy-3-[[2-(methoxycarbonyl)ethyl] carbamoyloxy]-methyl-6,11-dioxonaphthacene in the form of an orange powder of melting point 135°–145° C.; $[\alpha]_D^{20} = +155.3°$ (c=0.05% in dioxan).

(c) 0.5 g of the compound obtained according to paragraph (b) was dissolved in 10 ml of tetrahydrofuran and added to 70 ml of 0.1M aqueous sodium hydroxide. The mixture was stirred at room temperature for 45 minutes and then acidified with 2M hydrochloric acid until the pH of the solution was approximately 7. 175 ml of water were added and the solution was extracted with three 350 ml portions of n-butanol. The combined n-butanol extracts were washed with three 200 ml portions of distilled water and the n-butanol layer was evaporated in vacuo to give an orange solid. This solid was suspended in 25 ml of methanol and 2.5 ml of 0.175M methanolic hydrogen chloride were added. After the majority of the solid had dissolved, the solution was filtered and concentrated to 15 ml. 250 ml of anhydrous diethyl ether were added while swirling and the precipitated product was filtered off and dried in vacuo, there being obtained 0.25 g of (1S)-cis-[(3-amino-2,3,6-trideoxy-α-L-lyxohexopyranosyl)oxy]-3-[(2-carboxyethyl)carbamoyloxy]methyl-1,2,3,4,6,11-hexahydro-3,5,12-trihydroxy-6,11-dioxonaphthacene hydrochloride in the form of an orange-red powder of melting point 155°–163° C. (decomposition); $[\alpha]_D^{20} = +125.6°$ (c=0.05% in methanol).

The (1S)-cis-1,2,3,4,6,11-hexahydro-1,3,5,12-tetrahydroxy- 3-[[2-(methoxycarbonyl)ethyl]carbamoyloxy]-methyl-6,11-dioxonaphthacene used as the starting material in paragraph (a) was prepared as follows:

A solution of 1.0 g of (1S)-cis-1,2,3,4,6,11-hexahydro-5,12-dihydroxy-3-hydroxymethyl-6,11-dioxo-1,3-naphthacenediyl benzeneboronate and 0.88 g of methyl 3-isocyanatopropionate in 12 ml of dry pyridine was stirred at room temperature for 4 days. The pyridine was removed by evaporation under reduced pressure and the red residue was ii dissolved in 60 ml of dichloromethane, 1.33 ml of 2-methyl-2,4-pentanediol and 0.66 ml of glacial acetic acid. The mixture was then stirred at room temperature for 40 hours. The solution was diluted with 500 ml of dichloromethane and washed with four 150 ml portions of water. After drying over anhydrous sodium sulphate, the solvent was removed by evaporation to give a red crystalline product. Trituration with diethyl ether gave 0.84 g of (1S)-cis-1,2,3,4,6,11-hexahydro-1,3,5,12-tetrahydroxy-3-[[2-(methoxycarbonyl)ethyl]carbamoyloxy]methyl-6,11-dioxonaphthacene in the form of orange-red crystals of melting point 146°–149° C.; $[\alpha]_D^{20} = +113.9°$ (c=0.05% in dioxan). 113.9° (c=0.05% in dioxan).

EXAMPLE 14

(a) 0.526 g of (1S)-cis-1,2,3,4,6,11-hexahydro-1,3,5,12-tetrahydroxy-3-[[2-(methoxycarbonyl)ethyl]carbamoyloxy] methyl-6,11-dioxonaphthacene was treated with 0.9 g of 3-chloroacetamido-2,3,6-trideoxy-4-O-p-nitrobenzoyl-α-L-lyxohexopyranosyl chloride according to the procedure described in Example 1(a). After chromatography, in addition to 0.146 g of unreacted dioxonaphthacene starting material, there was obtained 0.355 g of (1S)-cis-1-[(3-chloroacetamido-2,3,6-trideoxy-4-O-p-nitrobenzoyl-α-L-lyxohexopyranosyl)oxy-1,2,3,4,6,11-hexahydro-3,5,12-trihydroxy-3-[[2-(methoxycarbonyl)ethyl]carbamoyloxy]methyl-6,11-dioxonaphthacene in the form of an orange powder which was used without further purification.

(b) 0.35 g of the compound obtained according to paragraph (a) was treated according to the procedure described in Example 1(b) to give 0.177 g of (1S)-cis-1-[(3-chloroacetamido-2,3,6-trideoxy-α-L-lyxohexopyranosyl)oxy]-1,2,3,4,6,11-hexahydro-3,5,12-trideoxy-3-[[2-(methoxycarbonyl)ethyl]carbamoyloxy]-methyl-6,11-dioxonaphthacene in the form of an orange powder of melting point 135°–145° C.; $[\alpha]_D^{20} = +135.9°$ (c=0.05% in dioxan).

(c) 0.1 g of the compound obtained according to paragraph (b) was suspended in 100 ml of ethanol containing 50 mg of thiourea. The mixture was heated under reflux for 26 hours, then cooled and the solvent was removed by evaporation. The residue was dissolved in 100 ml of water and the pH was adjusted to 3 with hydrochloric acid. The solution was extracted with three 50 ml portions of dichloromethane and these extracts were discarded. The pH of the aqueous phase was adjusted to neutrality by the addition of dilute sodium bicarbonate solution and then extracted with three 50 ml portions of dichloromethane containing 10% methanol. The combined extracts were dried over anhydrous sodium sulphate and evaporated. The residue was dissolved in 20 ml of methanol and the solution was filtered. The filtrate was treated with 1 ml of 0.175M methanolic hydrogen chloride and then 250 ml of dry diethyl ether and 100 ml of n-hexane were added. The precipitated product was filtered off and dried in vacuo, there being obtained 57 mg of (1S)-cis-[(3-amino-2,3,6-trideoxy-α-L-lyxohexopyranosyl)oxy]-1,2,3,4,6,11-hexahydro-3,5,12-trihydroxy-3-[[2-(methoxcarbonyl)ethyl]carbamoyloxy]methyl-6,11-dioxonaphthacene hydrochloride in the form of an orange powder of melting point 145°–150° C. (decomposition); $[\alpha]_D^{20} = +146.8°$ (c=0.05% in methanol).

EXAMPLE 15

10 mg of (1S)-cis-[(3-amino-2,3,6-trideoxy-α-L-lyxohexopyranosyl)oxy]-3-[(2-carboxyethyl)carbamoyloxy]methyl-1,2,3,4,6,11-hexahydro-3,5,12-trihydroxy-6,11-dioxonaphthacene hydrochloride were dissolved in 5 ml of methanol and 0.5 ml of 0.175M methanolic hydrogen chloride was added. The solution was left to stand at 4° C. in the dark for 48 hours and subsequently poured into 50 ml of water. The acidic aqueous solution was extracted with two 20 ml portions of dichloromethane and these extracts were discarded. The aqueous solution was adjusted to neutral pH by the addition of sodium hydrogen carbonate and then extracted with three 30 ml portions of dichloromethane containing 10% methanol. The combined extracts were dried over anhydrous sodium sulphate and evaporated to give a red residue which was dissoved in 2 ml of methanol and filtered. The filtrate was treated with 0.1 ml of 0.175M methanolic hydrogen chloride and then 25 ml of diethyl ether and 10 ml of n-hexane were added. The precipitated product was filtered off and dried in vacuo to give 6 mg of (1S)-cis-1-[(3-amino-2,3,6-trideoxy-α-L-lyx-ohexopyranosyl)oxy]-1,2,3,4,6,11-hexahydro-3,5,12-trihydroxy-3-[[2-(methoxycarbonyl)ethyl]carbamoyloxy]methyl-6,11-dioxonaphthacene hydrochloride in the form of an orange powder which was identical with the product obtained according to Example 14.

EXAMPLE 16

(a) 0.405 g of (1S)-cis-1,2,3,4,6,11-hexahydro-1,3,5,12-tetrahydroxy-6,11-dioxo-3-[[2-(propylcarbamoyl)ethyl]carbamoyloxy]methylnaphthacene in a mixture of 25 ml of tetrahydrofuran and 15 ml of dioxan was treated with a total of 0.7 g of 2,3,6-trideoxy-4-O-p-nitrobenzoyl-3-trifluoroacetamido-α-L-lyxohex-opyranosyl chloride according to the procedure described in Example 1(a). After chromatography, in addition to 0.12 g of unreacted dioxonaphthacene starting material, there was obtained 0.291 g of (tb 1S)-cis-1-[-(2,3,6-trideoxy-3-trifluoroacetamido-4-O-p-nitrobenz-oyl-α-L-lyxohexopyranosyl)oxy]-1,2,3,4,6,11-hexahydro-3,5,12-trihydroxy-6,11-dioxo-3-[[2-(propylcarbamoyl)ethyl]carbamoyloxy]methylnaphthacene in the form of an orange-red gum.

(b) The compound obtained according to paragraph (a) was treated according to the procedure described in Example 1(b) to give (1S)-cis-1-[(2,3,6-trideoxy-3-trifluoroacetamido-α-L-lyxohexopyranosyl)oxy]-1,2,3,4,6,11-hexahydro-3,5,12-trihydroxy-6,11-dioxo-3-[[2-(propylcarbamoyl)ethyl]carbamoyloxy]methylnaphthacene in the form of an orange powder of melting point 127°–136° C. (decomposition); $[\alpha]_D^{20} = +133.3°$ (c=0.05% in dioxan).

(c) The compound obtained according to paragraph (b) was treated according to the procedure described in Example 1(c) to give (1S)-cis-1-[(3-amino-2,3,6-trideoxy-α-L-lyxohexopyranosyl)oxy]-1,2,3,4,6,11-hexahydro-3,5,12-trihydroxy-6,11-dioxo-3-[[2-(propylcarbamoyl)ethyl]carbamoyloxy]methylnaphthacene hydrochloride in the form of an orange-red powder of melting point 152°–162° C. (decomposition): $[\alpha]_D^{20} = +169.5°$ (c=0.05% in methanol).

The (1S)-cis-1,2,3,4,6,11-hexahydro-1,3,5,12-tetrahydroxy-6,11-dioxo-3-[[2-(propylcarbamoyl)ethyl]carbamoyloxy]methylnaphthacene used as the starting material in paragraph (a) was prepared as follows:

(i) 0.2 g of (1S)-cis-1,2,3,4,6,11-hexahydro-1,3,5,12-tetrahydroxy-3-[[2-(methoxycarbonyl)ethyl]carbamoyloxy]methyl-6,11-dioxonaphthacene was heated at 80° C. for 2 hours with 0.05 g of benzeneboronic acid in 60 ml of tetrahydrofuran containing 4 drops of glacial acetic acid. The solvent was removed by evaporation to give a residual volume of 8 ml and 32 ml of 0.1M aqueous sodium hydroxide were added. The mixture was stirred at room temperature for 2.5 hours and then acidified to pH 2 by the dropwise addition of concentrated hydrochloric acid. The mixture was diluted with 200 ml of water and the product was extracted with 100 ml of n-butanol and then with 50 ml of n-butanol. The n-butanol extracts were combined and evaporated. The red crystalline residue was triturated with diethyl ether and filtered to give 0.2 g of (1S)-cis-3-[(2-carboxyethyl)-carbamoyloxy]methyl-1,2,3,4,6,11-hexahydro-5,12-dihydroxy-6,11,dioxo-1,3-naphthacenediyl benzeneboronate in the form of an orange powder which was used in the next step without further purification.

(ii) 0.2 g of the compound obtained according to paragraph (i) was suspended in 44 ml of dichloromethane and 0.2 g of oxalyl chloride and 2 drops of dimethylformamide were added. The mixture was stirred at room temperature for 2 hours with the exclusion of moisture, there being obtained a red solution. This solution was cooled to 0° C. and 0.4 g of n-propylamine was added. After 2.5 hours, the solution was diluted with 100 ml of dichloromethane and the resulting solution was washed with 50 ml of 10% hydrochloric acid and then with 50 ml of water. After drying over anhydrous sodium sulphate, the solution was concentrated to 20 ml and 2 ml of 2-methyl-2,4-pentanediol and 5 drops of glacial acetic acid were added. The solution was left to stand at room temperature for 52 hours and was then diluted with 100 ml of dichloromethane, washed with four 50 ml portions of water, dried over anhydrous sodium sulphate and evaporated to give a red crystalline solid. Trituration with diethyl ether gave 0.14 g of (1S)-cis-1,2,3,4,6,11--hexahydro-1,3,5,12-tetrahydroxy-6,11-dioxo-3-[[2-(propylcarbamoyl)ethyl]carbamoyloxy]ethylnaphthacene in the form of orange-red crystals of melting point 120°–125° C.; $[\alpha]_D^{20} = +86.9°$ (c=0.05% in dioxan).

EXAMPLE 17

(a) 0.5 g of (1S)-cis-1,2,3,4,6,11-hexahydro-1,3,5,12-tetrahydroxy-6,11-dioxo-3-[[2-(propylcarbamoyl)ethyl]carbamoyloxy]methylnaphthacene was dissolved in a mixture of 30 ml of dry tetrahydrofuran and 15 ml of dioxan and the solution was treated with a total of 1.0 g of 2,3,6-trideoxy-4-O-p-nitrobenzoyl-3-trifluoroacetamido-α-L-arabinohexopyranosyl chloride according to the procedure described in Example 8(a). After chromatography on silica gel using for the elution ethyl acetate followed by ethyl acetate containing 5% methanol, in addition to 0.165 g of unreacted dioxonaphthacene starting material, there was obtained 0.173 g of a mixture of (1S)-cis-1[(2,3,6-trideoxy-3-trifluoroacetamido-4-O-p-nitrobenzoyl-α-L-arabinohexopyranosyl)oxy]-1,2,3,4,6,11-hexahydro-3,5,12-trihydroxy-6,11-dioxo-3-[[2-(propylcarbamoyl)ethyl]carbamoyloxy]methylnaphthacene and the corresponding β-isomer.

(b) The mixture of glycosides obtained according to paragraph (a) was treated according to the procedure described in Example 1(b) to give a mixture of the corresponding hydroxy glycosides. The mixture was separated by chromatography on silica gel using ethyl acetate for the elution, there being obtained (1S)-cis-1-[(2,3,6-trideoxy-3-trifluoroacetamido-α-L-arabinohexopyranosyl)oxy]-1,2,3,4,6,11-hexahydro-3,5,12-trihydroxy-6,11-dioxo-3-[[2-(propylcarbamoyl)ethyl]carbamoyloxy]methylnaphthacene in the form of orange crystals of melting point 232°–235° C. (decomposition); $[\alpha]_D^{20} = +186.0°$ (c=0.05% in dioxan); and (1S)-cis-1-[(2,3,6-trideoxy-3-trifluoroacetamido-β-L-arabinohexopyranosyl)oxy]-1,2,3,4,6,11-hexahydro-3,5,12-trihydroxy-6,11-dioxo-3-[[2-(propylcarbamoyl)ethyl]carbamoyloxy]methylnaphthacene in the form of orange crystals of melting point 200°–209° C. (decomposition); $[\alpha]_D^{20} = +202.0°$ (c=0.05% in dioxan).

(c) The α-glycoside obtained according to paragraph (b) was treated according to the procedure described in Example 1(c) to give (1S)-cis-1-[(3-amino-2,3,6-trideoxy-α-L-arabinohexopyranosyl)oxy]-1,2,3,4,6,11-hexahydro-3,5,12-trihydroxy-6,11-dioxo-3-[[2-(propylcarbamoyl)ethyl]carbamoyloxy]methylnaphthacene hydrochloride in the form of an orange powder of melting point 158°–165° C. (decomposition); $[\alpha]_D^{20} = +198.8°$ (c=0.05% in methanol).

EXAMPLE 18

(a) A solution of 690 mg of (1S)-cis-1,2,3,4,6,11-hexahydro-1,3,5,12-tetrahydroxy-6,11-dioxo-3-[1(R)-(phenylcarbamoyloxy)ethyl]naphthacene in 69 ml of tetrahydrofuran was stirred at −2° C. in a nitrogen atmosphere and solutions of 698 mg of 2,3,6-trideoxy-4-O-p-nitrobenzoyl-3-trifluoroacetamido-α-L-lyxohexopyranosyl chloride in 11.5 ml of tetrahydrofuran and 614 mg of silver trifluoromethanesulphonate in 19 ml of diethyl ether were added simultaneously over a period of 1 hour. After stirring the mixture for a further 1 hour at −2° C., a further 698 mg of the aforementioned chlorosugar in 11.5 ml of tetrahydrofuran and a further 614 mg of silver trifluoromethanesulphonate in 19 ml of diethyl ether were added to the mixture over a period of 30 minutes. The mixture was stirred at −2° C. for a further 2.5 hours and was then poured into a mixture of 365 ml of 10% potassium hydrogen carbonate solution and 154 ml of ethyl acetate. The mixture was filtered, the filtrate was transferred into a separating funnel and the layers were separated. The organic extract was washed with two 518 ml portion of water, dried over anhydrous sodium sulphate and evaporated to give a red oil. This oil was purified by chromatography on a column of 200 g of silica gel using for the elution 1.4 l of ethyl acetate/60°–80° C. petroleum ether (1:2, vol/vol) and 300 ml of ethyl acetate/60° C.–80° C. petroleum ether (2:1, vol/vol). There were obtained 710 mg of (1S)-cis-1-[(2,3,6-trideoxy-3-trifluoroacetamido-4-O-p-nitrobenzoyl-α-L-lyxohexopyranosyl)oxy]-1,2,3,4,6,11-hexahydro-3,5,12-trihydroxy-6,11-dioxo-3-[1(R)-(phenylcarbamoyloxy)ethyl]naphthacene in the form of bright orange crystals of melting point 198°–204° C.; $[\alpha]_D^{20} = 0°$ (c=0.1% in dioxan) after crystallization from dichloromethane.

(b) 690 mg of the compound obtained according to paragraph (a) were dissolved in 5 ml of dichloromethane and the solution was diluted with 525 ml of methanol. The resulting solution was cooled to 0° C. and 8.5 ml of 0.1M aqueous sodium hydroxide were added. The deep purple mixture was stirred at 0° C. for 30 minutes and then glacial acetic acid was added dropwise until the solution became bright red. The solution was concentrated to about 100 ml in vacuo, then poured into 900 ml of water and extracted with two 200 ml portions of ethyl acetate. The combined extracts were dried over anhydrous sodium sulphate and evaporated. The crude product was purified by chromatography on a column of 125 g of silica gel using for the elution 1.5 l of dichloromethane, 1 l of acetone/dichloromethane (5:95, vol/vol) and 1 l of acetone/dichloromethane (10:90, vol/vol). There were obtained 240 mg of (1S)-cis-1-[(2,3,6-trideoxy-3-trifluoroacetamido-α-L-lyxohexopyranosyl)oxy]-1,2,3,4,6,11-hexahydro-3,5,12-trihydroxy-6,11-dioxo-3-[1(R)-(phenylcarbamoyloxy)ethyl]naphthacene in the form of a bright red solid of melting point 158°–162° C.; $[\alpha]_D^{20} = +216$ (c=0.1% in dioxan).

(c) A solution of 350 mg of the compound obtained according to paragraph (b) in 7 ml of tetrahydrofuran was added to 55 ml of 0.1M aqueous sodium hydroxide and the deep purple mixture was stirred at room temperature under nitrogen for 30 minutes. The solution was adjusted to pH 8 by the addition of 5M hydrochloric acid and the mixture was extracted with five 80 ml portions of dichloromethane. The combined extracts were washed with 80 ml of water, dried over anhydrous sodium sulphate and evaporated to give a red gum. This gum was dissolved in a mixture of 10 ml of dichloromethane and 1 ml of methanol. 2.1 ml of 0.25M methanolic hydrogen chloride and subsequently 63 ml of diethyl ether were added. The mixture was left to stand at 0° C. overnight. The product was filtered off, washed with diethyl ether and dried in vacuo, there being obtained 215 mg of (1S)-cis-1-[(3-amino-2,3,6-trideoxy-α-L-lyxohexopyranosyl)oxy]-1,2,3,4,6,11-hexahydro-3,5,12-trihydroxy-6,11-dioxo-3-[1(R)-(phenylcarbamoyloxy)ethyl]naphthacene hydrochloride in the form of a bright orange powder of melting point 169°–171° C.; $[\alpha]_D^{20} = +217°$ (c=0.1% in methanol).

The (1S)-cis-1,2,3,4,6,11-hexahydro-1,3,5,12-tetrahydroxy-6,11-dioxo-3-[1(R)-(phenylcarbamoyloxy)ethyl]naphthacene used as the starting material in paragraph (a) was prepared as follows:

(i) 0.70 g of (1S)-cis-1,2,3,4,6,11-hexahydro-5,12-dihydroxy-3-[1(R)-(hydroxy)ethyl]-6,11-dioxo-1,3-naphthacenediyl benzeneboronate were dissolved in 80 ml of pyridine and 510 mg of phenyl isocyanate were added. The mixture was heated at 60° C. for 3 hours, cooled and the solvent was removed by evaporation. The residue was taken up in 16 ml of dichloromethane, some colourless insoluble material was removed by filtration and the filtrate was diluted with a further 144 ml of dichloromethane. The resulting solution was washed with 80 ml of 2M hydrochloric acid and 80 ml of water, dried over anhydrous sodium sulphate and evaporated to give 900 mg of (1S)-cis-1,2,3,4,6,11-hexahydro-5,12-dihydroxy-6,11-dioxo-3-[1(R)-(phenylcarbamoyloxy)ethyl]-1,3-naphthacenediyl benzeneboronate in the form of a red solid which was used without further purification.

(ii) The benzeneboronate obtained according to paragraph (i) was dissolved in a mixture of 70 ml of dichloromethane, 13 ml of 2-methyl-2,4-pentanediol and 3.5 ml of glacial acetic acid and the solution was heated under reflux for 2.5 hours. The solution was then cooled and washed with four 170 ml portions of water, dried over anhydrous sodium sulphate and evaporated. The residue was triturated with 20 ml of diethyl ether and filtered, there being obtained 610 mg of (1S)-cis-1,2,3,4,6,11-hexahydro-1,3,5,12-tetrahydroxy-6,11-dioxo-3-[1(R)-(phenylcarbamoyloxy)ethyl]naphthacene in the form of red crystals of melting point 229.5°–234° C.; $[\alpha]_D^{20} = +205°$ (c=0.1% in dioxan).

The (1S)-cis-1,2,3,4,6,11-hexahydro-5,12-dihydroxy-3-[1(R)-(hydroxy)ethyl]-6,11-dioxo-1,3-naphthacenediyl benzeneboronate used as the starting material in paragraph (i) was prepared as follows:

A solution of 10.0 g of (S)-3'-acetyl-1',2',3',4'-tetrahydro-3'-hydroxy-5',8'-dimethoxyspiro[1,3-dithiolane-2,1'-naphthalene] in 250 ml of dry tetrahydrofuran was cooled to −78° C. and a solution of 1.12 g of lithium aluminium hydride in 75 ml of diethyl ether was added over a period of a few minutes. The mixture was stirred at −78° C. under nitrogen for 30 minutes and then a further 1.12 g of lithium aluminium hydride in 75 ml of diethyl ether were added. After a total reaction time of 45 minutes, 250 ml of 2M hydrochloric acid were added cautiously to the mixture and then 750 ml of water were added. The mixture was extracted with three 600 ml portions of dichloromethane and the combined extracts were washed with 300 ml of water, dried over magnesium sulphate and evaporated to give (3'S)-1',2',3',4'-tetrahydro-3'-hydroxy-3'-[1-(hydroxy)ethyl]-5', 8'-dimethoxyspiro[1,3-dithiolane-2,1'-naphthalene] is a mixture of isomers in the form of a colourless gum which was used without further purification.

The product obtained according to the preceding paragraph was dissolved in 100 ml of pyridine and 15 ml of acetic anhydride were added to the solution. The mixture was left to stand at room temperature overnight. 200 g of ice and then 200 ml of 6M hydrochloric acid were added to the mixture. The resulting mixture was then extracted with three 200 ml portions of dichloromethane. The combined extracts were washed with 200 ml of 2M hydrochloric acid and 200 ml of water, dried over magnesium sulphate and evaporated to give 11.6 g of (3'S)-3'-[1-(acetoxy)ethyl]-1,2,3,4-tetrahydro-3'-hydroxy-5',8'-dimethoxyspiro[1,3-dithiolane-2,1'-naphthacene] as a mixture of isomers in the form of a colourless gum which was used without further purification.

The product obtained according to the preceding paragraph was dissolved in 115 ml of tetrahydrofuran and the solution was added over a period of 10 minutes to a stirred suspension of 36.7 g of mercuric oxide and 36.7 g of mercuric chloride in mixture of 1.15 l of methanol and 100 ml of water. The mixture was stirred at room temperature for 1.75 hours and then concentrated in vacuo to about half of its volume. The resulting mixture was diluted with 1.57 l of dichloromethane and then filtered. The filtrate was washed with three 1 l portions of water, dried over magnesium sulphate and evaporated to give 8.2 g of (3S)-3-[1-(acetoxy)ethyl]-1,2,3,4-tetrahydro-3-hydroxy-5,8-dimethoxy-1-oxo-naphthalene as a mixture of isomers in the form of a colourless oil which was used without further purification.

The product obtained according to the preceding paragraph was dissolved in 425 ml of tetrahydrofuran and 1.9 g of sodium borohydride were added to the solution. The mixture was stirred at room temperature under nitrogen for 2 hours. A further 1.9 g of sodium borohydride were added to the mixture and stirring was continued for a further 1 hour. 160 ml of 2M hydrochloric acid were added gradually to the mixture, which was then extracted with three 160 ml portions of dichloromethane. The combined extracts were washed with 50 ml of water, dried over magnesium sulphate and evaporated. The residue was dissolved in 500 ml of toluene and 4.56 g of benzeneboronic acid, 0.16 g of p-toluenesulphonic acid and 0.5 ml of glacial acetic acid were added. The mixture was stirred at room temperature under nitrogen overnight and then washed with two 100 ml portions of 10% potassium hydrogen carbonate solution, dried over magnesium sulphate and evaporated to give a colourless oil weighing 9.5 g. The crude product obtained was dissolved in 100 ml of diethyl ether and the mixture was stirred at room temperature for 1 hour. After filtration, there were obtained 4.07 g of (1S)-cis-3-[1(R)-(acetoxy)ethyl]-1,2,3,4-tetrahydro-5,8-dimethoxy-1,3-naphthacenediyl benzeneboronate in the form of white crystals of melting point 176°–179° C.; $[\alpha]_D^{20} = +65.5°$ (c=0.1% in chloroform). The mother liquor was concentrated to 20 ml and filtered to give a second crop weighing 2.10 g. Evaporation of the second mother liquor gave 3.4 g of residue which, after partial separation by column chromatography and subsequent fractional crystallization gave (1S)-cis-3-[(1S)-(acetoxy)ethyl]-1,2,3,4-tetrahydro-5,8-dimethoxy-1,3-naphthacenediyl benzeneboronate in the form of white crystals of melting point 148°–149° C.; $[\alpha]_D^{20} = 22.8°$ (c=0.1% in chloroform).

A solution of 11.94 g of ammonium ceric nitrate in 200 ml of water was added over a period of 5 minutes to a stirred solution of 4.32 g of the foregoing (1S)-cis-3-[(1R)-(acetoxy)ethyl]- 1,2,3,4-tetrahydro-5,8-dimethoxy-1,3-naphthacenediyl benzeneboronate in 200 ml of acetonitrile. The mixture was stirred at room temperature for a further 5 minutes and then poured into 1 l of water. The resulting mixture was extracted with four 270 ml portions of dichloromethane and the combined extracts were washed with 270 ml of water, dried over magnesium sulphate and evaporated to give (1S)-cis-3-[(1R)-(acetoxy)ethyl]-1,2,3,4,5,8-hexahydro-5,8-dioxo-1,3-naphthalenediyl benzeneboronate in the form of a yellow oil which was used without further purification.

2.40 g of trans-1,2-diacetoxy-1,2-dihydrobenzocyclobutene were added to a solution of the benzeneboronate prepared according to the preceding paragraph in 214 ml of xylene and the mixture was heated at 140° C. under a nitrogen atmosphere for 3 hours. The solution was cooled and the solvent was removed by evaporation to give a yellow crystalline product which was washed with diethyl ether and filtered, there being obtained 3.6 g of (1S)-cis-3-[(1R)-(acetoxy)ethyl]-1,2,3,4,5,12-hexahydro-5,12-dioxo-1,3-naphthacenediyl benzeneboronate in the form of yellow crystals of melting point 175°–184° C.; $[\alpha]_D^{20} = +147.5°$ (c=0.1% in chloroform).

3.6 g of the compound obtained according to the preceding paragraph were dissolved in a mixture of 175 ml of dry pyridine and 90 ml of acetic anhydride. 175 mg of 10% palladium-on-carbon were added and the mixture was hydrogenated at room temperature and atmospheric pressure for 1 hour. The catalyst was removed by filtration and the filter cake was washed with dichloromethane. The combined filtrates were evaporated and the residue was triturated with 50 ml of diethyl ether and filtered to give 3.71 g of (1S)-cis-5,12-diacetoxy-3-[(1R)-(acetoxy)ethyl]-1,2,3,4-tetrahydro-1,3-naphthacenediyl benzeneboronate in the form of a pale brown solid of melting point 256°–259° C.

The compound prepared according to the preceding paragraph was dissolved in a mixture of 216 ml of glacial acetic acid and 68 ml of acetic anhydride. 2.88 g of finely ground chromium trioxide were added and the mixture was stirred at room temperature for 18 hours. The mixture was poured into 620 ml of water and the resulting suspension was extracted with four 320 ml portions of dichloromethane. The combined extracts were washed with four 450 ml portions of water, dried over magnesium sulphate and evaporated. The residue was triturated with 50 ml of diethyl ether and filtered, there being obtained 1.77 g of (1S)-cis-5,12-diacetoxy-3-[(1R)-(acetoxy)ethyl]-1,2,3,4,6,11-hexahydro-6,11-dioxo-1,3-naphthacenediyl benzeneboronate in the form of a pale yellow solid of melting point 221°–223.5° C.

A solution of the compound obtained according to the preceding paragraph in 340 ml of dichloromethane was cooled to −78° C. A solution of 7 g of boron trichloride in 28 ml of dichloromethane was added and the mixture was stirred and allowed to warm to 0° C. over a period of 2.5 hours. The mixture was poured into 340 ml of ice-cold 2M hydrochloric acid and the layers were separated. The aqueous layer was extracted with two 280 ml portions of dichloromethane and the combined organic solutions were washed with two 250 ml portions of water, dried over magnesium sulphate and evaporated to give 1.7 g of crude (1S)-cis-3-[(1R)-(acetoxy)ethyl]-1,2,3,4,6,11-hexahydro-5,12-dihydroxy-6,11-dioxo-1,3-naphthacenediyl benzeneboronate in the form of a red solid which was used without further purification.

1.2 g of the compound prepared according to the preceding paragraph were dissolved in a mixture of 120 ml of dichloromethane and 120 ml of methanol. 48 ml of 0.1M aqueous sodium hydroxide were added and the resulting deep purple solution was heated under reflux for 3 hours. The mixture was allowed to cool and glacial acetic acid was added until the solution became bright red. The solution was poured into 480 ml of water and the resulting mixture was extracted with two 240 ml portions of dichloromethane. The combined extracts were washed with 360 ml of water, dried over anhydrous sodium sulphate and evaporated to give 0.70 g of (1S)-cis-1,2,3,4,6,11-hexahydro-5,12-dihydroxy-3-[1(R)-(hydroxy)ethyl]-6,11-dioxo-1,3-naphthacenediyl benzeneboronate in the form of a red gum which was used without further purification.

EXAMPLE 19

(a) A solution of 489 mg of (1S)-cis-1,2,3,4,6,11-hexahydro-1,3,5,12-tetrahydroxy-6,11-dioxo-3-[1(R)-(phenylcarbamoyloxy)ethyl]naphthacene in 50 ml of tetrahydrofuran was stirred at −2° C. in a nitrogen atmosphere and solutions of 492 mg of 2,3,6-trideoxy-4-O-p-nitrobenzoyl-3-trifluoroacetamido-α-L-arabinohexopyranosyl chloride in 12 ml of tetrahydrofuran and 282 mg of silver trifluoromethanesulphonate in 8 ml of diethyl ether were added simultaneously over a period of 1 hour. After stirring the mixture for a further 2 hours at −2° C., a further 247 mg of the aforementioned chlorosugar in 12 ml of tetrahydrofuran and 141 mg of silver trifluoromethanesulphonate in 4 ml of diethyl ether were added over a period of 40 minutes. The mixture was stirred at −2° C. for a further 30 minutes and was then poured into a mixture of 260 ml of 10% sodium hydrogen carbonate solution and 125 ml of ethyl acetate. The mixture was filtered, the filtrate was transferred into a separating funnel and the layers were separated. The organic extract was washed with two 350 ml portions of water, dried over anhydrous sodium sulphate and evaporated. The crude product was purified by chromatography on a column of 75 g of silica gel using for the elution 800 ml of ethyl acetate/60°–80° C. petroleum ether (1:2, vol/vol) and 150 ml of ethyl acetate/60° C.–80° C. petroleum ether (1:1, vol/vol). There were obtained 360 mg of (1S)-cis-1-[(2,3,6-trideoxy-3-trifluoroacetamido-4-O-p-nitrobenzoyl-α-L-arabinohexopyranosyl)oxy]-1,2,3,4,6,11-hexahydro-3,5,12-trihydroxy-6,11-dioxo-3-[1(R)-(phenylcarbamoyloxy)ethyl]naphthacene in the form of orange crystals of melting point 263°–266° C.; $[\alpha]_D^{20} = +298°$ (c=0.1% in dioxan), together with 280 mg of unreacted dioxonaphthacene starting material.

(b) 1.085 g of the compound obtained according to paragraph (a) were suspended in a mixture of 9 ml of dichloromethane and 825 ml of methanol. 12.6 ml of 0.1M aqueous sodium hydroxide were added and the mixture was stirred at room temperature in a nitrogen atmosphere for 30 minutes. Glacial acetic acid was added until the solution became red and the solution was then concentrated in vacuo. The residue was treated with 1.25 l of water and the mixture was extracted with two 300 ml portions of ethyl acetate. The combined ethyl acetate extracts were dried over anhydrous sodium sulphate and evaporated. The product was purified by chromatography on a column of 200 g of silica gel using for the elution 2 l of dichloromethane, 2 l of acetone/dichloromethane (5:95, vol/vol) and 4 l of acetone/dichloromethane (10:90, vol/vol). There were obtained 580 mg of (1S)-cis-1-[(2,3,6-trideoxy-3-trifluoroacetamido-α-L-arabinohexopyranosyl)oxy]-1,2,3,4,6,11-hexahydro-3,5,12-trihydroxy-6,11-dioxo-3-[1(R)-(phenylcarbamoyloxy)ethyl]naphthacene in the form of an orange solid of melting point 217°–220° C.

(c) A solution of 560 mg of the product obtained according to paragraph (b) in 11 ml of tetrahydrofuran was added to 90 ml of 0.1M aqueous sodium hydroxide and the mixture was stirred at room temperature under nitrogen for 30 minutes. The solution was adjusted to pH 8 by the addition of 2M hydrochloric acid and extracted with five 130 ml portions of dichloromethane. The combined dichloromethane extracts were washed with 130 ml of water, dried over anhydrous sodium sulphate and evaporated to give a red gum. This gum was dissolved in a mixture of 16 ml of dichloromethane and 2 ml of methanol and the solution was treated with 3.4 ml of 0.25M methanolic hydrogen chloride and then with 100 ml of diethyl ether. After standing at 0° C. overnight, the product was filtered off and dried in vacuo, there being obtained 250 mg of (1S)-cis-1-[(3-amino-2,3,6-trideoxy-α-L-arabinohexopyranosyl)oxy]-1,2,3,4,6,11-hexahydro-3,5,12-trihydroxy-6,11-dioxo-3-[1(R)-(phenylcarbamoyloxy)ethyl]naphthacene hydrochloride in the form of a bright orange solid of melting point 175°–178° C.; $[\alpha]_D^{20} = +271°$ (c=0.1% in methanol).

EXAMPLE 20

(a) 190 mg of phenyl isocyanate were added to a solution of 200 mg of (1S)-cis-1-[(2,3,6-trideoxy-4-O-methyl-3-trifluoroacetamido-α-L-lyxohexopyranosyl)oxy]-1,2,3,4,6,11-hexahydro-3,5,12-trihydroxy-3-(2-hydroxyethyl)-6,11-dioxonaphthacene in 15 ml of pyridine and the mixture was stirred under nitrogen at 60° C. for 40 minutes. The solvent was removed in vacuo, the residue was suspended in 50 ml of dichloromethane and the suspension was filtered in order to remove an insoluble byproduct. The filtrate was diluted with 30 ml of dichloromethane and the solution was washed with two 50 ml portions of 2M hydrochloric acid and with two 50 ml portions of water, dried over anhydrous sodium sulphate and evaporated to give 240 mg of an orange gum. This gum was crystallized from a mixture of dichloromethane and diethyl ether to give 124 mg of (1S)-cis-1-[(2,3 6-trideoxy-4-O-methyl-3-trifluoroacetamido-α-L-lyxohexopyranosyl)oxy]-1,2,3,4,6,11-hexahydro-3,5,12-trihydroxy-6,11-dioxo-3-[2-(phenylcarbamoyloxy)ethyl]naphthacene in the form of a bright red solid of melting point 160°–170° C.; $[\alpha]_D^{20} = +161°$ (c=0.05% in dioxan). The mother liquor was evaporated and the residue was chromatographed on a column of 20 g of silica gel using for the elution 800 ml of dichloromethane and 550 ml of acetone/dichloromethane (5:95, vol/vol), there being obtained a further 61 mg of the foregoing product.

(b) 108 mg of the compound obtained according to paragraph (a) were dissolved in 1 ml of tetrahydrofuran. 15 ml of 0.1M aqueous sodium hydroxide were added and the deep purple solution was stirred at room temperature under nitrogen for 95 minutes. The solution was adjusted to pH 8 by the addition of 0.2M hydrochloric acid and was then extracted with five 25 ml portions of dichloromethane. The combined extracts were washed with two 100 ml portions of water, dried over anhydrous sodium sulphate and evaporated to give an orange gum. This gum was dissolved in 2.0 ml of dichloromethane and the solution was cooled to 0° C. 0.63 ml of 0.25M methanolic hydrogen chloride and then 20 ml of diethyl ether were added and the mixture was held at 0° C. overnight. The product was filtered off, washed with 8 ml of diethyl ether and dried in vacuo. There being obtained 92 mg of (1S)-cis-1-[(3-amino-2,3,6-trideoxy-4-O-methyl-α-L-lyxohexopyranosyl)oxy]-1,2,3,4,6,11-hexahydro-3,5,12-trihydroxy-6,11-dioxo-3-[2-(phenylcarbamoyloxy)ethyl]-naphthacene hydrochloride in the form of a bright orange powder of melting point 183°–187° C.; $[\alpha]_D^{20} = +193°$ (c=0.05% in methanol).

The (1S)-cis-1-[(2,3,6-trideoxy-4-O-methyl-3-trifluoroacetamido-α-L-lyxohexopyranosyl)oxy]-1,2,3,4,6,11-hexahydro-3,5,12-trihydroxy-3-(2-hydroxyethyl)-6,11-dioxonaphthacene used as the starting material in paragraph (a) was prepared as follows:

(i) A solution of 700 mg of (1S)-cis-3-(2-acetoxyethyl)-1,2,3,4,6,11-hexahydro-1,3,5,12-tetrahydroxy-6,11-dioxonaphthacene in 83 ml of tetrahydrofuran was stirred at −5° C. in a nitrogen atmosphere and solutions of 562 mg of 2,3,6-trideoxy-4-O-methyl-3-trifluoroacetamido-α-L-lyxohexopyranosyl chloride in 13 ml of tetrahydrofuran and 733 mg of silver trifluoromethanesulphonate in 22 ml of diethyl ether were added simultaneously over a period of 7 minutes. After stirring the mixture for a further 160 minutes, a further 271 mg of the aforementioned chlorosugar in 7 ml of tetrahydrofuran and a further 370 mg of silver trifluoromethanesulphonate in 11 ml of diethyl ether were added over a period of 3 minutes. The mixture was stirred at −5° C. for a further 70 minutes and then poured into a mixture of 500 ml of 10% sodium hydrogen carbonate solution and 350 ml of ethyl acetate. The mixture was filtered, the filtrate was transferred into a separating funnel and the layers were separated. The aqueous solution was extracted with 80 ml of ethyl acetate and the combined organic extracts were washed with three 500 ml portions of water, dried over anhydrous sodium sulphate and evaporated to give an orange gum. This gum was purified by chromatography on a column of 100 g of silica gel using for the elution 3.25 l of ethyl acetate/60°–80° C. petroleum ether (1:2, vol/vol), 0.75 l of ethyl acetate/60°–80° C. petroleum ether (1:1, vol/vol) and 1 l of ethyl acetate. There were obtained 758 mg of (1S)-cis-3-(2-acetoxyethyl)-1-[(2,3,6-trideoxy-4-O-methyl-3-trifluoroacetamido-α-L-lyxohexopyranosyl)oxy]-1,2,3,4,6,11-hexahydro-3,5,12-trihydroxy-6,11-dioxonaphthacene in the form of a bright orange solid of melting point 116°–120° C.; $[\alpha]_D^{20} = +139.5°$ (c=0.1% in dioxan) after crystallization from a mixture of diethyl ether and 40°–60° C. petroleum ether.

(ii) 600 mg of the compound obtained according to paragraph (i) were dissolved in a mixture of 65 ml of dichloromethane and 65 ml of methanol. 5.0 ml of 0.1M aqueous sodium hydroxide were added and the resulting deep purple solution was stirred at room temperature under nitrogen. Further 5 ml portions of 0.1M aqueous sodium hydroxide were added after total reaction times of 230 minutes and 300 minutes. After a total reaction time of 320 minutes, glacial acetic acid was added to the mixture until it turned bright orange. The solution was poured into a mixture of 200 ml of water and 100 ml of dichloromethane and the layers were separated. The organic extract was dried over anhydrous sodium sulphate and evaporated to give an orange gum. This gum was purified by chromatography on a column of 40 g of silica gel using for the elution 400 ml of dichloromethane, 1050 ml of acetone/dichloromethane (5:95, vol/vol) 350 ml of acetone/dichloromethane (10:90, vol/vol), 375 ml of acetone/dichloromethane (15:85, vol/vol), 400 ml of acetone/dichloromethane (30:70, vol/vol), 375 ml of acetone/dichloromethane (60:40, vol/vol) and 250 ml of acetone, there being obtained 210 mg of (1S)-cis-1-[(2,3,6-trideoxy-4-O-methyl-3-trifluoroacetamido-α-L-lyxohexopyranosyl)oxy]-1,2,3,4,6,11-hexahydro-3,5,12-trihydroxy-3-(2-hydroxyethyl)-6,11-dioxonaphthacene in the form of an orange gum which was used without further purification.

The (1S)-cis-3-(2-acetoxyethyl)-1,2,3,4,6,11-hexahydro-1,3,5,12-tetrahydroxy-6,11-dioxonaphthacene used as the starting material in paragraph (i) was prepared as follows:

A solution of 10.7 g of potassium cyanide in 14.5 ml of water was added to a solution of 21.4 g of (S)-1',2',3',4'-tetrahydro-3'-hydroxy-5',8'-dimethoxyspiro[1,3-dithiolane-2,1'-naphthyl]-3'-methyl p-toluenesulphonate in 285 ml of dimethylformamide. The mixture was stirred at 90° C. under nitrogen for 4 hours, then left to cool and poured into 1.9 l of water. The resulting mixture was extracted with three 475 ml portions of ethyl acetate and the combined extracts were washed with four 1.9 l portions of water, dried over anhydrous sodium sulphate and evaporated. The residue was triturated with 100 ml of diethyl ether and filtered to give 13.4 g of (S)-1',2',3',4'-tetrahydro-3'-hydroxy-5',8'-dimethoxyspiro[1,3-dithiolane-2,1'-naphthalene]-3'-acetonitrile in the form of a white crystalline solid of melting point 173°–174.5° C. $[\alpha]_D^{20} = -28.4°$ (c=0.5% in chloroform).

A solution of the compound obtained according to the preceding paragraph in 180 ml of tetrahydrofuran was added to a stirred suspension of 46.4 g of mercuric oxide and 46.4 g of mercuric chloride in a mixture of 1.49 l of methanol and 134 ml of water. The mixture was stirred at room temperature for 40 minutes and was then concentrated in vacuo to about one quarter of its volume. The resulting mixture was diluted with 1.6 l of dichloromethane and filtered. The solid filter residue was washed with a further 1 l of dichloromethane. The combined filtrates were washed with three 1.5 l portions of water, dried over anhydrous sodium sulphate and evaporated. The residue was triturated with diethyl ether and filtered to give 8.0 g of (S)-1,2,3,4-tetrahydro-3-hydroxy-5,8-dimethoxy-1-oxo-3-naphthaleneacetonitrile in the form of a white solid of melting point 160°–162° C.; $[\alpha]_D^{20} = +15.0°$ (c=0.1% in chloroform).

The compound prepared according to the preceding paragraph was dissolved in 800 ml of tetrahydrofuran and 1.785 g of lithium borohydride were added to the solution. The mixture was stirred at room temperature under nitrogen for 80 minutes. The solvent was removed in vacuo and 260 ml of 10% ammonium chloride solution were added to the residue. The resulting mixture was extracted with three 260 ml portions of ethyl acetate and the combined extracts were washed with 260 ml of water, dried over anhydrous sodium sulphate and evaporated. The residue was suspended in 650 ml of toluene and 5.94 g of benzeneboronic acid and 0.208 g of p-toluenesulphonic acid were added. The mixture was stirred at room temperature under nitrogen for 2 days and then washed with two 280 ml portions of 10% potassium hydrogen carbonate solution, dried over anhydrous sodium sulphate and evaporated. The residue was triturated with 50 ml of diethyl ether and filtered to give 8.73 g of (1S)-cis-1,2,3,4-tetrahydro-3-cyanomethyl-5,8-dimethoxy-1,3-naphthalenediyl benzeneboronate in the form of a white crystalline solid of melting point 124°-127° C.; $[\alpha]_D^{20} = +57.3°$ (c=0.1% in chloroform).

8.7 g of the compound prepared according to the preceding paragraph were dissolved in 400 ml of toluene and the solution was stirred under nitrogen and cooled to 0° C. 24.9 ml of a 1.2M solution of diisobutylaluminium hydride in toluene were added and the mixture was stirred at 0° C. for 40 minutes. 400 ml of 2M sulphuric acid were added slowly to the mixture, which was then transferred into a separating funnel and the layers were separated. The aqueous solution was extracted with two 400 ml portions of ethyl acetate and the extracts were combined with the toluene solution. The resulting solution was washed with 400 ml of saturated sodium hydrogen carbonate solution, dried over anhydrous sodium sulphate and evaporated to give 8.35 g of (1S)-cis-3-(formylmethyl)-1,2,3,4-tetrahydro-5,8-dimethoxy-1,3-naphthalenediyl benzeneboronate in the form of a pale yellow gum which was used without further purification.

The compound prepared according to the preceding paragraph was dissolved in 240 ml of tetrahydrofuran and 1.17 g of sodium borohydride were added to the solution. The mixture was stirred for 1 hour at room temperature and the solvent was then removed in vacuo. 215 ml of 2M hydrochloric acid were added dropwise to the residue and the resulting mixture was extracted with three 200 ml portions of dichloromethane. The combined extracts were washed with 200 ml of water, dried over anhydrous sodium sulphate and evaporated to give 8.38 g of (1S)-cis-1,2,3,4-tetrahydro-3-(2-hydroxyethyl)-5,8-dimethoxy-1,3-naphthacenediyl benzeneboronate in the form of a pale yellow gum which was used without further purification.

The compound prepared according to the preceding paragraph was dissolved in 100 ml of pyridine and 13.2 ml of acetic anhydride were added. The solution was stored at room temperature overnight and then 370 g of ice were added in portions. The mixture was acidified with 2M hydrochloric acid and extracted with three 450 ml portions of dichloromethane. The combined extracts were washed with 300 ml of 2M hydrochloric acid and 450 ml of water, dried over anhydrous sodium sulphate and evaporated. The crude product was chromatographed on a column of 500 g of silica gel using ethyl acetate/n-hexane (1:2, vol/vol) for the elution, there being obtained 5.995 g of (1S)-cis-3-(2-acetoxyethyl)-1,2,3,4-tetrahydro-5,8-dimethoxy-1,3-naphthalenediyl benzeneboronate in the form of a white solid of melting point 94°-95° C.; $[\alpha]_D^{20} = +52.9°$ (c=0.1% in chloroform).

A solution of 16.57 g of ammonium ceric nitrate in 275 ml of water was added over a period of 5 minutes to a solution of 5.99 g of the benzeneboronate prepared according to the preceding paragraph in 275 ml of acetonitrile. The mixture was stirred at room temperature for a further 5 minutes and was then poured into 1.3 l of water. The resulting mixture was extracted with four 370 ml portions of dichloromethane and the combined extracts were washed with 370 ml of water, dried over anhydrous sodium sulphate and evaporated to give 5.22 g of (1S)-cis-3-(2-acetoxyethyl)-1,2,3,4,5,8-hexahydro-5,8-dioxo-1,3-naphthalenediyl benzeneboronate in the form of a light brown oil which was used without further purification.

3.34 g of trans-1,2-diacetoxy-1,2-dihydrobenzocyclobutene were added to a solution of the benzeneboronate prepared according to the preceding paragraph in 300 ml of xylene and the mixture was heated at 140° C. under a nitrogen atmosphere for 3 hours. The solution was cooled and the solvent was removed in vacuo. The residue was triturated with 30 ml of diethyl ether and filtered to give 5.19 g of (1S)-cis-3-(2-acetoxyethyl)-1,2,3,4,5,12-hexahydro-5,12-dioxo-1,3-naphthacenediyl benzeneboronate in the form of a yellow solid of melting point 150°-153° C.; $[\alpha]_D^{20} = +135°$ (c=0.1% in chloroform).

The compound prepared according to the preceding paragraph was dissolved in a mixture of 275 ml of dry pyridine and 137.5 ml of acetic anhydride. 275 mg of 10% palladium-on-carbon were added and the mixture was hydrogenated at room temperature and atmospheric pressure for 1 hour. The catalyst was removed by filtration and the filter cake was washed with dichloromethane. The combined filtrates were evaporated, the residue was triturated with 30 ml of diethyl ether and filtered to give 4.09 g of (1S)-cis-5,12-diacetoxy-3-(2-acetoxyethyl)-1,2,3,4-tetrahydro-1,3-naphthacenediyl benzeneboronate in the form of a light brown solid of melting point 198°-200° C.

The compound prepared according to the preceding paragraph was dissolved in a mixture of 240 ml of glacial acetic acid and 80 ml of acetic anhydride. 3.22 g of finely ground chromium trioxide were added and the mixture was stirred at room temperature for 16 hours. The mixture was poured into 700 ml of water and the resulting suspension was extracted with four 360 ml portions of dichloromethane. The combined extracts were washed with two 380 ml portions of water, dried over anhydrous sodium sulphate and evaporated. The residue was triturated with 30 ml of diethyl ether and filtered to give 2.27 g of (1S)-cis-5,12-diacetoxy-3-(2-acetoxyethyl)-1,2,3,4,6,11-hexahydro-6,11-dioxo-1,3-naphthacenediyl benzeneboronate in the form of a pale yellow solid of melting point 162°-165° C.

A solution of the compound prepared according to the preceding paragraph in 430 ml of dichloromethane was cooled to −78° C. A solution of 2.5 g of boron trichloride in 10 ml of dichloromethane was added and the mixture was stirred and left to warm to 0° C. over a period of 45 minutes. The mixture was poured into 430 ml of ice-cold 2M hydrochloric acid and the layers were separated. The aqueous layer was extracted with two 365 ml portions of dichloromethane and the combined organic solutions were washed with two 300 ml portions of water, dried over anhydrous sodium sulphate and evaporated to give 2.05 g of (1S)-cis-3-(2-acetoxyethyl)-1,2,3,4,6,11-hexahydro-5,12-dihydroxy-6,11-dioxo-1,3-naphthacenediyl benzeneboronate in the form of a red solid which was used without further purification.

The benzeneboronate prepared according to the preceding paragraph was dissolved in a mixture of 200 ml of dichloromethane, 40 ml of 2-methyl-2,4-pentanediol and 4 ml of acetic acid and the solution was heated under reflux for 2.5 hours. The solution was then cooled, washed with four 480 ml portions of water, dried over anhydrous sodium sulphate and evaporated.

The residue was crystallized from a mixture of diethyl ether and n-hexane and filtered to give 1.5 g of (1S)-cis-3-(2-acetoxyethyl)-1,2,3,4,6,11-hexahydro-1,3,5,12-tetrahydroxy-6,11-dioxonaphthacene in the form of a red solid of melting point 120°–125° C.; $[\alpha]_D^{20} = +110°$ (c = 0.1% in dioxan).

The aforementioned (1S)-cis-3-(2-acetoxyethyl)-1,2,3,4-tetrahydro-5,8-dimethoxy-1,3-naphthalenediyl benzeneboronate can also be prepared as follows:

3.3 g of a 50% dispersion of sodium hydride in mineral oil were added to 35 ml of dry dimethyl sulphoxide stirred at 70° C. The mixture was stirred at 70° C. until the evolution of hydrogen had ceased. After cooling to 0° C., 35 ml of dry tetrahydrofuran were added. 5.0 g of methyl (1S)-1',2',3',4'-tetrahydro-2'-hydroxy-5',8'-dimethoxyspiro[1,3-dithiolane-2,4'-naphthalene]-2'-carboxylate in 30 ml of dry tetrahydrofuran were added over a period of 10 minutes. After stirring at 0° C. for 15 minutes, the mixture was poured into 200 ml of water and acidified to pH 3 with hydrochloric acid. The solution was extracted with five 100 ml portions of dichloromethane. The combined dichloromethane extracts were washed with 200 ml of water, dried over magnesium sulphate and evaporated to give 5.5 g of crude β-ketosulphoxide in the form of an orange gum.

The product obtained according to the preceding paragraph was dissolved in 50 ml of pyridine and 20 ml of acetic anhydride and the solution was cooled to 0° C. while stirring. 0.25 g of 4-dimethylaminopyridine was added and the mixture was held at 0° C. for 18 hours. The solution was then poured on to 300 g of crushed ice and left to stand for 1 hour. The mixture was then extracted with four 150 ml portions of dichloromethane.

The combined extracts were washed with 500 ml of water, with two 500 ml portions of 2M hydrochloric acid, with 500 ml of water and with 500 ml of 10% potassium hydrogen carbonate solution. After drying over anhydrous sodium sulphate, the solvent was removed by evaporation to give a dark yellow gum which was dissolved in 100 ml of dry tetrahydrofuran. The solution was added dropwise to a stirred mixture of 2.5 g of lithium aluminium hydride in 100 ml of tetrahydrofuran cooled to 0° C. After completion of the addition, the mixture was allowed to come to room temperature, stirred at this temperature for 1 hour and then heated under reflux for 1 hour. After cooling to 0° C., the reaction was quenched by the careful addition of 20 ml of water followed by 200 ml of 2M hydrochloric acid. The mixture was extracted with four 150 ml portions of dichloromethane and the combined extracts were washed with 200 ml of 2M sodium hydroxide solution and with 200 ml of water. After drying, the solvent was removed by evaporation and the residue was chromatographed on silica gel using firstly ethyl acetate/n-hexane (1:1, vol/vol) and then ethyl acetate for the elution. After evaporation of the solvent, there were obtained 2.17 g of a stereoisomeric mixture 1',2',3',4'-tetrahydro-3'-hydroxy-5',8'-dimethoxyspiro[1,3-dithiolane-2,1'-naphthalene]-3'-(1S)-ethane,1,2(RS)-diol in the form of an orange foam of melting point 80°–95° C.; $[\alpha]_D^{20} = -12.9°$ (c = 0.5% in chloroform).

0.9 g of the triol obtained according to the preceding paragraph was dissolved in 100 ml of ethyl acetate containing 0.35 g of benzeneboronic acid and 2 drops of acetic acid. After heating at 70° C. for 30 minutes, the solvent was evaporated to give 1.15 g of a yellow gum which was dissolved in 25 ml of pyridine. The solution was cooled to 0° C. and treated with 0.6 g of mesyl chloride. The mixture was held at 0° C. for 18 hours and then the solvent was removed by evaporation. The residue was dissolved in a mixture of 10 ml of dichloromethane, 2 ml of 2-methyl-2,4-pentanediol and 0.5 ml of acetic acid. After standing at 20° C. for 2 days, the mixture was diluted with 75 ml of dichloromethane and the solution was washed with five 75 ml portions of water. After drying, the solvent was removed by evaporation to give 1.0 g of the crude mesylate in the form of a pale yellow gum.

The product obtained according to the preceding paragraph was dissolved in 20 ml of tetrahydrofuran and 100 ml of 0.5M aqueous sodium hydroxide were added. After stirring for 6 hours, the solution was extracted with six 50 ml portions of dichloromethane and the combined extracts were dried and evaporated to give 0.8 g of a yellow gum. This gum was dissolved in 20 ml of tetrahydrofuran and the solution was added dropwise to a stirred suspension of 0.5 g of lithium aluminium hydride in tetrahydrofuran. The mixture was heated under reflux for 1 hour, cooled to 0° C. and quenched by the careful addition of 5 ml of water. The solvent was removed by evaporation and the residue was extracted with 100 ml of ethyl acetate and with 50 ml of water. The ethyl acetate extract was dried and evaporated to give the crude product in the form of a yellow gum. Purification by column chromatography on silica gel using ethyl acetate/n-hexane (1:1, vol/vol) for the elution gave 0.52 g of (1S)-1',2',3',4'-tetrahydro-3'-hydroxy-3'-(2-hydroxyethyl)-5',8'-dimethoxyspiro[1,3-dithiolane-2,1'-naphthalene] in the form of a colourless gum.

0.5 g of (1S)-1',2',3',4'-tetrahydro-3'-hydroxy-3'-(2-hydroxyethyl)-5',8'-dimethoxyspiro[1,3-dithiolane-2,1'-naphthalene] was dissolved in 10 ml of dry pyridine and 0.5 g of acetic anhydride was added to the solution. The mixture was left to stand at room temperature for 20 hours and then poured into ice-cold 5M sulphuric acid. The resulting mixture was extracted with ethyl acetate, the extracts were washed with water and sodium hydrogen carbonate solution, dried and evaporated to give 0.56 g of (1S)-3'-(2-acetoxyethyl)-1',2',3',4'-tetrahydro-3'-hydroxy-5',8'-dimethoxyspiro[1,3-dithiolane-2,1'-naphthalene] in the form of a colourless oil which was used directly in the next step.

0.55 g of (1S)-3'-(2-acetoxyethyl)-1',2',3',4'-tetrahydro-3'-hydroxy-5',8'-dimethoxyspiro[1,3-dithiolane-2,1'-naphthalene] in 10 ml of tetrahydrofuran were added to a stirred suspension of 1.65 g of mercuric chloride and 1.65 g of mercuric oxide in 50 ml of methanol containing 3.5 ml of water. After standing at room temperature for 1 hour, about 25 ml of solvent were removed by evaporation under reduced pressure, 50 ml of dichloromethane were added and the resulting suspension was filtered to remove insoluble material. The filtrate was washed with three 50 ml portions of water, dried over magnesium sulphate and evaporated to give a solid residue. Trituration with diethyl ether gave 0.29 g of (1S)-3-(2-acetoxyethyl)-1,2,3,4-tetrahydro-3-hydroxy-5,8-dimethoxy-1-oxo-naphthalene in the form of colourless crystals of melting point 145°–148° C. (decomposition); $[\alpha]_{436}^{20} = +23.9°$ (c = 0.05% in chloroform).

0.25 g of (1S)-3-(2-acetoxyethyl)-1,2,3,4-tetrahydro-3-hydroxy-5,8-dimethoxy-1-oxo-naphthalene was dissolved in 20 ml of dry tetrahydrofuran and 200 mg of sodium borohydride were added. The mixture was stirred at room temperature for 2 hours and the solvent was removed by evaporation. 25 ml of 10% ammonium chloride were added and the mixture was extracted with three 25 ml portions of ethyl acetate. The combined ethyl acetate extracts were washed with saturated sodium chloride solution, dried over magnesium sulphate and evaporated to give a clear colourless oil which was dissolved in 50 ml of ethyl acetate. 0.125 g of benzeneboronic acid and 1 drop of acetic acid were added and the resulting solution was heated under reflux for 1 hour. After evaporation of the solvent, the residue was dissolved in 50 ml of toluene. After the addition of 25 mg of p-toluenesulphonic acid, the solution was stirred at room temperature overnight. The solution was then washed with 10 ml of 10% potassium hydrogen carbonate solution, dried and evaporated. The crude product was purified by chromatography on a column of 30 g of silica gel using ethyl acetate/n-hexane (1:1, vol/vol) for the elution to give 0.32 g of (1S)-cis-3-(2-acetoxyethyl)-1,2,3,4-tetrahydro-5,8-dimethoxy-1,3-naphthalenediyl benzeneboronate in the form of white crystals of melting point 94°–95° C.; $[\alpha]_D^{20} = +52.9°$ (c=0.1% in chloroform).

EXAMPLE 21

(a) A solution of 0.7 g of (1S)-cis-1,2,3,4,6,11-hexahydro-1,3,5,12-tetrahydroxy-6,11-dioxo-3-(p-tolylcarbamoyloxy)methylnaphthacene in 50 ml of tetrahydrofuran was treated with 2.0 g of 2,3,6-trideoxy-4-O-p-nitrobenzoyl-3-trifluoroacetamido-α-L-arabinohexopyranosyl chloride and 1.0 g of silver trifluoromethanesulphonate according to the procedure described in Example 8(a). Crystallization of the crude product from dichloromethane/diethyl ether gave 0.61 g of (1S)-cis-1-[(2,3,6-trideoxy-3-trifluoroacetamido-4-O-p-nitrobenzoyl-α-L-arabinohexopyranosyl)oxy]-1,2,3,4,6,11-hexahydro-3,5,12-trihydroxy-6,11-dioxo-3-(p-tolylcarbamoyloxy)methylnaphthacene in the form of red crystals.

(b) 0.6 g of the compound obtained according to paragraph (a) was treated according to the procedure described in Example 1(b) to give 0.325 g of (1S)-cis-1-[(2,3,6-trideoxy-3-trifluoroacetamido-α-L-arabinohexopyranosyl)oxy]-1,2,3,4,6,11-hexahydro-3,5,12-trihydroxy-6,11-dioxo-3-(p-tolylcarbamoyloxy)methylnaphthacene in the form of orange crystals of melting point 211°–213° C.; $[\alpha]_D^{20} = +173.6°$ (c=0.05% in dioxan).

(c) 0.325 g of the compound obtained according to paragraph (b) was treated according to the procedure described in Example 1(c) to give 0.31 g of (1S)-cis-1-[(3-amino-2,3,6-trideoxy-α-L-arabinohexopyranosyl)oxy]-1,2,3,4,6,11-hexahydro-3,5,12-trihydroxy-6,11-dioxo-3-(p-tolylcarbamoyloxy)methylnaphthacene hydrochloride in the form of an orange-red powder of melting point 184°–185° C. (decomposition); $[\alpha]_D^{20} = +200.2°$ (c=0.049% in methanol).

The (1S)-cis-1,2,3,4,6,11-hexahydro-1,3,5,12-tetrahydroxy-6,11-dioxo-3-(p-tolylcarbamoyloxy)methylnaphthacene used as the starting material in paragraph (a) was prepared as follows:

(i) 1.1 g of (1S)-cis-1,2,3,4,6,11-hexahydro-5,12-dihydroxy-3-hydroxymethyl-6,11-dioxo-1,3-naphthacenediyl benzeneboronate were dissolved in 100 ml of dry pyridine containing 1.8 g of p-tolyl isocyanate. The mixture was heated at 80° C. for 110 minutes and worked-up according to the procedure described in Example 1(i) to give (1S)-cis-1,2,3,4,6,11-hexahydro-5,12-dihydroxy-6,11-dioxo-3-(p-tolylcarbamoyloxy)methyl-1,3-naphthacenediyl benzeneboronate in the form of a red gum.

(ii) The compound obtained according to the procedure described in paragraph (i) was treated according to the procedure described in Example 1(ii) to give 0.83 g of (1S)-cis-1,2,3,4,6,11-hexahydro-1,3,5,12-tetrahydroxy-6,11-dioxo-3-(p-tolylcarbamoyloxy)methylnaphthacene in the form of red crystals of melting point 215°–218° C.; $[\alpha]_D^{20} = +132.9°$ (c=0.05% in dioxan).

EXAMPLE 22

(a) 0.4 g of (1S)-cis-1-[(2,3,6-trideoxy-3-trifluoroacetamido-4-O-methyl-α-L-lyxohexopyranosyl)oxy]-1,2,3,4,6,11-hexahydro-3,5,12-trihydroxy-3-hydroxymethyl-6,11-dioxonaphthacene was suspended in 50 ml of dichloromethane and 0.225 g of trichloroacetyl isocyanate was added. The mixture was stirred under nitrogen at room temperature for 1 hour and then the clear red solution obtained was washed with 50 ml of water and evaporated. The resulting red gum was then dissolved in a mixture of 100 ml of dichloromethane and 100 ml of methanol and the solution was treated with 0.1M aqueous sodium hydroxide to give a deep purple colour. After 3 hours, acetic acid was added to restore the orange colour, the solution was washed with 50 ml of dilute hydrochloric acid and then with 50 ml of water, dried and evaporated. The residue was purified by chromatography on silica gel using ethyl acetate for the elution, there being obtained 0.415 g of (1S)-cis-3-(carbamoyloxy)methyl-1-[(2,3,6-trideoxy-3-trifluoroacetamido-4-O-methyl-α-L-lyxohexopyranosyl)oxy]-1,2,3,4,6,11-hexahydro-3,5,12-trihydroxy-6,11-dioxonaphthacene in the form of an orange powder of melting point 152°–154° C.; $[\alpha]_D^{20} = +169.0°$ (c=0.049% in dioxan).

(b) 0.39 g of the compound obtained according to paragraph (a) was treated according to the procedure described in Example 9(b) to give 0.3 g of (1S)-cis-1-[(3-amino-2,3,6-trideoxy-4-O-methyl-α-L-lyxohexopyranosyl)oxy]-3-(carbamoyloxy)methyl-1,2,3,4,6,11-hexahydro-3,5,12-trihydroxy-6,11-dioxonaphthacene hydrochloride in the form of an orange-red powder of melting point 194°–196° C. (decomposition); $[\alpha]_D^{20} = +145.9°$ (c=0.049% in methanol).

EXAMPLE 23

(a) A solution of 1.0 g of (1S)-cis-1,2,3,4,6,11-hexahydro 1,3,5,12-tetrahydroxy-6,11-dioxo-3-(phenylcarbamoyloxy)methylnaphthacene in 100 ml of tetrahydrofuran was treated with 1.2 g of 2,3,6-trideoxy-3-trifluoroacetamido-4-O-methyl-α-L-lyxohexopyranosyl chloride and 0.75 g of silver trifluoromethanesulphonate according to the procedure described in Example 1(a). After purification of the product by chromatography, in addition to 0.215 g of unreacted dioxonaphthacene starting material, there was obtained by precipitation from a dichloromethane solution using n-hexane 0.475 g of (1S)-cis-1-[(2,3,6-trideoxy-3-trifluoroacetamido-4-O-methyl-α-L-lyxohexopyranosyl)oxy]-1,2,3,4,6,11-hexahydro-3,5,12-trihydroxy-6,11-dioxo-3-(phenylcarbamoyloxy)methylnaphthacene in the form of an orange powder of melting point 137°–142° C.; $[\alpha]_D^{20} = +106.0°$ (c=0.051% in dioxan).

(b) 0.475 g of the compound obtained according to paragraph (a) was dissolved in 10 ml of tetrahydrofuran and the solution was added to 60 ml of 0.25N aqueous sodium hydroxide. The mixture was stirred at room temperature for 45 minutes and then the pH of the solution was adjusted to 8–9 by the addition of 0.2M aqueous hydrochloric acid. The solution was extracted repeatedly with dichloromethane containing 10% ethanol until the extracts were virtually colourless. The combined extracts were washed with water, dried over anhydrous sodium sulphate and evaporated to give a red gum. This gum was dissolved in 20 ml of dichloromethane, filtered and 4 ml of 0.165M methanolic hydrogen chloride were added to the filtrate. 200 ml of dry diethyl ether were added while swirling to give the product as an orange precipitate. After filtration and drying in vacuo, there was obtained 0.355 g of (1S)-cis-1-[(3-amino-2,3,6-trideoxy-4-O-methyl-α-L-lyxohexopyranosyl)oxy]-1,2,3,4,6,11-hexahydro-3,5,12-trihydroxy-6,11-dioxo-3-(phenylcarbamoyloxy)methylnaphthacene hydrochloride in the form of an orange powder of melting point 183°–185° C. (decomposition); $[\alpha]_D^{20} = +172.3°$ (c=0.051% in methanol).

EXAMPLE 24

(a) A solution of 1.0 g of (1S)-cis-1,2,3,4,6,11-hexahydro-1,2,3,12-tetrahydroxy-3-[(o-nitrobenzylcarbamoyloxy)methyl]-6,11-dioxonaphthacene in 70 ml of tetrahydrofuran was treated with 1.6 g of 2,3,6-trideoxy 3-trifluoroacetamido-4-O-methyl-α-L-lyxohexopyranosyl chloride and 0.8 g of silver trifluoromethanesulphonate according to the procedure described in Example 1(a). After purification of the product by chromatography, there was obtained by precipitation from a dichloromethane solution using n-hexane 0.42 g of (1S)-cis-[(2,3,6-trideoxy-3-trifluoroacetamido-4-O-methyl-α-L-lyxohexopyranosyl)oxy]-1,2,3,4,6,11-hexahydro-3,5,12-trihydroxy-3-[(o-nitrobenzylcarbamoyloxy)methyl]-6,11-dioxonaphthacene in the form of an orange powder of melting point 130°–135° C.; $[\alpha]_D^{20} = +138.8°$ (c=0.05% in dioxan).

(b) 0.4 g of the compound obtained according to paragraph (a) was treated according to the procedure described in Example 23(b) to give (1S)-cis-1-[(3-amino-2,3,6-trideoxy-4-O-methyl-α-L-lyxohexopyranosyl)oxy]-1,2,3,4,6,11-hexahydro-3,5,12-trihydroxy-3-[(o-nitrobenzylcarbamoyloxy)methyl]-6,11-dioxonaphthacene hydrochloride in the form of an orange powder of melting point 175°–177° C. (decomposition); $[\alpha]_D^{20} = +130.8°$ (c=0.051% in methanol).

The (1S)-cis-1,2,3,4,6,11-hexahydro-1,2,3,12-tetrahydroxy-3-[(o-nitrobenzylcarbamoyloxy)methyl]-6,11-dioxonaphthacene used as the starting material in paragraph (a) was prepared a follows:

(i) 1.0 g of (1S)-cis-1,2,3,4,6,11-hexahydro-5,12-dihydroxy-3-hydroxymethyl-6,11-dioxo-1,3-naphthacenediyl benzeneboronate was dissolved in 100 ml of dry pyridine containing 1.5 g of o-nitrobenzyl isocyanate and the mixture was heated at 80° C. for 1.5 hours. After working-up according to the procedure described in Example 1(i), there was obtained (1S)-cis-1,2,3,4,6,11-hexahydro-5,12-dihydroxy-3-[(o-nitrobenzylcarbamoyloxy)methyl]-6,11-dioxo-1,3-naphthacenediyl benzeneboronate in the form of an orange gum.

(ii) The compound obtained according to the procedure described in paragraph (i) was treated according to the procedure described in Example 1(ii) to give 1.2 g of (1S)-cis-1,2,3,4,6,11-hexahydro-1,3,5,12-tetrahydroxy-3-[(o-nitrobenzylcarbamoyloxy)methyl]-6,11-dioxonaphthacene in the form of red crystals of melting point 123°–125° C.; $[\alpha]_D^{20} = +91.1°$ (c=0.05% in dioxan).

EXAMPLE 25

(a) A solution of 0.71 g of (1S)-cis-1,2,3,4,6,11-hexahydro-1,3,5,12-tetrahydroxy-3-(2-thienylcarbamoyloxy)methyl-6,11-dioxonaphthacene in 50 ml of tetrahydrofuran was treated with two 1.0 g portions of 2,3,6-trideoxy-4-O-p-nitrobenzoyl-3-trifluoroacetamido-α-L-arabinohexopyranosyl chloride and two 0.5 g portions of silver trifluoromethanesulphonate according to the procedure described in Example 8(a). After purification of the product by chromatography, there was obtained 0.56 g of (1S)-cis-1-[(2,3,6-trideoxy-3-trifluoroacetamido-4-O-p-nitrobenzoyl-α-L-arabinohexopyranosyl)oxy]-1,2,3,4,6,11-hexahydro-3,5,12-trihydroxy-3-(2-thienylcarbamoyloxy)methyl-6,11-dioxonaphthacene in the form of orange-red crystals.

(b) 0.56 g of the compound obtained according to paragraph (a) was treated according to the procedure described in Example 1(b) to give 0.35 g of (1S)-cis-1-[(2,3,6-trideoxy-3-trifluoroacetamido-α-L-arabinohexopyranosyl)oxy]-1,2,3,4,6,11-hexahydro-3,5,12-trihydroxy-3-(2-thienylcarbamoyloxy)methyl-6,11-dioxonaphthacene in the form of orange crystals of melting point 212°–215° C.; $[\alpha]_D^{20} = +166.2°$ (c=0.049% in dioxan).

(c) 0.45 g of the compound obtained according to the procedure described in paragraph (b) was treated according to the procedure described in Example 1(c) to give 0.325 g of (1S)-cis-1-[(3-amino-2,3,6-trideoxy-α-L-arabinohexopyranosyl)oxy]-1,2,3,4,6,11-hexahydro-3,5,12-trihydroxy-3-(2-thienylcarbamoyloxy)methyl-6,11-dioxonaphthacene hydrochloride in the form of an orange powder of melting point 193°–194° C. (decomposition); $[\alpha]_D^{20} = +183.9°$ (c=0.05% in methanol).

EXAMPLE 26

(a) A solution of 1.3 g of (1S)-cis-1,2,3,4,6,11-hexahydro-1,3,5,12-tetrahydroxy-3-(3-thienylcarbamoyloxy)-methyl-6,11-dioxonaphthacene in 80 ml of tetrahydrofuran was treated with 1.5 g of 2,3,6-trideoxy-4-O-p-nitrobenzoyl-3-trifluoroacetamido-α-L-arabinohexopyranosyl chloride and 0.75 g of silver trifluoromethanesulphonate according to the procedure described in Example 8(a). After chromatography, in addition to 0.32 g of unreacted dioxonaphthacene starting material, there was obtained 0.88 g of (1S)-cis-1-[(2,3,6-trideoxy-3-trifluoroacetamido-4-O-p-nitrobenzoyl-α-L-arabinohexopyranosyl)oxy]-1,2,3,4,6,11-hexahydro-3,5,12-trihydroxy-3-(3-thienylcarbamoyloxy)methyl-6,11-dioxonaphthacene in the form of orange-red crystals of melting point 258°–259° C.; $[\alpha]_D^{20} = -263.4°$ (c=0.05% in dioxan).

(b) 0.67 g of the compound obtained according to paragraph (a) was treated according to the procedure described in Example 1(b) to give 0.51 g of (1S)-cis-1-[(2,3,6-trideoxy-3-trifluoroacetamido-α-L-arabinohexopyranosyl)oxy]-1,2,3,4,6,11-hexahydro-3,5,12-trihydroxy-3-(3-thienylcarbamoyloxy)methyl-6,11-dioxonaphthacene in the form of orange crystals of melting point 228°–230° C.; $[\alpha]_D^{20} = +197.0°$ (c=0.051% in dioxan).

(c) 0.48 g of the compound obtained according to the procedure described in paragraph (c) was treated according to the procedure described in Example 1(c) to give 0.4 g of (1S)-cis-1-[(3-amino-2,3,6-trideoxy-α-L-arabinohexopyranosyl)oxy]-1,2,3,4,6,11-hexahydro-3,5,12-trihydroxy-3-(3-thienylcarbamoyloxy)methyl-6,11-dioxonaphthacene hydrochloride in the form of a red-orange crystalline powder of melting point 198°–200° C. (decomposition); $[\alpha]_D^{20} = +192.7°$ (c = 0.051% in dioxan).

The (1S)-cis-1,2,3,4,6,11-hexahydro-1,3,5,12-tetrahydroxy-3-(3-thienylcarbamoyloxy)methyl-6,11-dioxonaphthacene used as the starting material in paragraph (a) was prepared as follows:

(i) 2.5 g of thiophene-3-carboxylic acid azide in 80 ml of dry pyridine was heated at 75° C. for 45 minutes. 1.65 g of (1S)-cis-1,2,3,4,6,11-hexahydro-5,12-dihydroxy-3-hydroxymethyl-6,11-dioxo-1,3-naphthacenediyl benzeneboronate were added and the mixture was heated at 70° C. for 80 minutes. After working-up according to the procedure described in Example 1(i), there was obtained (1S)-cis-1,2,3,4,6,11-hexahydro-5,12-dihydroxy-3-(3-thienylcarbamoyloxy)methyl-6,11-dioxo-1,3-naphthacenediyl benzeneboronate in the form of a red gum. (ii) The compound obtained according to the procedure described in paragraph (i) was treated according to the procedure described in Example 1(ii) to give 1.56 g of (1S)-cis-1,2,3,4,6,11-hexahydro-1,3,5 12-tetrahydroxy-3-(3-thienylcarbamoyloxy)methyl-6,11-dioxonaphthacene in the form of orange-red crystals of melting point 138°–141° C.; $[\alpha]_D^{20} = +118$ 8° (c = 0.049% in dioxan).

EXAMPLE 27

(a) A solution of 1.3 g of (1S)-cis-1,2,3,4,6,11-hexahydro-1,3,5,12-tetrahydroxy-6,11-dioxo-3-(phenylcarbamoyloxy)methylnaphthacene in 90 ml of tetrahydrofuran was treated with 0.9 g of 2,3,6-trideoxy-3-trifluoroacetamido-4-O-methyl-α-L-arabinohexopyranosyl chloride and 0.65 g of silver trifluoromethanesulphonate according to the procedure described in Example 1(a). After purification of the product by column chromatography, in addition to 0.63 g of unreacted dioxonaphthacene starting material, there was obtained 0.72 g of (1S)-cis-1-[(2,3,6-trideoxy-3-trifluoroacetamido-4-O-methyl-α-L-arabinohexopyranosyl)oxy]-1,2,3,4,6,11-hexahydro-3,5,12-trihydroxy-6,11-dioxo-3-(phenylcarbamoyloxy)methylnaphthacene in the form of orange crystals of melting point 243°–244° C.; $[\alpha]_D^{20} = +150.9°$ (c = 0.05% in dioxan).

(b) 0.6 g of the compound obtained according to paragraph (a) was treated according to the procedure described in Example 23(b) to give 0.39 g of (1S)-cis-1-[(3-amino-2,3,6-trideoxy-4-O-methyl-α-L-arabinohexopyranosyl)oxy]-1,2,3,4,6,11-hexahydro-3,5,12-trihydroxy-6,11-dioxo-3-(phenylcarbamoyloxy)methylnaphthacene hydrochloride in the form of an orange powder of melting point 212°–214° C. (decomposition); $[\alpha]_D^{20} = +204.0°$ (c = 0.05% in methanol).

EXAMPLE 28

(a) A solution of 1.2 g of (1S)-cis-1,2,3,4,6,11-hexahydro-1,3,5,12-tetrahydroxy-6,11-dioxo-3-(phenylcarbamoyloxy)methylnaphthacene in 90 ml of tetrahydrofuran was treated with 0.9 g of 2,3,6-trideoxy-4-O-ethyl-3-trifluoroacetamido-α-L-lyxohexopyranosyl chloride and 0.6 g of silver trifluoromethanesulphonate according to the procedure described in Example 1(a). After purification of the product by column chromatography, in addition to 0.6 g of unreacted dioxonaphthacene starting material, there was obtained 0.9 g of (1S)-cis-1-[(2,3,6-trideoxy-4-O-ethyl-3-trifluoroacetamido-α-L-lyxohexopyranosyl)oxy]-1,2,3,4,6,11-hexahydro-3,5,12-trihydroxy-6,11-dioxo-3-(phenylcarbamoyloxy)methylnaphthacene in the form of an orange powder of melting point 138°–143° C. (after precipitation from a dichloromethane solution using n-hexane); $[\alpha]_D^{20} = +122.5°$ (c = 0.05% in dioxan).

(b) 0.73 g of the compound obtained according to paragraph (a) was treated according to the procedure described in Example 23(b) to give 0.45 g of (1S)-cis-1-[(3-amino-2,3,6-trideoxy-4-O-ethyl-α-L-lyxohexopyranosyl)oxy]-1,2,3,4,6,11-hexahydro-3,5,12-trihydroxy-6,11-dioxo-3-(phenylcarbamoyloxy)methylnaphthacene hydrochloride in the form of an orange powder of melting point 178°–180° C. (decomposition); $[\alpha]_D^{20} = +131.5°$ (c = 0.05% in methanol).

The 2,3,6-trideoxy-4-O-ethyl-3-trifluoroacetamido-α-L-lyxohexopyranosyl chloride used as the starting material in paragraph (a) was prepared as follows:

(i) 5.0 g of methyl 3-acetamido-2,3,6-trideoxy-β-L-lyxohexopyranoside were heated at 45° C. in the dark in a mixture of 25 ml of ethyl iodide and 20 ml of dimethylformamide containing 10 g of silver oxide. After 17 hours, the mixture was filtered through Celite and the filtrate was evaporated. The gum obtained was purified by column chromatography to give 3.4 g of methyl 3-acetamido-2,3,6-trideoxy-4-O-ethyl-β-L-lyxohexopyranoside in the form of colourless crystals of melting point 199°–200° C.; $[\alpha]_D^{20} = -75.0°$ (c = 0.5% in methanol).

(ii) 3.0 g of the compound obtained according to paragraph (i) were dissolved in 53 ml of water containing 10.5 g of barium hydroxide. The mixture was heated under reflux for 20 hours, cooled and then diluted with 100 ml of water. Carbon dioxide was bubbled through the mixture for 1 hour and, after filtration, the filtrate was evaporated to give a white solid which was dried over potassium hydroxide at 50° C. The dry product was suspended in 80 ml of dry diethyl ether and cooled to 0° C. while 10 ml of trifluoroacetic anhydride were added dropwise. The resulting mixture was stirred at room temperature for 18 hours, filtered and evaporated to give a white crystalline solid. After trituration with a mixture of diethyl ether/n-hexane, there were obtained 1.4 g of methyl 2,3,6-trideoxy-4-O-ethyl-3-trifluoroacetamido-β-L-lyxohexopyranoside in the form of colourless crystals of melting point 183°–185° C.; $[\alpha]_D^{20} = -88.3°$ (c = 0.49% in methanol).

(iii) 1.4 g of the compound obtained according to paragraph (ii) was suspended in 38 ml of a 20% (vol/vol) mixture of acetic acid and water and heated under reflux for 3 hours. The solvent was removed by evaporation and the residue was purified by column chromatography to give 1.2 g of 2,3,6-trideoxy-4-O-ethyl-3-trifluoroacetamido-L-lyxohexopyranoside in the form of colourless crystals of melting point 183°–184° C.; $[\alpha]_D^{20} = -175.4°$ (c = 0.5% in methanol).

(iv) 0.8 g of the compound obtained according to paragraph (iii) was dissolved in 16.5 ml of pyridine at 0° C. and 0.8 g of p-nitrobenzoyl chloride was added while stirring. The mixture was stored at 0° C. for 18 hours and then poured into 200 ml of ice-water. After 30 minutes, the product was extracted with three 50 ml portions of dichloromethane and the combined extracts were washed with two 50 ml portions of 10% sulphuric acid, 50 ml of saturated sodium chloride solution, two 50 ml portions of saturated sodium bicarbonate solution and finally with 50 ml of saturated sodium chloride solution. After drying over anhydrous sodium sulphate, the solvent was removed by evaporation to give 0.96 g of p-nitrobenzoyl 2,3,6-trideoxy-4-O-ethyl-3-trifluoroacetamido-α-L-lyxohexopyranoside in the form of colourless crystals of melting point 148°–150° C.; $[\alpha]_D^{20} = -53.2°$ (c=0.3% in methanol).

(v) 0.9 g of the compound obtained according to paragraph (iv) was dissolved in 40 ml of dichloromethane at 0° C. and hydrogen chloride was bubbled through the solution for 10 minutes at 0° C. The mixture was then stirred at room temperature for 15 minutes and the solvent was removed by evaporation. The residue was stirred with 20 ml of dichloromethane for 10 minutes and then filtered. The filtrate was evaporated to give 0.9 g of crude 2,3,6-trideoxy-4-O-ethyl-3-trifluoroacetamido-α-L-lyxohexopyranosyl chloride which was used directly for the reaction described in paragraph (a).

EXAMPLE 29

(a) A solution of 1.45 g of (1S)-cis-1,2,3,4,6,11-hexahydro-1,3,5,12-tetrahydroxy-6,11-dioxo-3-(phenylcarbamoyloxy)methylnaphthacene in 100 ml of tetrahydrofuran was treated with 1.0 g of 4-O-benzyl-2,3,6-trideoxy-3-trifluoroacetamido-α-L-lyxohexopyranosyl chloride and 0.6 g of silver trifluoromethanesulphonate according to the procedure described in Example 1(a) After purification of the product by column chromatography, in addition to 0.63 g of unreacted dioxonaphthacene starting material, there was obtained by precipitation from a dichloromethane solution using n-hexane 0.77 g of (1S)-cis-1-[(4-O-benzyl-2,3,6-trideoxy-3-trifluoroacetamido-α-L-lyxohexopyranosyl)oxy]-1,2,3,4,6,11-hexahydro-3,5,12-trihydroxy-6,11-dioxo-3-(phenylcarbamoyloxy)methylnaphthacene in the form of an orange powder of melting point 123°–127° C.; $[\alpha]_D^{20} = +67.3°$ (c=0.052% in dioxan).

(b) 0.6 g of the compound obtained according to paragraph (a) was dissolved in 25 ml of tetrahydrofuran and the solution was added to 60 ml of 0.5M aqueous sodium hydroxide. The mixture was stirred at room temperature for 45 minutes and then the pH of the solution was adjusted to 8–9 by the addition of 0.5M aqueous hydrochloric acid. The solution was extracted repeatedly with dichloromethane until the extracts were virtually colourless. The combined extracts were washed with water, dried over anhydrous sodium sulphate and evaporated to give a red gum. This gum was dissolved in 20 ml of dichloromethane, filtered and 4.5 ml of 0.16M methanolic hydrogen chloride were added to the filtrate. 200 ml of dry diethyl ether were then added while swirling, the product being obtained in the form of an orange precipitate. After filtration and drying in vacuo, there was obtained 0.45 g of (1S)-cis-1-[(3-amino-4-O-benzyl-2,3,6-trideoxy-α-L-lyxohexopyranosyl)oxy]-1,2,3,4,6,11-hexahydro-3,5,12-trihydroxy-6,11-dioxo-3-(phenylcarbamoyloxy)methylnaphthacene hydrochloride in the form of an orange powder of melting point 175°–178° C. (decomposition); $[\alpha]_D^{20} = +61.3°$ (c=0.051% in methanol).

The 4-O-benzyl-2,3,6-trideoxy-3-trifluoroacetamido-α-L-lyxohexopyranosyl chloride used as a starting material in paragraph (a) was prepared as follows:

(i) 5.0 g of methyl 3-acetamido-2,3,6-trideoxy-β-L-lyxohexopyranoside were dissolved in a mixture of 75 ml of dry dimethylformamide and 3.2 ml of benzyl bromide containing 15 g of silver oxide. The mixture was stirred in the dark for 72 hours, filtered and the filtrate was evaporated to give a crystalline mixture consisting of product and unreacted starting material. Separation of the product by column chromatography gave 2.1 g of methyl 4-O-benzyl-2,3,6 -trideoxy-3-trifluoroacetamido-β-L-lyxohexopyranoside in the form of colourless crystals of melting point 159°–160° C.; $[\alpha]_D^{20} = -89.2°$ (c=0.5% in methanol).

(ii) 2.5 g of the compound obtained according to paragraph (a) were dissolved in 15 ml of ethanol and the resulting solution was added to a stirred mixture of 13.5 g of barium hydroxide and 35 ml of water. The mixture was heated under reflux for 4 days, cooled and then diluted with 150 ml of water. Carbon dioxide was bubbled through the mixture for 1 hour and, after filtration, the filtrate was evaporated to give a residue which was dried at 70° C. over phosphorus pentoxide. The dry residue was suspended in 75 ml of anhydrous diethyl ether at 0° C. and 10 ml of trifluoroacetic anhydride were added dropwise while stirring. The resulting mixture was stirred at room temperature overnight, filtered and the filtrate was evaporated to give a white residue which was purified by column chromatography. There were obtained 2.47 g of methyl 4-O-benzyl-2,3,6-trideoxy-3-trifluoroacetamido-β-L-lyxohexopyranoside in the form of colourless crystals of melting point 176°–177° C.; $[\alpha]_D^{20} = -92.8°$ (c=0.5% in methanol).

(iii) 2.05 g of the compound obtained according to paragraph (ii) were suspended in 45 ml of a 20% (vol/vol) mixture of acetic acid and water and the resulting mixture was heated under reflux for 2.5 hours. The solvent was removed by evaporation and the residue was triturated with n-hexane to give 1.5 g of 4-O-benzyl-2,3,6-trideoxy-3-trifluoroacetamido-L-lyxohexopyranoside in the form of colourless crystals of melting point 205°–206° C.; $[\alpha]_D^{20} = -168.5°$ (c=0.5% in methanol).

(iv) 1.5 g of the compound obtained according to paragraph (iv) were dissolved in 25 ml of pyridine at 0° C. and 1.22 g of p-nitrobenzoyl chloride were added while stirring. The mixture was stored at 0° C. for 18 hours and then poured into 400 ml of ice-water. After 0.5 hour, the product was extracted with three 100 ml portions of dichloromethane and the combined extracts were washed with two 100 ml portions of 10% sulphuric acid, 100 ml of saturated sodium chloride solution, two 100 ml portions of saturated sodium bicarbonate solution and finally 100 ml of saturated sodium chloride solution. After drying, the solvent was removed by evaporation to give (from diethyl ether) 1.7 g of p-nitrobenzoyl-4-O-benzyl-2,3,6-trideoxy-3-trifluoroacetamido-L-lyxohexopyranoside in the form of colourless crystals of melting point 132°–136°; $[\alpha]_D^{20} = -126°$ (c=0.5% in methanol).

(v) 1.0 g of the compound obtained according to paragraph (iv) was dissolved in 40 ml of dichloromethane at 0° C. and hydrogen chloride was bubbled through the solution for 10 minutes at 0° C. The mixture was then stirred at room temperature for 15 minutes and the solvent was removed by evaporation. The residue was stirred for 10 minutes with 20 ml of dichloromethane and then filtered The filtrate was evaporated to give 1.0 g of crude 4-O-benzyl-2,3,6-trideoxy-3-trifluoroacetamido-α-L-lyxohexopyranosyl chloride which was used directly for the reaction described in paragraph (a).

EXAMPLE 30

(a) A mixture of 0.6 g of (1S)-cis-1-[(2,3,4,6-tetradeoxy-3-trifluoroacetamido-α-L-threohexopyranosyl)oxy]-1,2,3,4,6,11-hexahydro-3,5,12-trihydroxy-3-hydroxymethyl-6,11-dioxonaphthacene and 70 mg of butane-1,4-diisocyanate in 10 ml of dry pyridine was left to stand at room temperature for 3 weeks. The solvent was then removed by evaporation and the residue was purified by chromatography to give, in addition to 120 mg of unreacted starting material, 364 mg of 3,3'-[tetramethylenebis(carbamoylmethylene)]bis-(1S)-cis-1-[(2,3,4,6-tetradeoxy-3-trifluoroacetamido-α-L-threohexopyranosyl)oxy]-1,2,3,4,6,11-hexahydro-3,5,12-trihydroxy-6,11-dioxonaphthacene in the form of an orange powder of melting point 173°-175° C.; $[\alpha]_D^{20} = +196.1°$ (c=0.049% in dioxan).

(b) 0.52 g of the compound obtained according to paragraph (a) was treated according to the procedure described in Example 9(b) to give 0.42 g of 3,3'-[tetramethylenebis(carbamoyloxymethylene)]bis-(1S)-cis-[(3-amino 2,3,4,6-tetradeoxy-α-L-threohexopyranosyl-)oxy]-1,2,3,4,6,11-hexahydro-3,5,12-trihydroxy-6,11-dioxonaphthacene dihydrochloride in the form of an orange powder of melting point 182°-185° C. (decomposition); $[\alpha]_D^{20} = +274.9°$ (c=0.051% in methanol).

EXAMPLE 31

(a) A solution of 1.1 g of (1S)-cis-3-(4-chlorophenylcarbamoyloxy)methyl-1,2,3,4,6,11-hexahydro-1,3,5,12-tetrahydroxy-6,11-dioxonaphthacene in 100 ml of tetrahydrofuran and 7 ml of dimethylformamide was treated with 1.0 g of 2,3,6-trideoxy-4-O-p-nitrobenzoyl-3-trifluoroacetamido-α-L-arabinohexopyranosyl chloride and 0.5 g of silver trifluoromethanesulphonate according to the procedure described in Example 2(a). After crystallization, there was obtained 0.96 g of (1S)--cis-3-(4-chlorophenylcarbamoyloxy)methyl-1-[(2,3,6-trideoxy-3-trifluoroacetamido-4-O-p-nitrobenzoyl-α-L-arabinohexopyranosyl)oxy]-1,2,3,4,6,11-hexahydro-3,5,12-trihydroxy-6,11-dioxonaphthacene in the form of red crystals of melting point 267°-268° C.

(b) 0.8 g of the compound obtained according to paragraph (a) was treated according to the procedure described in Example 1(b) to give 0.53 g of (1S)-cis-3-(4-chlorophenylcarbamoyloxy)methyl-1-[(2,3,6-trideoxy-3-trifluoroacetamido-α-L-arabinohexopyranosyl)oxy]-1,2,3,4,6,11-hexahydro-3,5,12-trihydroxy-6,11-dioxonaphthacene in the form of orange crystals of melting point 206°-208° C.; $[\alpha]_D^{20} = +175.8°$ (c=0.05% in dioxan).

(c) 0.49 g of the compound obtained according to paragraph (b) was treated according to the procedure described in Example 1(c) to give 0.46 g of (1S)-cis-1-[(3-amino-2,3,6-trideoxy-α-L-arabinohexopyranosyl-)oxy]-3-(4-chlorophenylcarbamoyloxy)methyl-1,2,3,4,6,11-hexahydro-3,5,12-trihydroxy-6,11-dioxonaphthacene hydrochloride in the form of an orange-red powder of melting point 183°-187° C. (decomposition); $[\alpha]_D^{20} = +192.4°$ (c=0.051% in methanol).

EXAMPLE 32

(a) A solution of 1.05 g of (1S)-cis-3-(trichloroacetylcarbamoyloxy)methyl-1,2,3,4,6,11-hexahydro-1,3,5,12-tetrahydroxy-6,11-dioxonaphthacene in 60 ml of tetrahydrofuran was treated with 1.5 g of 2,3,6-trideoxy-4-O-p-nitrobenzoyl-3-trifluoroacetamido-α-L-arabinohexopyranosyl chloride and 0.5 g of silver trifluoromethanesulphonate according to the procedure described in Example 8(a). After purification by chromatography, crude (1S)-cis-3-(trichloroacetylcarbamoyloxy)methyl-1-[(2,3,6-trideoxy-3-trifluoroacetamido- 4-O-p-nitrobenzoyl-α-L-arabinohexopyranosyl)oxy]-1,2,3,4,6,11-hexahydro-3,5,12-trihydroxy-6,11-dioxonaphthacene was obtained in the form of a red gum.

(b) The compound obtained according to paragraph (a) was dissolved in a mixture of 75 ml of dichloromethane and 75 ml of methanol and 0.5M sodium hydroxide solution was added to produce a deep purple colour. After 3 hours, the orange colour was restored by the addition of acetic acid. The mixture was diluted by adding 300 ml of water and the ii product was extracted with three 100 ml portions of dichloromethane. The combined extracts were dried over anhydrous sodium sulphate and evaporated to give a red residue. Crystallization from ethyl acetate gave 0.46 g of (1S)-cis-3-(carbamoyloxy)methyl-1-[(2,3,6-trideoxy-3-trifluoroacetamido-α-L-arabinohexopyranosyl)oxy]-1,2,3,4,6,11-hexahydro-3,5,12-trihydroxy-6,11-dioxonaphthacene in the form of orange-red crystals of melting point 246°-247° C.; $[\alpha]_D^{20} = +197.1°$ (c=0.5% in dioxan).

(c) 0.5 g of the compound obtained according to paragraph (b) was treated according to the procedure described in Example 1(c) to give 0.37 g of (1S)-cis-1-[(3-amino-2,3,6-trideoxy-α-L-arabinohexopyranosyl-)oxy]-3-(carbamoyloxy)methyl-1,2,3,4,6,11-hexahydro-3,5,12-trihydroxy-6,11-dioxonaphthacene hydrochloride in the form of an orange powder of melting point 184°-185° C. (decomposition); $[\alpha]_D^{20} = +216.7°$ (c=0.51% in methanol).

The (1S)-cis-3-(trichloroacetylcarbamoyloxy)methyl-1,2,3,4,6,11-hexahydro-1,3,5,12-tetrahydroxy-6,11-dioxonaphthacene used as the starting material in paragraph (a) was prepared as follows:

(i) 1.0 g of (1S)-cis-1,2,3,4,6,11-hexahydro-5,12-dihydroxy-3-hydroxymethyl-6,11-dioxo-1,3-naphthacenediyl benzeneboronate was suspended in 200 ml of dichloromethane and 0.5 g of trichloroacetyl isocyanate was added. After stirring at room temperature for 1 hour, a clear red solution was obtained. The solvent was removed by evaporation and the residue was dissolved in a mixture of 15 ml of dichloromethane, 15 ml of 2-methyl-2,4-pentanediol and 3 ml of acetic acid. The resulting mixture was left to stand at room temperature overnight. The solution was then diluted with 100 ml of dichloromethane and washed with four 75 ml portions of water. After drying over anhydrous sodium sulphate, the solvent was removed by evaporation and the residue was triturated with a mixture of ethyl acetate and diethyl ether, there being obtained 1.1 g of (1S)-cis-3-(trichloroacetylcarbamoyloxy)methyl-1,2,3,4,6,11-hexahydro-1,3,5,12-tetrahydroxy-6,11-dioxonaphthacene in the form of a red powder of melting point 125°-128° C.; $[\alpha]_D^{20} = +91.9°$ (c=0.05% in dioxan).

EXAMPLE 33

(a) A solution of 0.86 g of (1S)-cis-1,2,3,4,6,11-hexahydro-1,3,5,12-tetrahydroxy-6,11-dioxo-3-[1(S)-(phenylcarbamoyloxy)ethyl]naphthacene in 60 ml of tetrahydrofuran was treated with 1.0 g of 2,3,6-trideoxy-4-O-p-nitrobenzoyl-3-trifluoroacetamido-α-L-arabinohexopyranosyl chloride and 0.5 g of silver trifluoromethanesulphonate according to the procedure described in Example 19(a). Crystallization of the crude product from ethyl acetate/diethyl ether yielded 0.6 g of (1S)-cis-1-[(2,3,6-trideoxy-3-trifluoroacetamido-4-O-p-nitrobenzoyl-α-L-arabinohexopyranosyl)oxy]-1,2,3,4,6,11-hexahydro-3,5,12-trideoxy-6,11-dioxo-3-[1(S)-(phenylcarbamoyloxy)ethyl]naphthacene in the form of orange crystals of melting point 278°-282° C.

(b) 0.565 g of the compound obtained according to paragraph (a) was treated according to the procedure described in Example 1(b) to give 0.45 g of (1S)-cis-1-[(2,3,6-trideoxy-3-trifluoroacetamido-α-L-arabinohexopyranosyl)oxy]-1,2,3,4,6,11-hexahydro-3,5,12-trihydroxy-6,11-dioxo-3-[1(S)-(phenylcarbamoyloxy)ethyl]-naphthacene in the form of orange crystals of melting point 266°–267° C.; $[\alpha]_D^{20} = +131.2°$ (c=0.05% in dioxan).

(c) 0.42 g of the compound obtained according to paragraph (b) was treated according to the procedure described in Example 19(c) to give 0.35 g of (1S)-cis-1-[(3-amino-2,3,6-trideoxy-α-L-arabinohexopyranosyl)oxy]-1,2,3,4,6,11-hexahydro-3,5,12-trihydroxy-6,11-dioxo-3-[1(S)-(phenylcarbamoyloxy)ethyl]naphthacene hydrochloride in the form of an orange solid of melting point 188°–190° C. (decomposition); $[\alpha]_D^{20} = +179.8°$ (c=0.051% in methanol).

The (1S)-cis-1,2,3,4,6,11-hexahydro-1,3,5,12-tetrahydroxy-6,11-dioxo-3-[1(S)-(phenylcarbamoyloxy)ethyl]-naphthacene used as the starting material in paragraph (a) was prepared as follows:

(i) 1.0 g of (1S)-cis-1,2,3,4,6,11-hexahydro-5,12-dihydroxy-3-[1(S)-(hydroxy)ethyl]-6,11-dioxo-1,3-naphthacenediyl benzeneboronate was treated with 1.5 g of phenyl isocyanate according to the procedure described in Example 18(i) to give crude (1S)-cis-1,2,3,4,6,11 hexahydro-5,12-dihydroxy-6,11-dioxo-3-[1(S)-(phenylcarbamoyloxy)ethyl]-1,3-naphthacenediyl benzeneboronate in the form of a red gum which was used without further purification.

(ii) The benzeneboronate obtained according to paragraph (i) was treated according to the procedure described in Example 18(ii) to give 0.925 g of (1S)-cis-1,2,3,4,6,11-hexahydro-1,3,5,12-tetrahydroxy-6,11-dioxo-3-[1(S)-(phenylcarbamoyloxy)ethyl]naphthacene in the form of a red powder of melting point 155°–160° C.; $[\alpha]_D^{20} = +61.9°$ (c=0.05% in dioxan).

The (1S)-cis-1,2,3,4,6,11-hexahydro-5,12-dihydroxy-3-[1(S)-(hydroxy)ethyl]-6,11 dioxo-1,3-naphthacenediyl benzeneboronate used as the starting material in paragraph (i) was prepared as follows:

The (1S)-cis-3-[1(S)-(acetoxy)ethyl]-1,2,3,4-tetrahydro-5,8-dimethoxy-1,3-naphthacenediyl benzeneboronate obtained as described in Example 18 was treated according to an analogous sequence of reactions as described for the corresponding (1S)-cis-3-[1(R)-(acetoxy)ethyl]-isomer to give the following compounds:

(1S)-cis-3-[1(S)-(acetoxy)ethyl]-1,2,3,4,5,12-hexahydro-5,12-dioxo-1,3-naphthacenediyl benzeneboronate as yellow crystals of melting point 172°–174° C.; $[\alpha]_D^{20} = +98.7°$ (c=0.05% in chloroform);

(1S)-cis-5,12-diacetoxy-3-[1(S)-(acetoxy)ethyl]-1,2,3,4-tetrahydro-1,3-naphthacenediyl benzeneboronate as pale yellow crystals of melting point 238°–240° C.; $[\alpha]_D^{20} = +208.2°$ (c=0.05% in chloroform);

(1S)-cis-5,12-diacetoxy-3-[1(S)-(acetoxy)ethyl]-1,2,3,4,6,11-hexahydro-6,11-dioxo-1,3-naphthacenediyl benzeneboronate as pale yellow crystals of melting point 178°–180° C.; $[\alpha]_D^{20} = +146.6°$ (c=0.05% in chloroform); and (1S)-cis-1,2,3,4,6,11-hexahydro-5,12-dihydroxy-3-[1(S)-(hydroxy)ethyl]-6,11-dioxo-1,3-naphthacenediyl benzeneboronate as red crystals of melting point 224°–226° C.; $[\alpha]_D^{20} = +269.9°$ (c=0.05% in dioxan).

EXAMPLE 34

(a) A solution of 220 mg of (1S)-cis-1,2,3,4,6,11-hexahydro-1,3,5,12-tetrahydroxy-6,11-dioxo-3-[1(R)-(phenylcarbamoyloxy)ethyl]naphthacene in 37 ml of tetrahydrofuran was stirred at −6° C. in a nitrogen atmosphere and solutions of 155 mg of 2,3,6-trideoxy-3-trifluoroacetamido-4-O-methyl-α-L-lyxohexopyranosyl chloride in 6 ml of tetrahydrofuran and 206 mg of silver trifluoromethanesulphonate in 10 ml of diethyl ether were added simultaneously over a period of 10 minutes. After stirring the mixture for a further 2 hours at −5° C., a further 77 mg of the aforementioned chlorosugar in 3 ml of tetrahydrofuran and a further 103 mg of silver trifluoromethanesulphonate in 5 ml of diethyl ether were added to the mixture over a period of 8 minutes. The mixture was stirred at −7° C. for a further 110 minutes and then poured into a mixture of 165 ml of 10% sodium hydrogen carbonate solution and 75 ml of ethyl acetate. The mixture was filtered, the filtrate was transferred into a separating funnel and the layers were separated. The organic layer was washed with two 250 ml portions of water, dried over anhydrous magnesium sulphate and evaporated. The residue was chromatographed on a column of 40 g of silica gel using ethyl acetate/40°–60° C. petroleum ether (1:3, vol/vol) for the elution, there being obtained 305 mg of (1S)-cis-1-[(2,3,6-trideoxy-3-trifluoroacetamido-4-O-methyl-α-L-lyxohexopyranosyl)oxy]-1,2,3,4,6,11-hexahydro-3,5,12-trihydroxy-6,11-dioxo-3-[1(R)-(phenylcarbamoyloxy)ethyl]naphthacene which was used without further purification.

(b) A solution of 117 mg of the compound obtained according to paragraph (a) in 1 ml of tetrahydrofuran was added to 37 ml of 0.1M aqueous sodium hydroxide and the deep purple mixture was stirred at room temperature under nitrogen for 4 hours. The solution was adjusted to pH 8 by the addition of 5M hydrochloric acid and the mixture was extracted with four 20 ml portions of dichloromethane. The combined extracts were washed with 30 ml of water, dried over anhydrous sodium sulphate and evaporated. The residue was dissolved in 1 ml of dichloromethane and 0.9 ml of 0.25M methanolic hydrogen chloride and subsequently 45 ml of diethyl ether were added. The mixture was left to stand at 0° C. overnight. The product was filtered off and dried in vacuo, there being obtained 31 mg of (1S)-cis-1-[(3-amino-2,3,6-trideoxy-4-O-methyl-α-L-lyxohexopyranosyl)oxy]-1,2,3,4,6,11-hexahydro-3,5,12-trihydroxy-6,11-dioxo-3-[1(R)-(phenylcarbamoyloxy)ethyl] naphthacene hydrochloride in the form of a bright red powder of melting point 177°–182° C.; $[\alpha]_D^{20} = +101°$ (c=0.05% in dioxan).

What is claimed is:

1. A compound of the formula

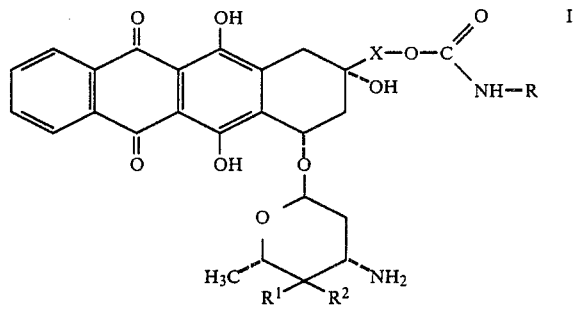

wherein R a hydrogen atom, lower alkyl, phenyl, substituted phenyl, phenyl-(lower alkyl) or substituted phenyl-(lower alkyl) group, a pyridyl or thienyl group or a group of the formula $$-(CH_2)_n-COR' \quad (a)$$

or

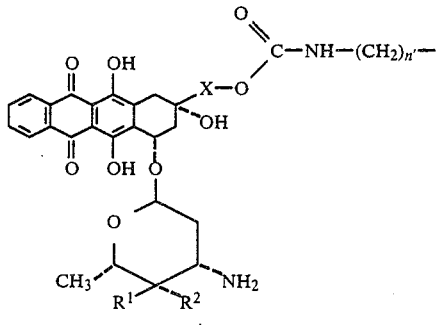

wherein R' is a hydroxy, lower alkoxy, amino, lower alkylamino, di(lower alkyl)-amino or phenyl amino or substituted phenyl amine group, n140 stands for an integer or 1 to 4, n' stands for an integer of 2 to 10, $R^1$ and $R^2$ each are a hydrogen atom or one of $R^1$ and $R^2$ is a hydrogen atom and the other is a hydroxy, lower alkoxy or benzyloxy group and X is a group of the formula $$-CH_2-, \quad -\overset{CH_3}{\underset{|}{CH}}- \quad \text{or} \quad -CH_2-CH_2-,$$
$$(i) \qquad (ii) \qquad\qquad (iii)$$

and pharmaceutically acceptable acid addition salts thereof.

2. A compound of claim 1, wherein R is a lower alkyl, phenyl, substituted phenyl, phenyl or substituted phenyl-(lower alkyl), a pyridyl or thienyl group or a group of formula (a) and $R^1$ and $R^2$ each are a hydrogen atom or one of $R^1$ and $R^2$ is a hydrogen atom and the other is a hydroxy or a methoxy group.

3. A compound of claim 2, wherein R is phenyl.

4. A compound of claim 3, wherein one of $R^1$ and $R^2$ represents a hydrogen atom and the other represents a hydroxy group.

5. A compound of claim 4, wherein X represents a group of formula

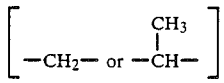

6. A compound of claim 1: (1S)-cis-1-[(3-amino-2,3,6-trideoxy-α-L-lyxohexopyranosyl)oxy]-1,2,3,4,6,11-hexahydro 3,5,12 trihydroxy-6,11-dioxo-3-(phenylcarbamoyloxy)methylnaphthacene and pharmaceutically acceptable acid addition salts thereof.

7. A compound of claim 1: (1S)-cis-1-[(3-amino-2,3,6-trideoxy-α-L-arabinohexopyranosyl)oxy]-1,2,3,4,6,11 hexahydro-3,5,12-trihydroxy-6,11-dioxo-3-(phenylcarbamoyloxy)methylnaphthacene and pharmaceutically acceptable acid addition salts thereof.

8. A compound of claim 1: (1S)-cis-1-[(3-amino-2,3,6-trideoxy-α-L-lyxohexopyranosyl)oxy]-1,2,3,4,6,11-hexahydro-3,5,12-trihydroxy 6,11-dioxo-3-[1(R)-(phenylcarbamoyloxy)ethyl]naphthacene and pharmaceutically acceptable acid addition salts thereof.

9. A compound of claim 1: (1S)-cis-1-[(3-amino-2,3,6-trideoxy-α-L-arabinohexopyranosyl)oxy]-1,2,3,4,6,11-hexahydro 3,5,12-trihydroxy-6,11-dioxo-3-[1(R)-(phenylcarbamoyloxy)ethyl]naphthacene and pharmaceutically acceptable acid addition salts thereof.

10. A compound of claim 1 selected from the group consisting of:

(1S)-cis-1-[(3 amino-2,3,6-trideoxy-α-L lyxohexopyranosyl)oxy]-3-(4-chlorophenylcarbamoyloxy)-methyl-1,2,3,4,6,11-hexahydro-3,5,12-trihydroxy-6,11-dioxonaphthacene, (1S)-cis-1-[(3-amino-2,3,6-trideoxy-α-L-lyxohexopyranosyl)oxy]-1,2,3,4,6,11-hexahydro-3,5,12-trihydroxy-3-(4-nitrophenylcarbamoyloxy)methyl-6,11-dioxonaphthacene, (1S)-cis-1-[(3-amino-2,3,6-trideoxy-α-L-lyxohexopyranosyl)oxy]-1,2,3,4,6,11-hexahydro-3,5,12-trihydroxy-3-(4-methoxyphenylcarbamoyloxy)methyl-6,11-dioxonaphthacene, (1S)-cis-1-[(3-amino-2,3,6-trideoxy-α-L-lyxohexopyranosyl)oxy]-1,2,3,4,6,11-hexahydro-3,5,12 trihydroxy-3-(3-hydroxyphenylcarbamoyloxy)methyl-6,11-dioxonaphthacene, (1S)-cis-1-[(3-amino-2,3,6-trideoxy-α-L-lyxohexopyranosyl)oxy]-1,2,3,4,6,11-hexahydro 3,5,12-trihydroxy-3-(methylcarbamoyloxy)methyl-6,11-dioxonaphthacene, (1S)-cis-1-[(3-amino-2,3,6-trideoxy-α-L-lyxohexopyranosyl)oxy]-1,2,3,4,6,11-hexahydro-3,5,12-trihydroxy-3-(2-thienylcarbamoyloxy)methyl-6,11-dioxonaphthacene, (1S)-cis-1-[(3-amino-2,3,4,6-tetradeoxy-α-L-threohexopyranosyl)oxy]-1,2,3,4,6,11-hexahydro-3,5,12-trihydroxy-6,11-dioxo-3-(phenylcarbamoyloxy)methylnaphthacene, (1S)-cis-1-[(3amino-2,3,4,6 tetradeoxy-α-L-threohexopyranosyl)oxy]-1,2,3,4,6,11-hexahydro-3,5,12-trihydroxy-6,11-dioxo-3-(3-pyridylcarbamoyloxy)methylnaphthacene, (1S)-cis-1-[(3-amino-2,3,6-trideoxy-4-O-methyl-α-L-lyxohexopyranosyl)oxy]-3-(benzylcarbamoyloxy)-methyl-1,2,3,4,6,11-hexahydro-3,5,12-trihydroxy-6,11-dioxonaphthacene, (1S)-cis-1-[(3-amino-2,3,6-trideoxy-α-L-lyxohexopyranosyl)oxy]-3-[(2-carboxyethyl)carbamoyloxy]-methyl-1,2,3,4,6,11-hexahydro-3,5,12-trihydroxy-6,11-dioxonaphthacene, (1S)-cis-1-[(3-amino-2,3,6-trideoxy-α-L-lyxohex-
opyranosyl)oxy]-1,2,3,4,6,11-hexahydro-3,5,12-trihy-
droxy-3-[[2-(methoxycarbonyl)ethyl]carbamoyloxy]-
methyl-6,11-dioxonaphthacene, (1S)-cis-1-[(3-amino-2,3,6-trideoxy-α-L-lyxohex-
opyranosyl)oxy]-1,2,3,4,6,11-hexahydro-3,5,12-trihy-
droxy-6,11-dioxo-3-[[2-(propylcarbamoyl)ethyl]car-
bamoyloxy]methylnaphthacene, (1S)-cis-1-[(3-amino-2,3,6-trideoxy-α-L-arabinohex-
opyranosyl)oxy]-1,2,3,4,6,11-hexahydro-3,5,12-trihy-
droxy-6,11-dioxo-3-[[2-(propylcarbamoyl)ethyl]car-
bamoyloxy]methylnaphthacene, (1S)-cis-1-[(3-amino-2,3,6-trideoxy-4-O-methyl-α-L-
lyxohexopyranosyl)oxy]-1,2,3,4,6,11 hexahydro-
3,5,12-trihydroxy-6,11-dioxo-3-[2-(phenylcar-
bamoyloxy)ethyl]naphthacene, and pharmaceutically
acceptable acid addition salts thereof.

11. A compound of claim 1 selected from the group
consisting of:
(1S)-cis-1-[(3-amino-2,3,6-trideoxy-α-L-arabinohex-
opyranosyl)oxy]-1,2,3,4,6,11-hexahydro-3,5,12-trihy-
droxy-6,11-dioxo-3-(p-tolylcarbamoyloxy)methyl-
naphthacene (1S)-cis-1-[(3-amino-2,3,6-trideoxy-4-O-methyl-α-L-
lyxohexopyranosyl)oxy]-3-(carbamoyloxy)methyl-
1,2,3,4,6,11-hexahydro-3,5,12-trihydroxy-6,11-diox-
onaphthacene, (1S)-cis-1-[(3-amino-2,3,6-trideoxy-4-O-methyl-α-L-
lyxohexopyranosyl)oxy]-1,2,3,4,6,11-hexahydro-
3,5,12-trihydroxy-6,11-dioxo-3-(phenylcarbamoylox-
y)methylnaphthacene, (1S)-cis-1-[(3-amino-2,3,6-trideoxy-4-O-methyl-α-L-
lyxohexopyranosyl)oxy]-1,2,3,4,6,11-hexahydro-
3,5,12-trihydroxy- 3-[(o-nitrobenzylcarbamoyloxy)-
methyl]-6,11-dioxonaphthacene, (1S)-cis-1-[(3-amino-2,3,6-trideoxy-α-L-arabinohex-
opyranosyl)oxy]-1,2,3,4,6,11-hexahydro-3,5,12-trihy-
droxy-3-(2-thienylcarbamoyloxy)methyl-6,11-diox-
onaphthacene, (1S)-cis-1-[(3-amino-2,3,6-trideoxy-α-L-arabinohex-
opyranosyl)oxy]-1,2,3,4,6,11-hexahydro-3,5,12-trihy-
droxy-3-(3-thienylcarbamoyloxy methyl-6,11-diox-
onaphthacene, (1S)-cis-1-[(3-amino-2,3,6-trideoxy-4-O-methyl-α-L-
arabinohexopyranosyl)oxy]-1,2,3,4,6,11-hexahydro-
3,5,12-trihydroxy-6,11-dioxo-3-(phenylcarbamoylox-
y)methylnaphthacene, (1S)-cis-1-[(3-amino-2,3,6-trideoxy-4-O-ethyl-α-L-lyx-
ohexopyranosyl)oxy]-1,2,3,4,6,11-hexahydro-3,5,12-
trihydroxy-6,11-dioxo-3-(phenylcarbamoyloxy)me-
thylnaphthacene, (1S)-cis-1-[(3-amino-4-O-benzyl-2,3,6-trideoxy-α-L-lyx-
ohexopyranosyl)oxy]-1,2,3,4,6,11-hexahydro-3,5,12-
trihydroxy-6,11-dioxo-3-(phenylcarbamoyloxy)me-
thylnaphthacene, 3,3'-[tetramethylenebis(carbamoyloxymethylene)]bis-
(1S)-cis-[(3-amino-2,3,4,6-tetradeoxy-α-L-threohex-
opyranosyl)oxy]-1,2,3,4,6,11-hexahydro-3,5,12-trihy-
droxy-6,11-dioxonaphthacene, (1S)-cis-1-[(3-amino-2,3,6-trideoxy-α-L-arabinohex-
opyranosyl)oxy]-3-(4-chlorophenylcarbamoyloxy)-
methyl-1,2,3,4,6,11-hexahydro-3,5,12-trihydroxy-
6,11-dioxonaphthacene, (1S)-cis-1-[(3-amino-2,3,6-trideoxy-α-L-arabinohex-
opyranosyl)oxy]-3-(carbamoyloxy)methyl-
1,2,3,4,6,11-hexahydro- 3,5,12-trihydroxy-6,11-diox-
onaphthacene, (1S)-cis-1-[(3-amino-2,3,6-trideoxy-α-L-arabinohex-
opyranosyl)oxy]-1,2,3,4,6,11-hexahydro-3,5,12-trihy-
droxy-6,11-dioxo-3-[1(S)-(phenylcarbamoyloxy)e-
thyl]naphthacene, 1(S)-cis-1-[(3-amino-2,3,6-trideoxy-4-O-methyl-α-L-
lyxohexopyranosyl)oxy]-1,2,3,4,6,11-hexahydro-
3,5,12-trihydroxy-6,11-dioxo-3-[1(R)-(phenylcar-
bamoyloxy)ethyl]naphthacene and pharmaceutically
acceptable acid addition salts thereof.

12. A compound of the formula

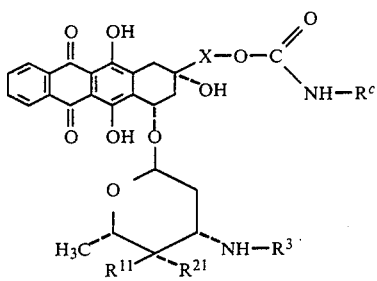

VIb wherein $R^c$ is a trichloroacetyl, lower alkyl, phenyl,
substituted phenyl, phenyl or substituted phenyl-(lower
alkyl), a pyridyl or thienyl group, a group of formula (a)
as in claim 1 or a group of the formula

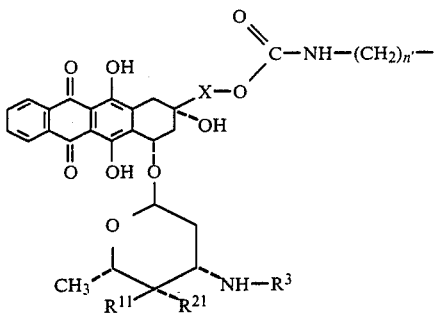

(d)

$R^3$ is an amino protecting group, $R^{11}$ and $R^{21}$ each are a
hydrogen atom or one of $R^{11}$ and $R^{21}$ is hydrogen atom
and the other is lower alkoxy, benzyloxy or protected
hydroxy group and n' and X are as in claim 1, with the
proviso that any carboxy, hydroxy or amino group
present on a phenyl or substituted phenyl substituent is
in protected form and a carboxy group present on
group (a) is in protected form.

13. A compound of the formula

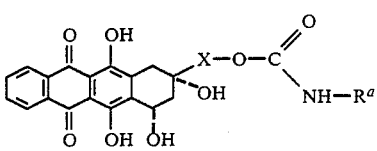

II wherein $R^a$ is a hydrogen atom, a trichloroacetyl, lower
alkyl, phenyl, substituted phenyl, phenyl or substituted
phenyl-(lower alkyl), a pyridyl or thienyl group, a
group of formula (a) as in claim 1 or a group of the
formula

55

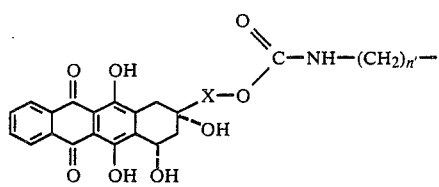

(c)

and n' and are as in claim 1, with the proviso that any carboxy, hydroxy or amino group present on a phenyl or substituted phenyl substituent is in protected form and a carboxy group present on group (a) is in protected form.

* * * * *

56

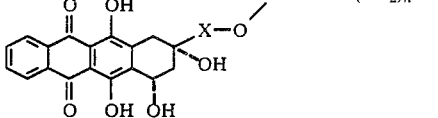

(c)

and n' and are as in claim 1, with the proviso that any carboxy, hydroxy or amino group present on a phenyl or substituted phenyl substituent is in protected form and a carboxy group present on group (a) is in protected form.

* * * * *